(12) United States Patent
Hedrick et al.

(10) Patent No.: US 9,284,404 B2
(45) Date of Patent: Mar. 15, 2016

(54) ANTIMICROBIAL POLYMERS AND METHODS OF MANUFACTURE THEREOF

(75) Inventors: James Hedrick, Pleasanton, CA (US); Kazuki Fukushima, Yonezawa (JP); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 790 days.

(21) Appl. No.: 13/619,958

(22) Filed: Sep. 14, 2012

(65) Prior Publication Data

US 2013/0011457 A1 Jan. 10, 2013

Related U.S. Application Data

(62) Division of application No. 12/646,071, filed on Dec. 23, 2009, now Pat. No. 8,361,495.

(51) Int. Cl.
| | |
|---|---|
| *A61K 9/107* | (2006.01) |
| *C08G 63/64* | (2006.01) |
| *A61K 31/14* | (2006.01) |
| *C08G 64/18* | (2006.01) |
| *C08G 64/30* | (2006.01) |

(52) U.S. Cl.
CPC .............. *C08G 63/64* (2013.01); *A61K 9/1075* (2013.01); *C08G 64/18* (2013.01); *C08G 64/30* (2013.01); *A61K 31/14* (2013.01); *Y10S 977/773* (2013.01); *Y10S 977/904* (2013.01)

(58) Field of Classification Search
None
See application file for complete search history.

(56) References Cited

U.S. PATENT DOCUMENTS

| 6,521,736 | B2 | 2/2003 | Watterson et al. |
| 6,699,724 | B1 | 3/2004 | West et al. |
| 2005/0079197 | A1* | 4/2005 | Kataoka et al. ............... 424/423 |
| 2008/0153982 | A1* | 6/2008 | Lai et al. ........................ 525/91 |
| 2008/0281044 | A1 | 11/2008 | Monahan et al. |
| 2008/0300379 | A1 | 12/2008 | Mullen et al. |

(Continued)

FOREIGN PATENT DOCUMENTS

| JP | 2003346797 | 10/2003 |
| JP | 2005112941 | 4/2005 |

(Continued)

OTHER PUBLICATIONS

R Riva, P Lussis, S Lenoir, C Jerome, R Jerome, P Lecomte. "Contribution of "click chemistry" to the synthesis of antimicrobial aliphatic copolyester." Polymer, vol. 49, 2008, pp. 2023-2028.*

(Continued)

*Primary Examiner* — Isaac Shomer
(74) *Attorney, Agent, or Firm* — Michael R. Roberts

(57) ABSTRACT

Biodegradable cationic block copolymers are disclosed, comprising a hydrophilic block comprising first repeat units derived from a first cyclic carbonyl monomer by ring-opening polymerization, wherein more than 0% of the first repeat units comprise a side chain moiety comprising a quaternary amine group; a hydrophobic block comprising second repeat units derived from a second cyclic carbonyl monomer by ring-opening polymerization; an optional endcap group; and a chain fragment derived from an initiator for the ring opening polymerization. The cationic block copolymers form aqueous micelle mixtures suitable for antimicrobial applications.

37 Claims, 18 Drawing Sheets

(56) References Cited

U.S. PATENT DOCUMENTS

| | | | |
|---|---|---|---|
| 2009/0208553 | A1 | 8/2009 | Kemp et al. |
| 2009/0247666 | A1 | 10/2009 | Yu et al. |
| 2010/0015433 | A1 | 1/2010 | Arfsten et al. |
| 2010/0280242 | A1 | 11/2010 | Hedrick et al. |
| 2010/0305281 | A1 | 12/2010 | Fujiwara et al. |
| 2010/0305300 | A1 | 12/2010 | Coulembier et al. |
| 2010/0311917 | A1 | 12/2010 | Hedrick et al. |
| 2010/0317838 | A1 | 12/2010 | Dubois et al. |
| 2011/0151566 | A1 | 6/2011 | Hedrick et al. |
| 2011/0152167 | A1 | 6/2011 | Hedrick et al. |
| 2011/0182996 | A1 | 7/2011 | Fukushima et al. |
| 2011/0243848 | A1 | 10/2011 | Appel et al. |
| 2011/0269917 | A1 | 11/2011 | Fujiwara et al. |

FOREIGN PATENT DOCUMENTS

| | | | |
|---|---|---|---|
| JP | 2006503932 | A | 2/2006 |
| JP | 2006188699 | A | 7/2006 |
| JP | 2007056079 | A | 3/2007 |
| JP | 2009530447 | A | 8/2009 |
| WO | 0194441 | | 12/2001 |
| WO | 2004021976 | A2 | 3/2004 |
| WO | 2007106997 | A1 | 9/2007 |
| WO | 2009100645 | A1 | 8/2009 |

OTHER PUBLICATIONS

USPTO, Final Office Action mailed Jan. 2, 2013, U.S. Appl. No. 12/645,931, filed Dec. 23, 2009, first named inventor Hedrick.
Biela, et al., "One-Pot Synthesis of Star-Shaped Aliphatic Polyesters with Hyperbranched Cores and Their Characterization with Size Exclusion Chromatography," J.PolySciPartAPolyChem, v44, 4214-4221 (2006). Article first published online: May 23, 2006.
Bourissou, et al., "Recent advances in the controlled preparation of poly(a-hydroxy acids): Metal-free catalysts and new monomers," Comptes Rendus Chimie, vol. 10 (2007), 775-794; Available online Jul. 13, 2007.
Chiu, et al., "Synthesis Functional Poly(carbonate-b-ester) Copolymers and Micellar Characterizations," Journal of Applied Polymer Science, vol. 106, 283-292 (2007); Published online Jun. 11, 2007.
Coulembier, et al., "From controlled ring-opening polymerization to biodegradable aliphatic polyester: Especially poly(b-malic acid) derivatives," Prog. Polym. Sci., vol. 31 (2006), 723-747; Available online Sep. 25, 2006.
Dove, "Controlled ring-opening polymerisation of cyclic esters: polymer blocks in self-assembled nanostructures," Chem. Commun., 2008, 6446-6470; First published as an Advance Article on the web Oct. 16, 2008.
Hu, et al., "Aliphatic Poly(ester-carbonate)s Bearing Amino Groups and Its RGD Peptide Grafting," Journal of Polymer Science: Part A: Polymer Chemistry, vol. 46, 7022-7032 (2008); Article first published online: Sep. 24, 2008.
Jerome, et al., "Recent advances in the synthesis of aliphatic polyesters by ring-opening polymerization," Adv. Drug Delivery Reviews, vol. 60 (2008), 1056-1076; available online Feb. 26, 2008.
Kamber, et al., "N-Heterocyclic Carbenes for the Organocatalytic Ring-Opening Polymerization of #—Caprolactone," Macromolecules, 2009, 42(5), 1634-1639); Publication Date (Web): Feb. 17, 2009.
Kamber, et al., "Organocatalytic Ring-Opening Polymerization", Chem. Rev., 2007, 107, 5813-5840; Publication Date (Web): Nov. 8, 2007.
Kamps, et al., "Urea-bearing copolymers for guest-dependent tunable self-assembly," Chem. Commun., 2007, pp. 954-956. First published on the web Dec. 6, 2006.
Kenawy et al., "The Chemistry and Applications of Antimicrobial Polymers: A State-of-the-Art Review" Biomacromolecules, vol. 8, No. 5, May 2007, pp. 1359-1384; Published on Web Apr. 11, 2007.
Kim, et al., "Mixed Micelle Formation through Stereocomplexation between Enantiomeric Poly(lactide) Block Copolymers," Macromolecules 2009, 42, pp. 25-29. Published on the web Dec. 15, 2008.
Lee et al., "Quaternized Polyamidoamine Dendrimers as Novel Gene Delivery System: Relationship between Degree of Quaternization and Their Influences," Bull. Korean Chem. Soc. 2003, vol. 24, No. 11, pp. 1637-1640.
Mei, et al., "Synthesis and Characterization of Novel Glycerol-Derived Polycarbonates with Pendant Hydroxyl Groups" Macromol. Rapid Commun. 2006, v27, i22, 1894-1899. Article first published online: Nov. 16, 2006.
Mintzer, et al., "Nonviral Vectors for Gene Delivery," Chem. Rev. 2009, 109, pp. 259-302. Published on Web Dec. 3, 2008.
Nederberg et al.,"Organocatalytic Ring Opening Polymerization of Trimethylene Carbonate" Biomacromolecules, 2007, 8 (1), 153-160; Published on Web Dec. 7, 2006.
Palermo, et al., "Chemical Structure of Cationic Groups in Amphiphilic Polymethacrylates Modulates the Antimicrobial and Hemolytic Activities," Biomacromolecules, 2009, 10, pp. 1416-1428; published on the web Apr. 8, 2009.
PCT/SG2010/000486, filing date Dec. 23, 2010 International Search Report and Written Opinion; mailed Feb. 23, 2011.
Pounder, et al., "Metal free thiol—maleimide 'Click' reaction as a mild functionalisation strategy for degradable polymers", Chem. Commun., 2008, 5158-5160; First published as an Advance Article on the web Sep. 29, 2008.
Pratt, et al.,"Tagging alcohols with cyclic carbonate: a versatile equivalent of (meth)acrylate for ring-opening polymerization" J. Chem. Commun., 2008, pp. 114-116; First published on the web Oct. 25, 2007.
Radowski, et al., "Supramolecular Aggregates of Dendritic Multishell Architectures as Universal Nanocarriers," Angew. Chem. Int. Ed. 2007, 46, 1265-1269; Article first published online: Feb. 5, 2007.
Seow et al., "Functional polycarbonates and their self-assemblies as promising non-viral vectors" J. of Controll. Release (2009) v139, 1, pp. 40-47; published on web May 23, 2009.
Sun, etal., "Formation of Reversible Shell Cross-Linked Micelles from the Biodegradable Amphiphilic Diblock Copolymer Poly(L-cysteine)-block-Poly(L-lactide)," Langmuir 2008, 24, 10099-10106; Published on Web Aug. 13, 2008.
Villiers, et al., (eds), Nanotechnology in Drug Delivery, Biotechnology: Pharmaceutical Aspects, V 10, of Biotechnology (Arlington, VA.), Copyright 2009, American Association of Pharmaceutical Scientists, published by Springer Science+Business Media, New York, NY, Chap. 13, p. 401.
Wang, et al., "Polyethylenimine-grafted polycarbonates as biodegradable polycations for gene delivery" Biomaterials 30 (2009) pp. 4824-4832. Available online Jun. 17, 2009.
Wang, et al.,"Synthesis, characterization and surface modification of low moduli poly(ether carbonate urethane)ureas for soft tissue engineering," Acta Biomaterialia, 2009, pp. 2901-2912. Epub May 4, 2009.
Wiltshire, et al., "Degradable Core Cross-Linked Star Polymers via Ring-Opening Polymerization," Macromolecules, 2006, 39 (13), 4282-4285; Publication Date (Web): Jun. 3, 2006.
Xiong, et al., "Synthesis of PEG-Armed and Polyphosphoester Core-Cross-Linked Nanogel by One-Step Ring-Opening Polymerization," Macromolecules, 2009, 42 (4), 893-896; Publication Date (Web): Jan. 21, 2009.
Zhang et al., "Amphiphilic Triblock Copolycarbonates with Poly(glycerol carbonate) as Hydrophilic Blocks," J. Macromolecules, 2009, 42, pp. 1010-1016; Published on the web Jan. 26, 2009.
Zhao, et al., "PLGA-(L-Asp-alt-diol)x-PLGAs with Different Contents of Pendant Amino Groups: Synthesis and Characterization," Macromol. Biosci. 2005, 5, 636-643; published Jul. 14, 2005.
EPO Extended Search Report, Application No./Patent No. 10839918.9-1302/2516503 PCT/SG2010000486, dated May 13, 2013.
Kondo, et al., Thompson Database WPI, XP002696179; publication No. JP2005112941, publication date Apr. 28, 2005; Abstract.
Riva, et al."Combination of ring-opening polymerization and "click" chemistry towards functionalization of aliphatic polyesters," Chem. Commun., 2005, 5334-5336.

(56) References Cited

OTHER PUBLICATIONS

Riva, et al. "Contribution of "click chemistry" to the synthesis of antimicrobial aliphatic copolyester," Polymer 49 (2008) 2023-2028; available online Mar. 7, 2008.

Zhou, et al., "High Potency and Broad-Spectrum Antimicrobial Peptides Synthesized via Ring-Opening Polymerization of r-Aminoacid-N-carboxyanhydrides," Biomacromolecules 2010, 11, 60-67 and Supplement; Published on Web Dec. 3, 2009.

Detrembleur, et al., "New Functional Aliphatic Polyesters by Chemical Modification of Copolymers of e-Caprolactone with gamma-(2-Bromo-2-methylpropionate)-e-caprolactone, gamma-Bromo-e-caprolactone, and a Mixture of β- and gamma-Ene-e-caprolactone," Macromolecules, 2000, 33 (21), pp. 7751-7760; published Sep. 29, 2000.

EPO search report dated Dec. 18, 2014 EPO application No./patent No. 10839918.9-1302.

Mecerreyes, et al., "Ring-opening polymerization of 6-hydroxynon-8-enoic acid lactone: Novel biodegradable copolymers containing allyl pendent groups," Journal of Polymer Science Part A: Polymer Chemistry, vol. 38, Issue 5, pp. 870-875, Mar. 1, 2000; first published online: Feb. 8, 2000.

Pospiech, et al., "Multiblock Copolymers of l-Lactide and Trimethylene Carbonate," Biomacromolecules, 2005, 6 (1), pp. 439-446; Publication Date (Web): Dec. 17, 2004.

Vroman, et al., "Copolymers of e-caprolactone and quaternized e-caprolactone as gene carriers," Journal of Controlled Release 118 (2007) 136-144; Available online Dec. 12, 2006.

Vroman, et al., "PEGylated quaternized copolymer/DNA complexes for gene delivery," International Journal of Pharmaceutics 344 (2007) 88-95; Available online Jul. 3, 2007.

Guan, et al., "Synthesis and Characterization of Novel Biodegradable Block Copolymer Poly(ethylene glycol)-block-poly (L-lactide-co-2-methyl-2-carboxyl-propylene carbonate)", Journal of Polymer Science: Part A: Polymer Chemistry, vol. 43, 4771-4780 (2005).

* cited by examiner

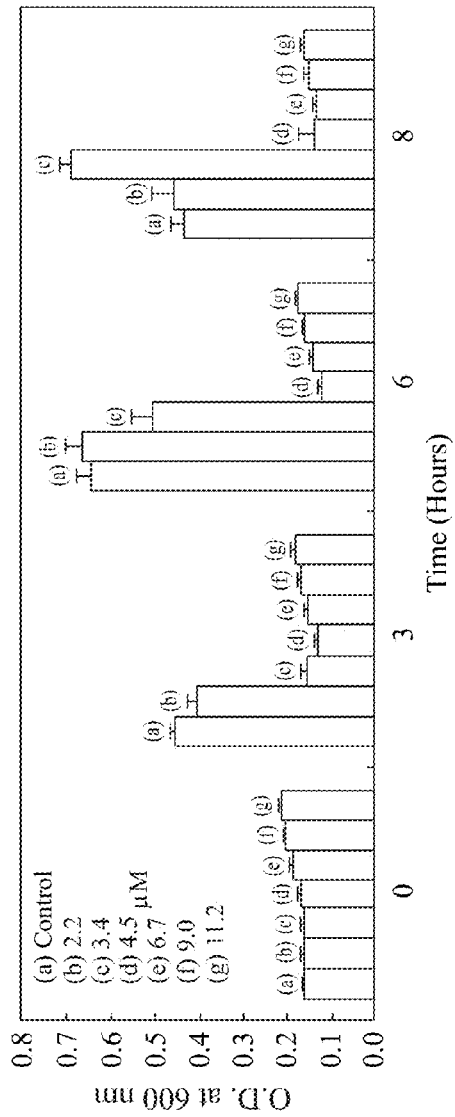
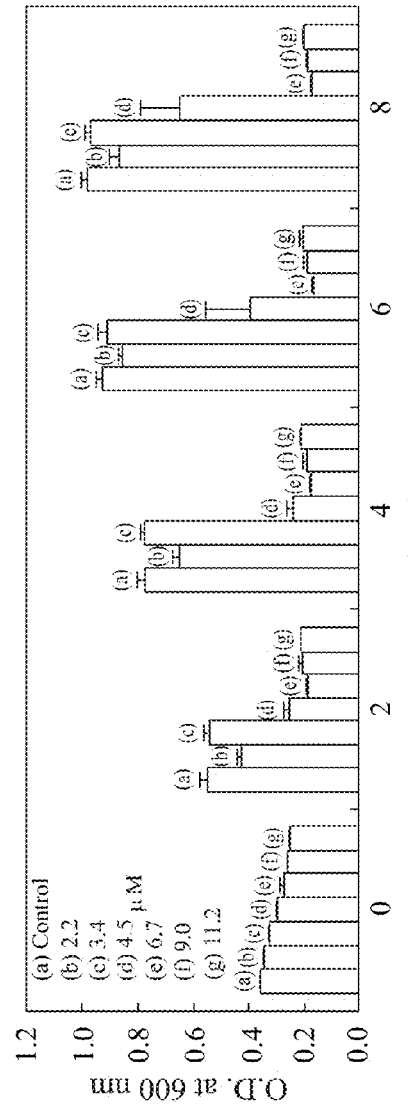
FIG. 6A
FIG. 6B

ANTIMICROBIAL POLYMERS AND METHODS OF MANUFACTURE THEREOF

CROSS REFERENCE TO RELATED APPLICATIONS

This application is a division of, and claims the benefit of, pending nonprovisional U.S. application Ser. No. 12/646,071 entitled "ANTIMICROBIAL POLYMERS AND METHODS OF MANUFACTURE THEREOF" filed on Dec. 23, 2009, herein incorporated by reference in its entirety.

BACKGROUND

The present invention relates to antimicrobial polymers, and more specifically, to biodegradable cationic block copolymers prepared by ring opening polymerization and methods of their use for antimicrobial applications.

Due to the increasing resistance of bacteria to conventional antibiotics, peptide-based macromolecular antimicrobial agents have received significant attention. Most conventional antibiotics (e.g., ciprofloxacin, doxycycline and ceftazidime) do not physically damage the cell wall but penetrate into the target microorganism and act on specific targets. The antibiotic can, for example, cause breakage of double-stranded DNA by inhibition of DNA gyrase, block cell division, or trigger intrinsic autolysins. As a consequence, the bacterial morphology is preserved and the bacteria can easily develop resistance. In contrast, most cationic peptides (e.g., magainins, cecropins, protegrins and defensins) do not have a specific target in microbes. Instead, they interact with microbial membranes based on electrostatic interaction, thereby inducing damage to the microbial membranes which is hard to repair. It has been proven that the macromolecular cationic antimicrobial peptides can overcome bacterial resistance. The disintegration of cell membrane eventually leads to cell death. Although efforts have been made to design peptides with various structures over the last two decades, these materials have had limited success in clinical trials. To date, only four cationic peptides have successfully entered Phase III clinical trials for wound healing. This is mainly due to cytotoxicity caused by the cationic nature of peptides (e.g., hemolysis), short half-life in vivo (labile to proteases) and high manufacturing cost.

A number of cationic block copolymers that mimic the facially amphiphilic structure and antimicrobial functionalities of peptides have been proposed because they can be more easily prepared and the synthesis can be more readily scaled up when compared to peptides. For example, antimicrobial polynorbornene and polyacrylate derivatives, poly(arylamide), poly(beta-lactam), and pyridinium copolymers were synthesized. However, these antimicrobial polymers are non-biodegradable, which can limit their in vivo applications.

Consequently, a continuing need exists for biodegradable cationic block copolymers having low cytotoxicity and that form nano-size micelles having low CMC suitable for antimicrobial applications.

SUMMARY

Accordingly, amphiphilic biodegradable block copolymers are disclosed that self-assemble into cationic micelles in water. The block copolymers contain a cationic hydrophilic block and a hydrophobic block. The formation of nanostructures in aqueous solution before contact with a cell surface is believed to increase the local concentration of cationic charge and polymer mass, leading to enhanced interaction with negatively charged cell walls, and thus stronger antimicrobial activity.

In an embodiment, a biodegradable cationic block copolymer comprises:

a hydrophilic block comprising first repeat units derived from a first cyclic carbonyl monomer by ring-opening polymerization, wherein more than 0% of the first repeat units comprise a side chain moiety comprising a quaternary amine group;

a hydrophobic block comprising second repeat units derived from a second cyclic carbonyl monomer by ring-opening polymerization;

an optional endcap group; and a chain fragment derived from a dinucleophilic initiator of the general formula (10):

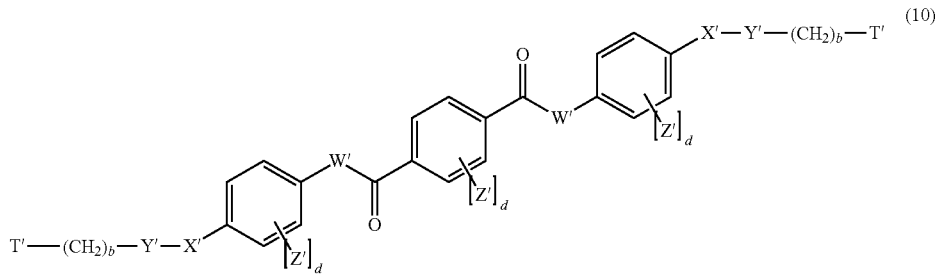

wherein each X' and each W' is independently a single bond or a divalent radical selected from the group consisting of $-(CR'_2)_c-$, $-O-$, $-S-$, $-NR'-$, and $-NR'(CR'_2)_c-$; each c is independently an integer from 1 to 5; R' is a monovalent radical selected from the group consisting of hydrogen, alkyl groups comprising 1 to 30 carbons, and aryl groups comprising 6 to 30 carbons; each Y' is independently a single bond or a divalent radical selected from the group consisting of $-CO-$ (carbonyl), $-NR'CO-$ (aminocarbonyl), $-COO-$ (oxycarbonyl), $-SCO-$ (thiocarbonyl); each T' is a monovalent nucleophile independently selected from the group consisting of $-OH$, $-SH$, $-NH_2$, and $-NR^dH$, wherein $R^d$ is a monovalent radical selected from the group consisting of hydrogen, alkyl groups comprising 1 to 30 carbons, and aryl groups comprising 6 to 30 carbons; each Z' is a monovalent radical independently selected from the group consisting of halides, alkyl groups comprising 1 to 20 carbons, alkoxy groups comprising 1 to 20 carbons, and aryl groups comprising 6 to 20 carbons; each b is an integer independently from 1 to 20; and each d is independently 0 or an integer from 1 to 4;

wherein the cationic block copolymer biodegrades 60% within 180 days in accordance with ASTM D6400.

In another embodiment, a method of forming a biodegradable cationic block copolymer is disclosed, comprising:

forming a reaction mixture comprising an organocatalyst, an accelerator, an optional solvent, and a dinucleophilic initiator of the general formula (10):

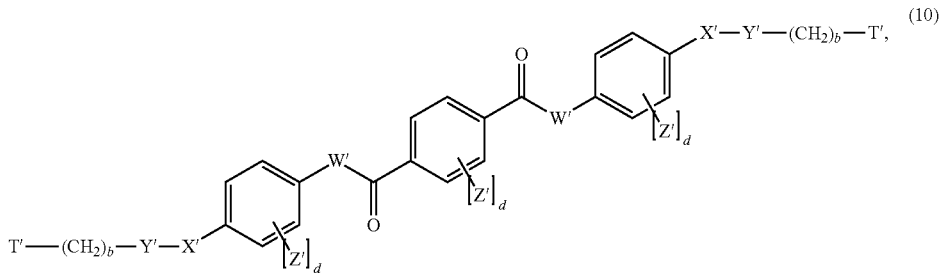

wherein each X' and each W' is independently a single bond or a divalent radical selected from the group consisting of —(CR'$_2$)$_c$—, —O—, —S—, —NR'—, and —NR'(CR'$_2$)$_c$—, each c is independently an integer from 1 to 5, R' is a monovalent radical selected from the group consisting of hydrogen, alkyl groups comprising 1 to 30 carbons, and aryl groups comprising 6 to 30 carbons, each Y' is independently a single bond or a divalent radical selected from the group consisting of —CO— (carbonyl), —NR'CO— (aminocarbonyl), —COO— (oxycarbonyl), —SCO— (thiocarbonyl), each T' is a monovalent nucleophile independently selected from the group consisting of —OH, —SH, —NH$_2$, and —NR$^d$H, wherein R$^d$ is a monovalent radical selected from the group consisting of hydrogen, alkyl groups comprising 1 to 30 carbons, and aryl groups comprising 6 to 30 carbons, each Z' is a monovalent radical independently selected from the group consisting of halides, alkyl groups comprising 1 to 20 carbons, alkoxy groups comprising 1 to 20 carbons, and aryl groups comprising 6 to 20 carbons, each b is an integer independently from 1 to 20, and each d is independently 0 or an integer from 1 to 4;

sequentially adding to the reaction mixture and reacting by ring-opening polymerization a first cyclic carbonyl monomer followed by a second cyclic carbonyl monomer, thereby forming a first block copolymer, wherein the first cyclic carbonyl monomer comprises a monovalent leaving group capable of reacting with a tertiary amine to form a quaternary amine, and the second cyclic carbonyl monomer is not capable of reacting with the tertiary amine to form any quaternary amine, and wherein the first block copolymer comprises a chain fragment comprising two or more backbone aromatic rings derived from the dinucleophilic initiator;

optionally endcapping the first block copolymer, thereby forming a precursor block copolymer; and treating the precursor block copolymer with a tertiary amine to form the cationic block copolymer;

wherein the cationic block copolymer comprises first repeat units derived from the first cyclic carbonyl monomer, more than 0% of the first repeat units comprise a side chain moiety comprising the quaternary amine, and the cationic block copolymer biodegrades 60% within 180 days in accordance with ASTM D6400.

In another embodiment, an aqueous micelle mixture is disclosed, comprising:

about 5 to 500 micrograms/mL of a biodegradable cationic block copolymer; wherein the cationic block copolymer comprises:

a hydrophilic block comprising first repeat units derived from a first cyclic carbonyl monomer by ring-opening polymerization, wherein more than 0% of the first repeat units comprise a side chain moiety comprising a quaternary amine group;

a hydrophobic block comprising second repeat units derived from a second cyclic carbonyl monomer by ring-opening polymerization;

a chain fragment derived from an initiator for the ring opening polymerization, and an optional endcap group;

wherein the aqueous micelle mixture induces lysis of a microbial cell membrane, and the cationic block copolymer biodegrades 60% within 180 days in accordance with ASTM D6400.

A method of forming an aqueous micelle mixture is disclosed, comprising:

mixing with agitation, at a pH of from 5.0 to 8.0 and at a concentration of 5 to 500 micrograms/mL or more, a biodegradable cationic block copolymer in an aqueous solution, thereby forming an aqueous micelle mixture;

wherein the aqueous micelles have an average particle size of 10 to 500 nm, and the cationic block copolymer comprises a hydrophilic block comprising first repeat units derived from a first cyclic carbonyl monomer by ring-opening polymerization, wherein more than 0% of the first repeat units comprise a side chain moiety comprising a quaternary amine group, a hydrophobic block comprising second repeat units derived from a second cyclic carbonyl monomer by ring-opening polymerization, a chain fragment derived from an initiator for the ring opening polymerization, and an optional endcap group; and wherein the aqueous micelle mixture induces lysis of a microbial cell membrane, and the cationic block copolymer biodegrades 60% within 180 days in accordance with ASTM D6400.

A method of treating a microbe is disclosed, comprising:

contacting a cell membrane of the microbe with an aqueous micelle mixture comprising a biodegradable cationic block copolymer at a pH of from 5.0 to 8.0 and at a concentration effective in inducing lysis of the cell membrane;

wherein the block copolymer comprises: a hydrophilic block comprising first repeat units derived from a first cyclic carbonyl monomer by ring-opening polymerization, wherein more than 0% of the first repeat units comprise a side chain moiety comprising a quaternary amine group; a hydrophobic block comprising second repeat units derived from a second cyclic carbonyl monomer by ring-opening polymerization; a chain fragment derived from an initiator for the ring opening polymerization, and an optional endcap group; and wherein the cationic block copolymer biodegrades 60% within 180 days in accordance with ASTM D6400.

BRIEF DESCRIPTION OF THE SEVERAL VIEWS OF THE DRAWINGS

FIGS. 6A to 6E are bar charts showing the viability of Gram-positive bacteria *Bacillus subtilis, Staphylococcus aureus*, methicillin-resistant *Staphylococcus aureus*, the fungus *Cryptococcus neoformans*, and the Gram-positive bacterium *Enterococcus faecalis*, respectively, when treated with micelles formed from Example 3.

DETAILED DESCRIPTION

Figure 1A:
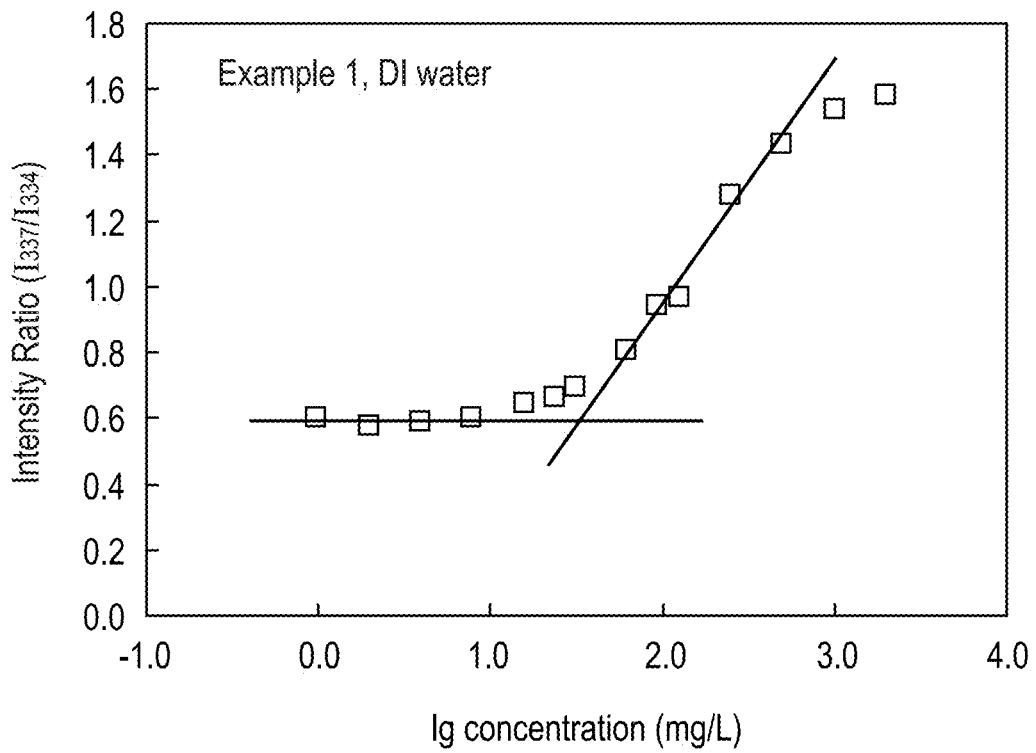
FIGS. 1A and 1B are graphs plotting $I_{337}/I_{334}$ ratio as a function of logarithm of polymer concentration (1 g C, mg/L) used in determining the CMC of the cationic block copolymer of Example 1 in de-ionized water and tryptic soy broth (medium for growth of bacteria), respectively.

Biodegradable cationic block polymers are disclosed that form stable nano-sized micelles having useful antimicrobial properties. The cationic block copolymers are derived by ring-opening polymerization (ROP) of a cyclic carbonyl monomer having a leaving group, such as an alkyl halide or a sulphonate ester, which is capable of reacting with a tertiary amine to form a moiety comprising a quaternary amine. Other cyclic carbonyl monomers are selected as diluents for the former, to provide hydrophobicity and thereby modulate the amphiphilic properties of the block polymers. The cationic block polymers can be densely charged and thus freely soluble in water, or possess amphiphilic properties suitable for forming nanoparticulate micelles in aqueous solution. The micelles can be spherical or rod-like depending on the rigidity, or shape persistence, of the initiator for the ring-opening polymerization. The initiator becomes a chain fragment attached at an end of as many ROP chains as nucleophilic sites on the initiator. The ring-opening method allows precise control of the molecular weight of the cationic block copolymer, achieves a narrow polydispersity, and is compatible with a variety of functional groups. The reaction with the tertiary amine to form the moiety comprising a quaternary amine can be performed before or after the ring-opening polymerization, more particularly after the polymerization. The quaternization is accompanied by minimal, if any, crosslinking of the cationic block copolymer, or change in the average molecular weight. Examples of cyclic carbonyl monomers include cyclic carbonate monomers and lactones, including lactides, that ring open to form polymers comprising carbonate and ester repeat units, respectively. The quaternary amine is located on the polymer side chain, and if desired can be linked directly to the polymer backbone. The positively charged quaternary amine groups provide binding strength to negatively charged microbe surfaces. The polymers can comprise other functional groups, such as secondary amine groups, citraconic amide groups, ester groups, and imine groups that can be used to facilitate interaction of the micelles with the microbial surface and/or permeation of the micelles into the cell membrane. The cationic block copolymers can be linear or branched, and can be easily modified on the side chains and end groups to tune the charge and/or the buffering strength of the pendant functional groups. The micelles have an average particle size of about 10 nm to about 500 nm.

The term "biodegradable" is defined by the American Society for Testing and Materials as a degradation caused by biological activity, especially by enzymatic action, leading to a significant change in the chemical structure of the material. For purposes herein, a material is biodegradable if it undergoes 60% biodegradation within 180 days in accordance with ASTM D6400.

The micelles prepared from the cationic block copolymers can be used alone for antimicrobial treatments. Alternatively, the micelles can be loaded with a biologically active material (also referred to herein as a "cargo"). The biologically active material can be encapsulated into the nano-sized micelles through non-covalent bonding, and does not interfere with the antimicrobial function of the cationic block copolymer (i.e., lysis of the microbial cell membrane). The biologically active material can be released from the loaded micelle while circulating in the blood stream, thereby allowing the biologically active material to enter cells itself to affect a biological function, unaccompanied by the cationic block copolymer. Biologically active materials include biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. "Biologically active" means the substance can alter the chemical structure and/or activity of a cell in a desirable manner, or can selectively alter the chemical structure and/or activity of a cell type relative to another cell type in a desirable manner. As an example, one desirable change in a chemical structure can be the incorporation of a gene into the cell. A desirable change in activity can be the expression of a transfected gene. Another change in cell activity can be the induced production of a desired hormone or enzyme. Alternatively, a desirable change in activity can be the selective death of one cell type over another cell type. That is, the biologically active material and the cationic block copolymers can induce cell death by different mechanisms and in different cell types. No limitation is placed on the relative change in cellular activity caused by the biologically active material, providing the change is desirable and useful, and providing the antimicrobial properties of the cationic block copolymer are not adversely affected. Moreover, no limitation is placed on the so-called cargo, providing the cargo induces a useful cellular response when released from the micelles. More particularly, the biologically active material is not negatively charged. In an embodiment, the biologically active material is selected from the group consisting of peptides, drugs, and combinations thereof.

In the following description of general formulas for cyclic carbonyl monomers, a "first cyclic carbonyl monomer" refers to a first category of cyclic carbonyl monomers comprising a functional leaving group capable of reacting with a tertiary amine to form a moiety comprising a quaternary amine. The term "second cyclic carbonyl monomer" refers to a second category of cyclic carbonyl monomer that contains no leaving group capable of reacting with the tertiary amine to form a moiety comprising any quaternary amine. Otherwise, the first and second cyclic carbonyl monomers can have a structure selected from any of the following described formulas.

The micelle forming block copolymers described below are named according to general formula (1):

$$A'-[P(Monomer1, \ldots)]_w \qquad (1)$$

where A' represents an initiator having w nucleophilic sites, and [P(Monomer1, ...)] represents a ROP polymer formed by ring opening polymerization of one or more cyclic carbonyl monomers. The "P( )" indicates ring opening polymerization of the one or more cyclic carbonyl monomers contained within the parentheses. [P(Monomer1, ...)] can comprise a polymer chain comprising a homopolymer formed from a single cyclic carbonyl monomer, a random copolymer formed from two or more cyclic carbonyl monomers (indicated by "-r-" separating the monomer names in formula (1)), a block copolymer formed from two or more cyclic carbonyl monomers (indicated by "-b-" separating the two or more cyclic carbonyl monomers), or a mixture of thereof. That is, [P(Monomer1, ...)] can itself comprise any one of, or a mixture of, these polymer chain types.

For example, the block copolymer prepared from MTCOPrCl and TMC, initiated by the monomeric diol BnMPA, is represented as BnMPA-[P(MTCOPrCl)-b-P(TMC)]$_2$. As shown below, the polymer is not endcapped. In the reaction below, m and n represent moles of MTCOPrCl and TMC, respectively.

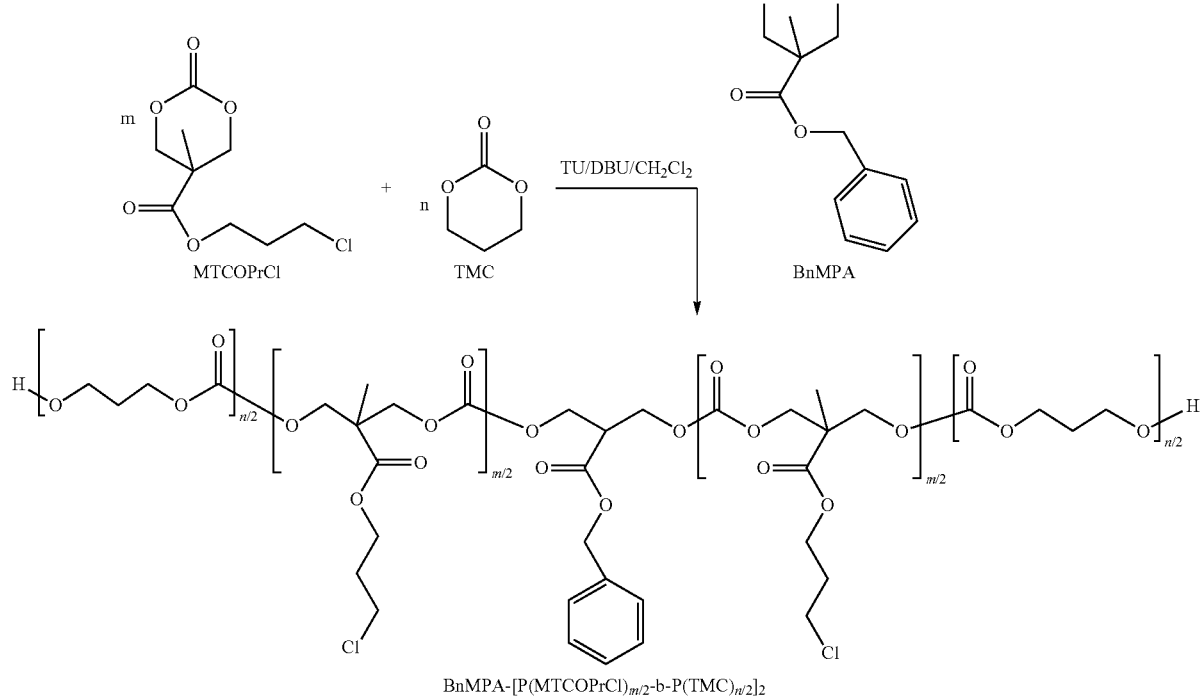

The cyclic carbonyl monomers can be selected independently from compounds of the general formula (2):

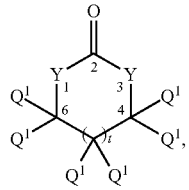

(2)

wherein t is an integer from 0 to 6, and when t is 0 carbons labeled 4 and 6 are linked together by a single bond. Each Y is a divalent radical independently selected from —O—, —S—,

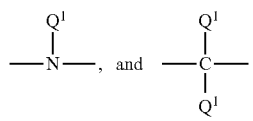

where the dash "—" indicates the point of attachment. The latter two groups are also expressed herein as —N(Q$^1$)- and —C(Q$^1$)$_2$-. Each Q$^1$ is a monovalent radical independently selected from the group consisting of hydrogen, carboxy groups, halides, alkyl groups comprising 1 to 30 carbons, aryl groups comprising 6 to 30 carbon atoms, and groups having the structure

wherein M$^1$ is a monovalent radical selected from —R$^1$, —OR$^1$, —NHR$^1$, —NR$^1$R$^1$, or —SR$^1$, wherein the dash indicates the point of attachment. Each R$^1$ is a monovalent radical independently selected from the group consisting of alkyl groups comprising 1 to 30 carbons, and aryl groups comprising 6 to 30 carbons. One or more Q$^1$ groups can further comprise a monovalent leaving group capable of reacting with a tertiary amine to form a moiety comprising a quaternary amine (i.e., a positively charged quaternary ammonium ion bonded to four carbons). Non-limiting examples of monovalent leaving groups include halides in the form of alkyl halides (e.g., alkyl chloride, alkyl bromide, or alkyl iodide), sulphonate esters (e.g., tosylate or mesylate esters), and epoxides. Each Q$^1$ group can independently be branched or non-branched. Each Q$^1$ group can also independently comprise additional functional groups selected from the group consisting of ketone groups, aldehyde groups, alkene groups, alkyne groups, cycloaliphatic rings comprising 3 to 10 carbons, heterocylic rings comprising 2 to 10 carbons, ether groups, amide groups, ester groups, and combinations of the foregoing additional functional groups. The heterocyclic ring can comprise oxygen, sulfur and/or nitrogen. Two or more Q$^1$ groups can together form a ring. A first cyclic carbonyl monomer of formula (2) comprises a Q$^1$ group comprising a monovalent leaving group capable of reacting with a tertiary amine to form a moiety comprising a quaternary amine. A second cyclic carbonyl monomer of formula (2) comprises no functional group capable of reacting with the tertiary amine to form a moiety comprising any quaternary amine.

A more specific cyclic carbonyl monomer capable of ring-opening polymerization has the general formula (3):

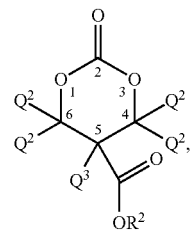

(3)

wherein Q$^2$ is a monovalent radical independently selected from the group consisting of hydrogen, halides, carboxy groups, alkyl groups comprising 1 to 30 carbons, aryl groups comprising 6 to 30 carbon atoms, and groups having the structure

wherein M$^1$ is a monovalent radical selected from the group consisting of —R$^1$, —OR$^1$, —NHR$^1$, —NR$^1$R$^1$, and —SR$^1$, wherein the dash indicates the point of attachment. Each R$^1$ is a monovalent radical independently selected from the group consisting of alkyl groups comprising 1 to 30 carbons, and aryl groups comprising 6 to 30 carbons; R$^2$ is a monovalent radical independently selected from the group consisting of alkyl groups comprising 1 to 30 carbons, and aryl groups comprising 6 to 30 carbons; and Q$^3$ is a monovalent group selected from the group consisting of hydrogen, alkyl groups having 1 to 30 carbons, and aryl groups having 6 to 30 carbons. In an embodiment, each Q$^2$ is hydrogen, Q$^3$ is a methyl or ethyl group, and R$^2$ is an alkyl group comprising 1 to 30 carbons. A first cyclic carbonyl monomer of formula (3) comprises an R$^2$ group comprising a monovalent leaving group capable of reacting with a tertiary amine to form a moiety comprising a quaternary amine. A second cyclic carbonyl monomer of formula (3) comprises no functional group capable of reacting with the tertiary amine to form a moiety comprising any quaternary amine.

Another more specific cyclic carbonyl monomer has the general formula (4):

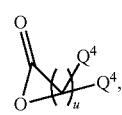

(4)

wherein u is an integer from 1 to 8, each Q$^4$ is a monovalent radical independently selected from the group consisting of hydrogen, halides, carboxy groups, alkyl groups comprising 1 to 30 carbons, aryl groups comprising 6 to 30 carbon atoms, and groups having the structure

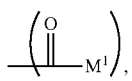

wherein $M^1$ is a monovalent radical selected from the group consisting of —$R^1$, —$OR^1$, —$NHR^1$, —$NR^1R^1$, or —$SR^1$, wherein the dash indicates the point of attachment. Each $R^1$ is a monovalent radical independently selected from the group consisting of alkyl groups comprising 1 to 30 carbons, and aryl groups comprising 6 to 30 carbons. The lactone ring can optionally comprise a carbon-carbon double bond; that is, optionally, a

group of formula (4) can independently represent a

group. The lactone ring can also comprise a heteroatom such as oxygen, nitrogen, sulfur, or a combination thereof; that is, optionally a

group of formula (4) can independently represent a —O—, —S—, —$NHR^1$, or an —$NR^1R^1$ group, wherein the dash indicates the point of attachment and each $R^1$ is a monovalent radical independently selected from the group consisting of alkyl groups comprising 1 to 30 carbons, and aryl groups comprising 6 to 30 carbons. A first cyclic carbonyl monomer of formula (4) comprises a $Q^4$ group comprising a monovalent leaving group capable of reacting with a tertiary amine to form a moiety comprising a quaternary amine. A second cyclic carbonyl monomer of formula (4) comprises no functional group capable of reacting with the tertiary amine to form a moiety comprising any quaternary amine. In an embodiment, u is an integer from 1 to 6 and each $Q^4$ is hydrogen.

Another more specific cyclic carbonyl monomer is a dioxane dicarbonyl of the general formula (5):

(5)

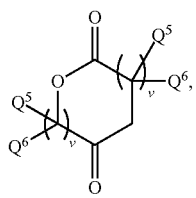

wherein each v is independently an integer from 1 to 6; each $Q^5$ is a monovalent radical independently selected from the group consisting of hydrogen, halides, carboxy groups, alkyl groups comprising 1 to 30 carbons, aryl groups comprising 6 to 30 carbon atoms, and groups having the structure

where $M^1$ is a monovalent radical selected from —$R^1$, —$OR^1$, —$NHR^1$, —$NR^1R^1$, or —$SR^1$, wherein the dash indicates the point of attachment. Each $R^1$ is a monovalent radical independently selected from the group consisting of alkyl groups comprising 1 to 30 carbons, and aryl groups comprising 6 to 30 carbons; each $Q^6$ is a monovalent group independently selected from the group consisting of hydrogen, alkyl groups having 1 to 30 carbons, and aryl groups having 6 to 30 carbons. A first cyclic carbonyl monomer of formula (5) comprises a $Q^5$ group and/or a $Q^6$ group comprising a monovalent leaving group capable of reacting with a tertiary amine to form a moiety comprising a quaternary amine. A second cyclic carbonyl monomer of formula (5) comprises no functional group capable of reacting with the tertiary amine to form a moiety comprising any quaternary amine. In an embodiment, each v is 1, each $Q^5$ is hydrogen, and each $Q^6$ is an alkyl group comprising 1 to 6 carbons.

The cyclic carbonyl compounds can have one or more asymmetric carbon centers that can be present in isomerically enriched form, either as an R-isomer or an S-isomer. Further, each asymmetric carbon center can independently be present in an enantiomeric excess of 80% or more, more specifically 90% or more.

Examples of cyclic carbonyl monomers of formulas (2) or (3) having a monovalent leaving group in the form of an alkyl halide include the cyclic monomers of Table 1.

TABLE 1

| (MTCOPrCl) | (MTCOPrBr) |
|---|---|
| (MTCOEtI) | |

Additional examples of cyclic carbonyl monomers of formula (3) include the compounds of Table 2. These can be used, for example, as co-monomers in the ring-opening polymerization of the halide monomers of Table 1, to form random copolymers or block copolymers.

TABLE 2
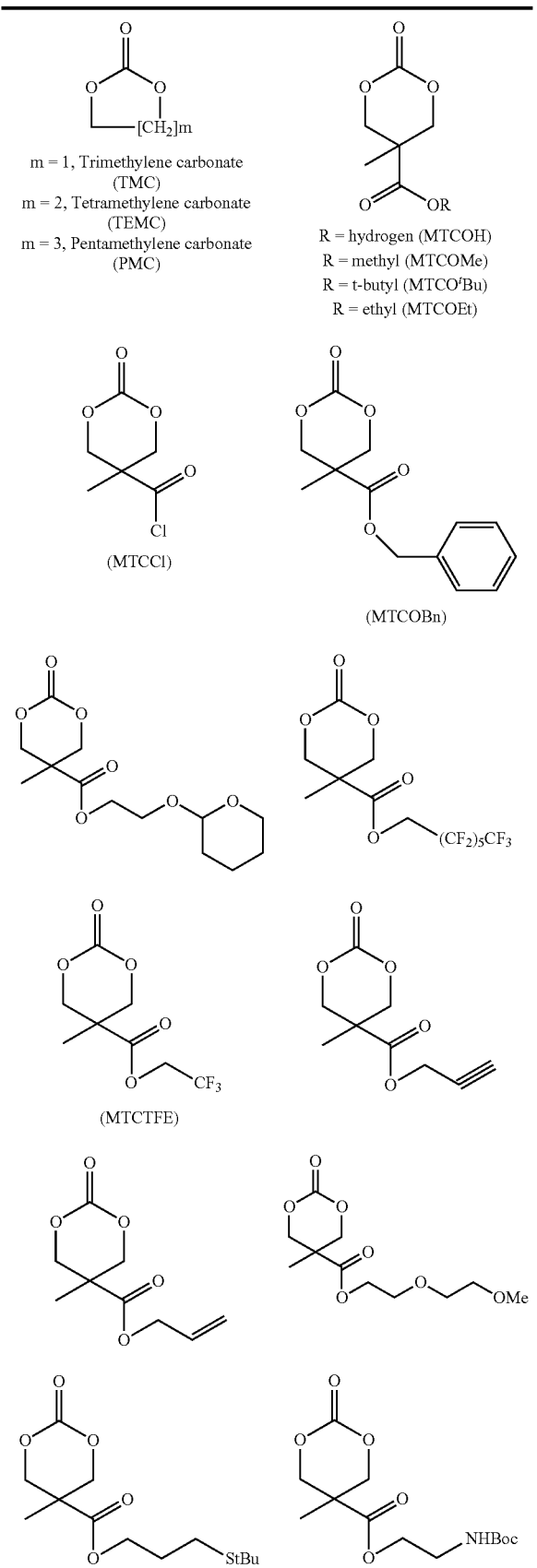
TABLE 2-continued
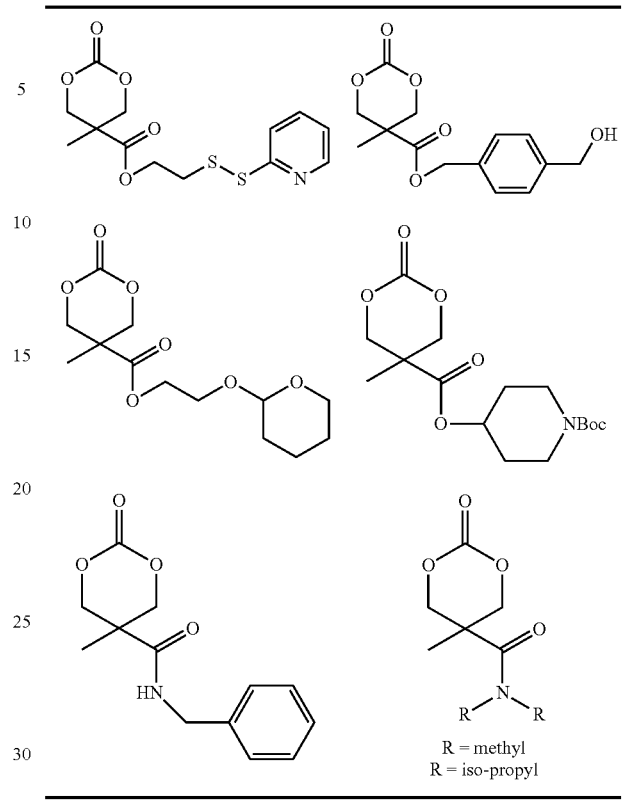
Examples of cyclic carbonyl monomers of formula (4) include the compounds of Table 3.
TABLE 3
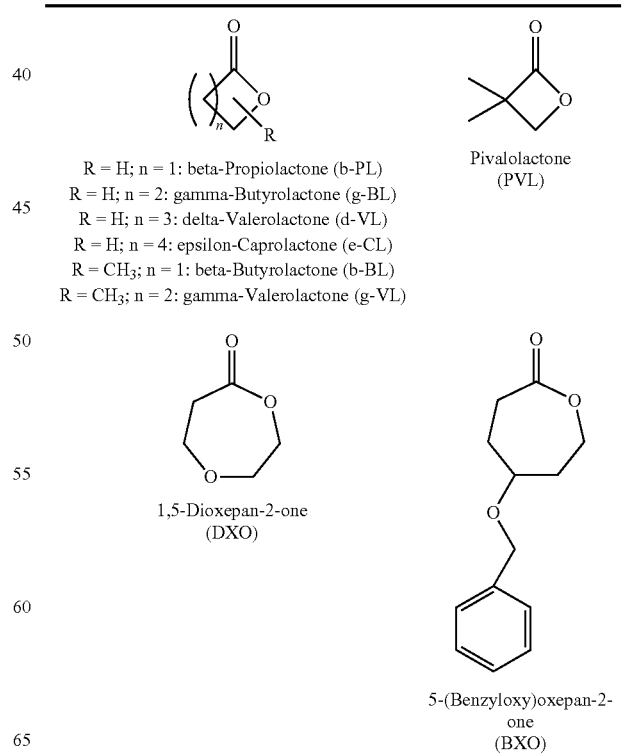

TABLE 3-continued

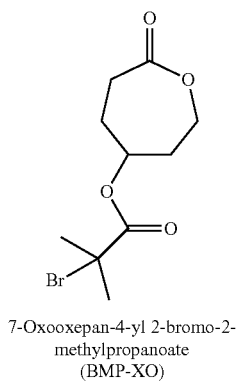

7-Oxooxepan-4-yl 2-bromo-2-methylpropanoate (BMP-XO)

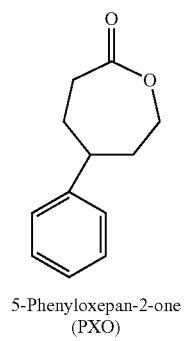

5-Phenyloxepan-2-one (PXO)

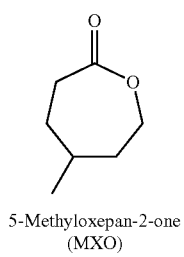

5-Methyloxepan-2-one (MXO)

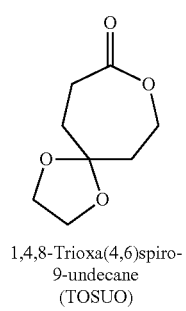

1,4,8-Trioxa(4,6)spiro-9-undecane (TOSUO)

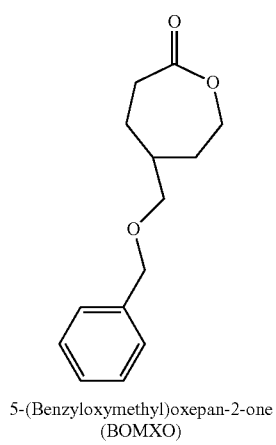

5-(Benzyloxymethyl)oxepan-2-one (BOMXO)

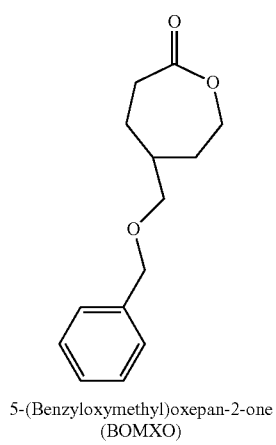

7-Oxooxepan-4-yl 3-hydroxy-2-(hydroxymethyl)-2-methylpropanoate (OX-BHMP)

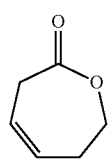

(Z)-6,7-Dihydrooxepin-2(3H)-one (DHXO)

Examples of cyclic carbonyl monomers of formula (5) include the compounds of Table 4.

TABLE 4

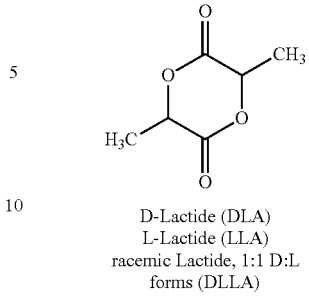

D-Lactide (DLA)
L-Lactide (LLA)
racemic Lactide, 1:1 D:L forms (DLLA)

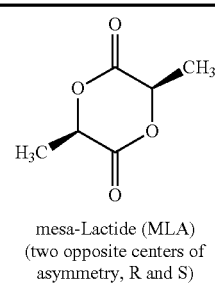

mesa-Lactide (MLA) (two opposite centers of asymmetry, R and S)

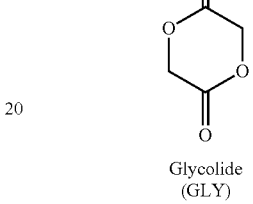

Glycolide (GLY)

The cationic block copolymer can comprise a pendant protected carboxylic acid that can be converted to a carboxylic acid at about pH 5, if desired. An example of a latent carboxylic acid group is an acetal-protected carboxylic acid group, herein also referred to as an acetal ester group. The acetal ester group has the general formula (6):

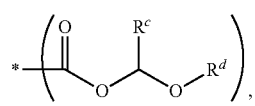

(6)

wherein * represents the bond to a cyclic carbonyl moiety, and $R^c$ and $R^d$ are monovalent radicals independently comprising 1 to 20 carbons. In an embodiment, $R^c$ is methyl and $R^d$ is ethyl. A more specific example of cyclic carbonyl compound having a latent carboxylic acid group is MTCOEE:

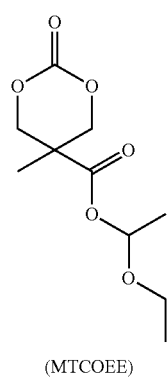 [SMILES: CCOC(C)OC(=O)C1(C)COC(=O)OC1]

(MTCOEE)

When copolymerized into the cationic block copolymer, repeat units derived from MTCOEE comprise a side chain acetal ester that is readily deprotected under mildly acidic conditions. In this manner the hydrophobic properties of the cationic block polymer can be tuned for a specific pH environment.

A strategy for modulating non-covalent interactions of the cationic block copolymer with, for example, a biologically active cargo, is to use a cyclic carbonyl monomer comprising a fluorinated tertiary alcohol group. Fluorinated tertiary alcohol groups are known to bind to phosphates and related structures, but with interaction energies that are lower than electrostatic interactions, and hence more easily released.

The above monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The above-described cyclic carbonyl monomers, at least one of which comprises a leaving group capable of reacting with the tertiary amine, undergoes ring-opening polymerization to form a first polymer. The first polymer is a living polymer capable of initiating chain growth with the same or a different cyclic carbonyl monomer, or a mixture of cyclic carbonyl monomers, to form a block copolymer. The first polymer can optionally be treated with an endcapping agent to prevent further chain growth and to stabilize the reactive end groups. The resulting precursor block copolymer is then treated with a tertiary amine to form the cationic block copolymer. The first polymer, the precursor block copolymer, and the cationic block copolymer can be produced in atactic, syndiotactic or isotactic forms. The particular tacticity depends on the cyclic monomer(s), isomeric purity, and the reaction conditions.

Alternatively, the cationic block copolymer can be obtained by ring-opening polymerization of a cyclic carbonyl monomer comprising a quaternary amine group. However, these monomers are more difficult to prepare, are less stable, and the corresponding polymers tend to be more polydisperse. Therefore, the quaternization reaction is preferably performed after the ring-opening polymerization.

The first polymer can be a homopolymer prepared from a reaction mixture comprising a first cyclic carbonyl monomer, a catalyst, an accelerator, an initiator, and an optional solvent. The first cyclic monomer comprises a leaving group capable of reacting with the tertiary amine to form a moiety comprising a quaternary amine. The ring-opening polymerization is generally conducted in a reactor under inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from about ambient temperature to 250° C. Generally, the reaction mixture is heated at atmospheric pressure for 0.5 to 72 hours to effect polymerization, forming a second mixture comprising the first polymer. A chain fragment derived from the initiator is attached at one end of the first polymer. If the initiator is a dinucleophilic initiator for the ring opening polymerization, the chain fragment derived from the initiator is attached at one end of each of two ROP chains, and so on. The first polymer is then optionally endcapped to form a precursor block copolymer. The precursor block copolymer is then treated with a tertiary amine to form the cationic block copolymer, wherein more than 0% of the repeat units derived from the first carbonyl monomer comprise a moiety comprising a quaternary amine.

The first polymer can also be a random copolymer formed by the copolymerization of, for example, a first cyclic carbonyl monomer and a second cyclic carbonyl monomer. The random first polymer is optionally endcapped to form a random precursor copolymer. In this case, the chain fragment derived from the initiator can be linked to a repeat unit derived from the first or second cyclic carbonyl monomer. The random precursor copolymer is then treated with a tertiary amine to form a random cationic copolymer, wherein more than 0% of the repeat units derived from the first cyclic carbonyl monomer comprise a moiety comprising a quaternary amine. The repeat units derived from the second cyclic carbonyl monomer do not react with any tertiary amine to form a quaternary amine. It is understood that the reaction mixture can include additional cyclic carbonyl monomers if desired, either of the first category or of the second category.

More particularly, the first polymer is a block copolymer, formed by the sequential ring-opening polymerization of, for example, a first cyclic carbonyl monomer and a second cyclic carbonyl monomer, to form a first block copolymer. The first block copolymer is then optionally endcapped to form a precursor block copolymer. The precursor block copolymer is then treated with a tertiary amine to form a cationic block copolymer, wherein more than 0% of the repeat units derived from the first cyclic carbonyl monomer comprise a moiety comprising a quaternary amine. As before, the repeat units derived from the first cyclic carbonyl monomer do not react with the tertiary amine. Depending on the order of the ring-opening polymerizations, the chain fragment derived from the initiator can be attached to either block of the cationic block copolymer. In one example, the first cyclic carbonyl monomer is polymerized first to form a first block of the block copolymer, and the second cyclic carbonyl monomer is polymerized second to form a second block of the block copolymer. In this example, the cationic block copolymer comprises a hydrophilic block derived from the first cyclic carbonyl monomer that is attached to the chain fragment derived from the initiator, and a hydrophobic block derived from the second carbonyl monomer that is linked to the hydrophilic block and the endcap group. In another example, the second cyclic carbonyl monomer is polymerized first, and the first cyclic carbonyl monomer is polymerized second. In this example, the cationic block copolymer comprises a hydrophobic block attached to the chain fragment derived from the initiator, and a hydrophilic block linked to the hydrophobic block and the endcap group. Additional blocks can be formed if desired before endcapping by sequentially polymerizing an additional cyclic carbonyl monomer of either category, or combinations thereof. More particularly, the block copolymers are amphiphilic, forming self-assembled nano-sized micelles in aqueous solution.

Exemplary catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexyl-thiourea (TU):

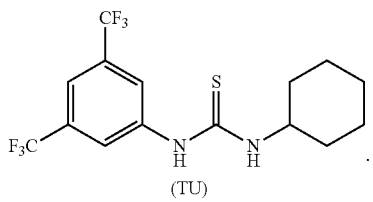

(TU)

In another embodiment, the catalyst and the accelerator are the same compound, such as 1,8-diazabicyclo[5.4.0]undec-7-ene (DBU).

Another metal-free ROP catalyst comprises at least one 1,1,1,3,3,3-hexafluoropropan-2-ol-2-yl (HFP) group. Singly-donating hydrogen bond catalysts have the formula (7):

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 5.

TABLE 5

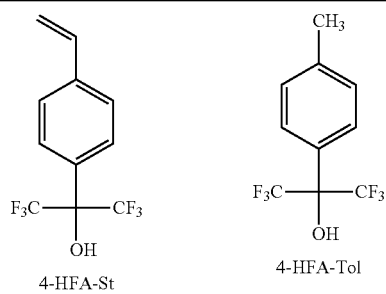

4-HFA-St

4-HFA-Tol

TABLE 5-continued

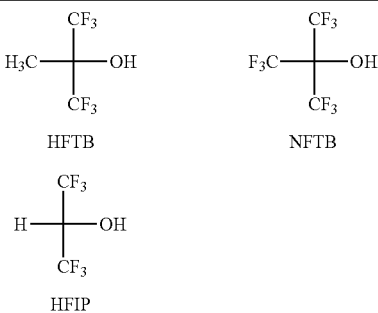

HFTB

NFTB

HFIP

Doubly-donating hydrogen bonding catalysts have two HFP groups, represented by the general formula (8):

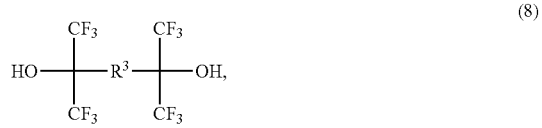

(8)

wherein $R^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (8) include those listed in Table 6. In a specific embodiment, $R^2$ is an arylene or substituted arylene group, and the HFP groups occupy positions meta to each other on the aromatic ring.

TABLE 6

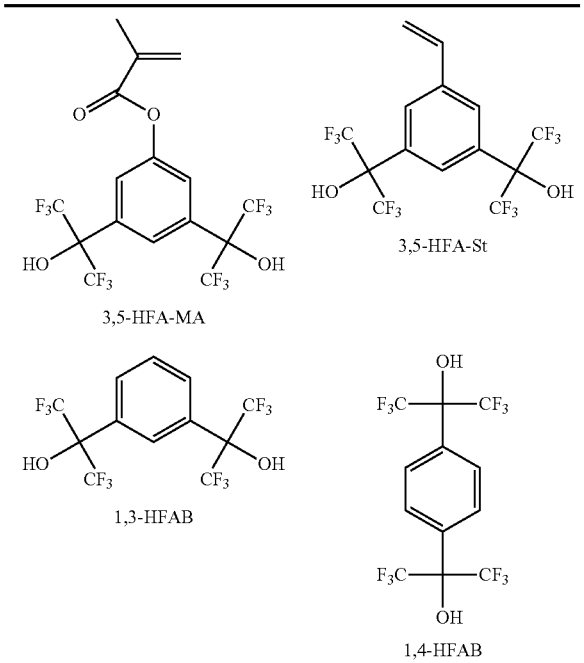

3,5-HFA-MA 3,5-HFA-St 1,3-HFAB 1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizable HFP-containing monomers may be found in: Ito et al., *Polym. Adv. Technol.* 2006, 17(2), 104-115, Ito et al., *Adv. Polym. Sci.* 2005, 172, 37-245, Ito et al., US20060292485, Maeda et al. WO2005098541, Allen et al. US20070254235, and Miyazawa et al. WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003, M. Delgado and K. D. Janda "Polymeric Supports for Solid Phase Organic Synthesis," *Curr. Org. Chem.* 2002, 6(12), 1031-1043, A. R. Vaino and K. D. Janda "Solid Phase Organic Synthesis: A Critical Understanding of the Resin", *J. Comb. Chem.* 2000, 2(6), 579-596, D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377, and T. J. Dickerson et al. "Soluble Polymers as Scaffold for Recoverable Catalysts and Reagents," *Chem. Rev.* 2002, 102(10), 3325-3343. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/1,000 to 1/20,000 moles. In an embodiment the catalyst is an organocatalyst.

The ring-opening polymerization is conducted in the presence of an accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl) imidazol-2-ylidene (Im-2), 1,3-bis(2,6-di-1-propylphenyl (imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis (2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 7.

TABLE 7

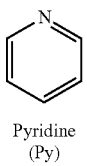
Pyridine
(Py)

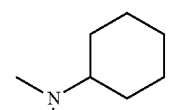
N,N-Dimethylaminocyclohexane
($Me_2NCy$)

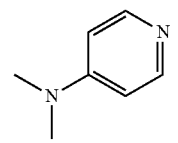
4-N,N-Dimethylaminopyridine
(DMAP)

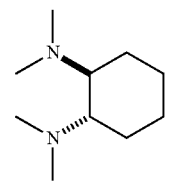
trans 1,2-Bis(dimethylamino)cyclohexane
(TMCHD)

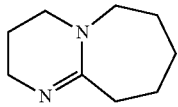
1,8-Diazabicyclo[5.4.0]undec-7-ene
(DBU)

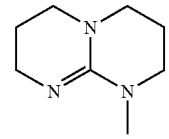
7-Methyl-1,5,7-triazabicyclo[4.4.0]dec-5-ene
(MTBD)

TABLE 7-continued

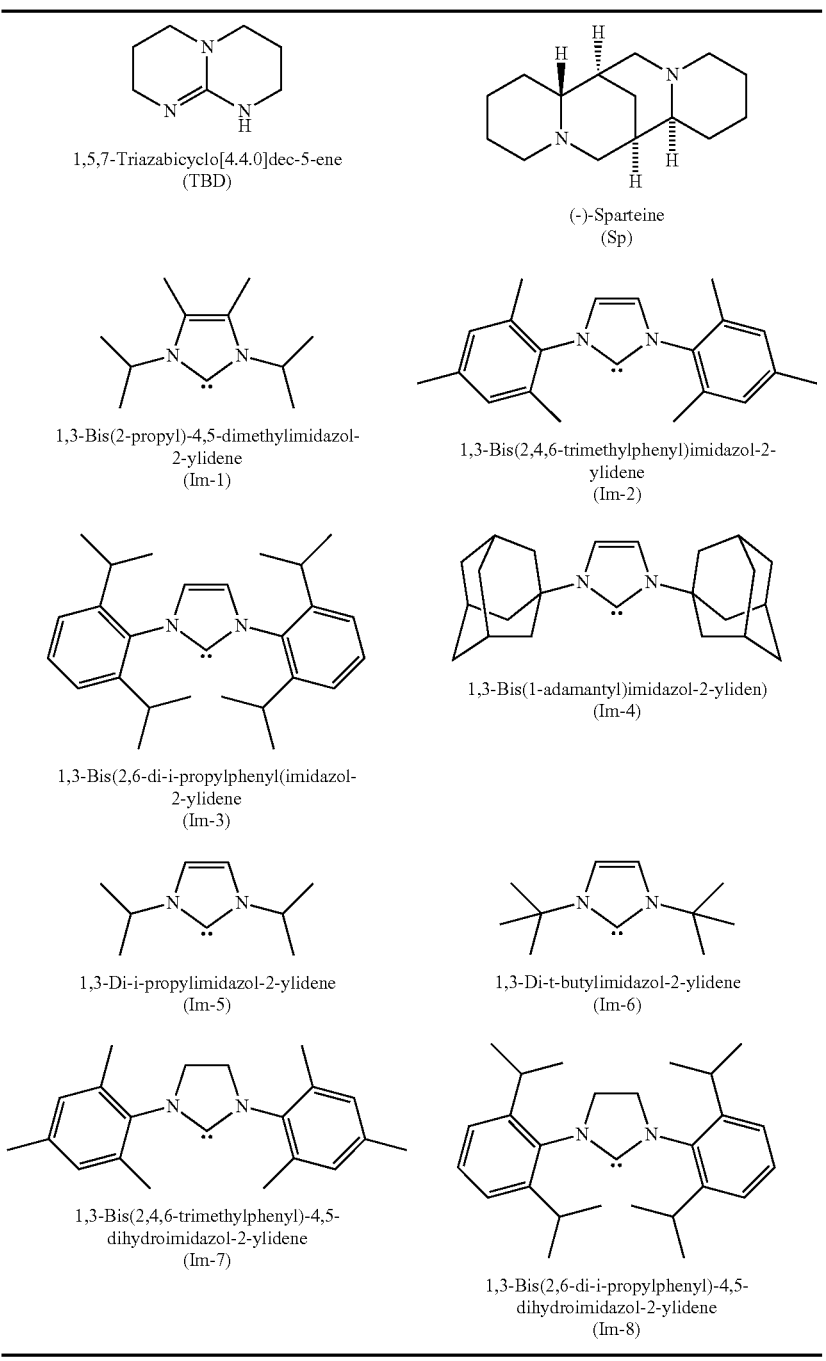

In one embodiment, the accelerator has two or three nitrogens, each capable of participating as a Lewis base, as for example in the structure (−)-sparteine. Stronger bases generally improve the polymerization rate.

The ROP reaction mixture also comprises an initiator. Initiators generally include nucleophiles such as alcohols, amines and thiols. In general, an antimicrobial cationic block copolymer can be formed using an initiator that is monofunctional, difunctional or multifunctional such as dendritic, polymeric or related architectures. Monofunctional initiators can include nucleophiles with protected functional groups that include thiols, amines, acids and alcohols. An alcohol initiator can be any suitable alcohol, including mono-alcohol, diol, triol, or other polyol, with the proviso that the choice of alcohol does not adversely affect the polymerization yield, polymer molecular weight, formation of a nanoparticulate stable micelle, complexation with a biologically active material, and/or the desirable mechanical and physical properties of the product polymer. The alcohol can also be multi-functional alcohol comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, or alcohol functionalized branched polymers derived from branched alcohols, or combinations thereof.

More particularly, the ROP initiator is a dinucleophilic initiator, and each nucleophilic group initiates ring opening polymerization to form a polymer chain of the cationic block copolymer. The cationic block copolymer can comprise as many polymer chains as nucleophilic groups of the initiator. That is, the cationic block copolymer can comprise two or more block copolymer chains, each linked to a nucleophilic group of the initiator. Each polymer chain can comprise blocks comprising a homopolymer or random copolymer formed by the ring opening polymerization. In an embodiment, the dinucleophilic initiator is a monomeric alkylene diol selected from the group consisting of ethylene glycols, propylene glycols, butylene glycols, pentylene glycols, hexylene glycols, and mixtures thereof. A more specific alkylene diol initiator is BnMPA, a precursor used in the preparation of cyclic carbonate monomers:

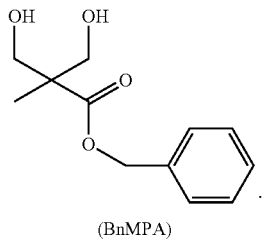 [SMILES: CC(CO)(CO)C(=O)OCc1ccccc1]

(BnMPA)

Even more particularly the ROP reaction mixture comprises a flexionally and or torsionally constrained dinucleophilic initiator that forms a rigid or semi-rigid chain fragment of the cationic block copolymer. The so-called rigid initiator can be monomeric, oligomeric, or polymeric. The rigid initiator comprises two or more aromatic rings that become backbone aromatic rings of the chain fragment, imparting flexional rigidity to the chain fragment. The rigid dinucleophilic initiator has the general formula (9):

wherein subscripts a and b are integers independently selected from 1 to 20, L' is a flexionally and/or torsionally constrained divalent radical, and each T' is a monovalent radical comprising a nucleophilic group independently selected from the group consisting of —OH, —SH, —NH$_2$, and —NR$^d$H, wherein the dash indicates the point of attachment to the methylene group of formula (9) (i.e., the dashes are not to be understood as carbons in —OH, —SH, —NH$_2$, and —NR$^d$H). R$^d$ is a monovalent radical selected from the group consisting of hydrogen, alkyl groups comprising 1 to 30 carbons, and aryl groups comprising 6 to 30 carbons. L' can comprise one or more, two or more, and more particularly three or more aromatic rings that become backbone units of the cationic block copolymer. The effect of the one or more aromatic rings that become backbone units is to induce flexional and/or torsional rigidity to L' compared to a hydrocarbon chain of similar length. Thus, L' has a length, and L' is less able to bend or fold in the lengthwise direction compared to the hydrocarbon chain. L' can have a flat, ribbon-like structure comprising planar aromatic groups, or L' can have a coiled structure that has short range flexional and torsional rigidity, for example by a combination of hydrogen bonding and steric interactions, such as in a DNA helix. In an embodiment, L' comprises three or more aromatic rings that become backbone units of the cationic block copolymer. In another embodiment, the micelle formed by the cationic block copolymer derived from the rigid dinucleophilic initiator has a nanoparticulate rod-like structure. In another embodiment, the micelle formed by the cationic block copolymer derived from a rigid dinucleophilic initiator does not form a spherical micelle.

More specifically, the rigid dinucleophilic initiator has the general formula (10):

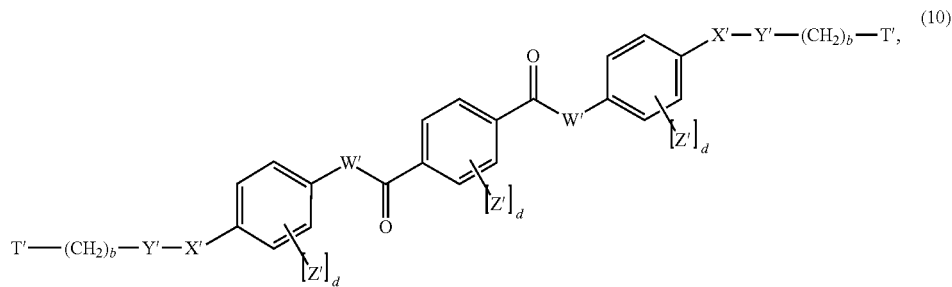

wherein each X' and each W' is independently a single bond or a divalent radical selected from the group consisting of —(CR'$_2$)$_c$—, —O—, —S—, —NR'—, and —NR'(CR'$_2$)$_c$—, wherein the dashes indicate the point of attachment, each c is independently an integer from 1 to 5, and R' is a monovalent radical selected from the group consisting of hydrogen, alkyl groups comprising 1 to 30 carbons, and aryl groups comprising 6 to 30 carbons. Each Y' can be a single bond or a divalent radical selected from the group consisting of —CO— (carbonyl), —NR'CO— (aminocarbonyl), —COO— (oxycarbonyl), —SCO— (thiocarbonyl), wherein the dashes indicate the point of attachment. Each T' is a monovalent nucleophilic group independently selected from the group consisting of —OH, —SH, —NH$_2$, and —NR$^d$H, wherein the dashes indicate the point of attachment, wherein R$^d$ is a monovalent radical selected from the group consisting of hydrogen, alkyl groups comprising 1 to 30 carbons, and aryl groups comprising 6 to 30 carbons. Each Z' is a monovalent radical independently selected from the group consisting of halides, alkyl groups comprising 1 to 20 carbons, alkoxy groups comprising 1 to 20 carbons, and aryl groups comprising 6 to 20 carbons. Each subscript b is independently an integer from 1 to 20; and each subscript d is independently 0 or an integer from 1 to 4. When d is zero the aromatic ring is understood to have four hydrogens attached to the aromatic ring.

Examples of rigid dinucleophilic initiators include the following diols, HPUBT and HPUPT.

The catalyst is present in an amount of about 0.2 to 20 mol %, 0.5 to 10 mol %, 1 to 5 mol %, or 1 to 2.5 mol %, based on total moles of cyclic carbonyl monomer.

The nitrogen base accelerator is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator is calculated based on the equivalent molecular weight per nucleophilic group in the initiator. For example, hydroxyl groups can be present in an amount of 0.001 to 10.0 mol %, 0.1 to 2.5 mol %, 0.1 to 1.0 mol %, and 0.2 to 0.5 mol %, based on total moles of cyclic carbonyl monomer. If the molecular weight of the initiator is 100 g/mole and the initiator has 2 hydroxyl groups, the equivalent

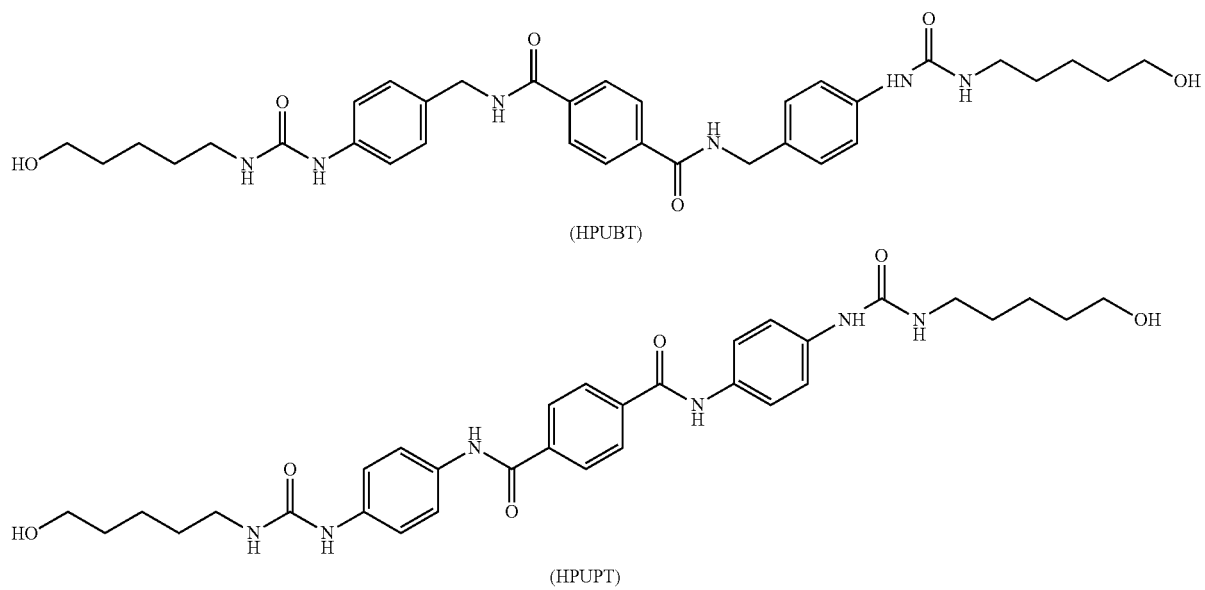

(HPUBT)

(HPUPT)

The ring-opening polymerization reaction can be performed with or without the use of a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter. In a specific embodiment, reaction mixture for the ring-opening polymerization is free of a solvent.

The ring-opening polymerization can be performed at a temperature that is about ambient temperature or higher, more specifically a temperature from 15° C. to 200° C., and more particularly 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

Whether performed in solution or in bulk, the polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, the nitrogen base accelerator is present in an amount of 0.1 to 5.0 mol %, and the hydroxyl groups of the initiator are present in an amount of 0.1 to 5.0 mol % based on the equivalent molecular weight per hydroxyl group in the initiator.

As stated above, the first polymer is a living polymer. The first polymer comprises a terminal hydroxyl group, terminal thiol group, or terminal amine group, each of which can initiate ROP chain growth. The first polymer can optionally be endcapped to prevent further chain growth and/or otherwise stabilize the backbone. Endcapping materials and techniques are well established in polymer chemistry. These include, for example materials for converting terminal hydroxyl groups to esters, such as carboxylic acid anhydrides, carboxylic acid chlorides, or reactive esters (e.g., p-nitrophenyl esters). In an embodiment, the first polymer is treated with acetic anhydride to endcap the chains with acetyl groups, forming the precursor block copolymer.

The first polymer and/or the precursor block copolymer can have a number average molecular weight $M_n$ as determined by size exclusion chromatography of at least 1000 g/mol, more specifically 4000 g/mol to 150000 g/mol, and even more specifically 10000 g/mol to 50000 g/mol. In an embodiment, the first polymer and/or the precursor block copolymer has a number average molecular weight $M_n$ of 10000 to 20000 g/mole. The first polymer and/or the precursor block copolymer also has a narrow polydispersity index (PDI), generally from 1.01 to 1.35, more particularly 1.10 to 1.30, and even more particularly 1.10 to 1.25. The hydrophilic block and the hydrophobic block of the cationic block copolymer can independently comprise a backbone selected from the group consisting of polyesters, polycarbonates, polyestercarbonates, and combinations thereof.

The catalysts can be removed by selective precipitation or in the case of the solid supported catalysts, simply by filtration. The first polymer can comprise residual catalyst in an amount greater than 0 wt. % (weight percent), based on total weight of the first polymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the first polymer and the residual catalyst. Similarly, the precursor block copolymer can comprise a residual catalyst in an amount greater than 0 wt. %, based on total weight of the precursor block copolymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the precursor block copolymer and the residual catalyst.

The precursor block copolymer comprises first repeat units derived from the first cyclic carbonyl monomer. The first repeat units comprising a side chain moiety comprising a reactive monovalent leaving group, which when treated with a tertiary amine, produces a cationic block copolymer comprising a moiety comprising a quaternary amine. No limitation is placed on the structure of the tertiary amine, with the proviso that the tertiary amine is capable of reacting with more than 0% of the monovalent leaving groups, more particularly 10% or more, 20% or more, 30% or more, 40% or more, 50% or more, 60% or more, 70% or more, or more particularly 80% or more of the monovalent leaving groups of the first repeat units to form a side chain moiety comprising a quaternary amine.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In this example, the cationic block copolymer will comprise first repeat units comprising a side chain moiety comprising a quaternary amine and a carboxylic acid group.

The tertiary amine can also comprise isotopically enriched versions of the tertiary amine, such as trimethylamine-$^{14}$C, trimethylamine-$^{15}$N, trimethylamine-$^{15}$N, trimethyl-$^{13}$C$_3$-amine, trimethyl-d$_9$-amine, and trimethyl-d$_9$-amine-$^{15}$N. The tertiary amine can also comprise a radioactive moiety suitable for targeting a specific cell type, such as a cancer cell. The radioactive moiety can comprise a heavy metal radioactive isotope.

The tertiary amine can be a bis-tertiary amine of the general formula (11):

where L" is a divalent linking group comprising 2 to 30 carbons, and each monovalent $R^b$ group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocyclic ring comprising 2 to 10 carbons, ether group, amide group, ester group, and combinations of the foregoing additional functional groups. The heterocyclic ring can comprise oxygen, sulfur and/or nitrogen. Two or more $R^b$ groups can also together form a ring. Representative L" groups include —(CH$_2$)$_{e'}$— where e' is an integer from 2 to 30, —(CH$_2$CH$_2$O)$_{e''}$CH$_2$CH$_2$— where e" is an integer from 1 to 10, —CH$_2$CH$_2$SCH$_2$CH$_2$—, —CH$_2$CH$_2$SSCH$_2$CH$_2$—, —CH$_2$CH$_2$SOCH$_2$CH$_2$—, and —CH$_2$CH$_2$SO$_2$CH$_2$CH$_2$—. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocyclic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3-propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The cationic block copolymer is isolated by one or more precipitations in an organic solvent such as tetrahydrofuran, followed by filtration and drying in vacuo. More than 0% of the first repeat units comprise a side chain moiety comprising a quaternary amine group. When the precursor block copolymer is treated with a bis-tertiary amine, more than 0% of the first repeat units comprise a side chain moiety comprising a quaternary amine group and a tertiary amine group. When the precursor block copolymer is treated with a tertiary amine comprising a carboxylic acid group, more than 0% of the first repeat units derived from the first cyclic carbonyl monomer comprise the side chain moiety comprising the quaternary amine group and the carboxylic acid group. The quaternary amine group is present in the cationic block copolymer in an amount of from more than 0% of the side chain monovalent leaving groups derived from the first cyclic carbonyl monomer. More particularly, the quaternary amine group is present in the cationic block copolymer in an amount of from 10 to 100%, 20 to 100%, 30 to 100%, 40 to 100%, 50 to 100%, 60 to 100%, 70 to 100%, or 80 to 100% of the side chain monovalent leaving groups derived from the first cyclic carbonyl monomer. When the precursor block copolymer is treated with a bis-tertiary amine, the tertiary amine group can be present in the cationic block copolymer in an amount of from more than 0% of the monovalent leaving groups in the first repeat units of the precursor block copolymer, more particularly from 10 to 100%, from 20 to 100%, from 30 to 100%, from 40 to 100%, from 50 to 100%, from 60 to 100%, from 70 to 100%, or from 80 to 100% of the monovalent leaving groups in the first repeat units of the precursor block copolymer.

The cationic block copolymer can have a number average molecular weight $M_n$ as determined by size exclusion chromatography of at least 1000 g/mol, more specifically of from 4000 g/mol to 150000 g/mol, and even more specifically of from 10000 g/mol to 50000 g/mol. In an embodiment, the cationic block copolymer has a number average molecular weight $M_n$ of from 10000 to 20000 g/mole. The cationic block copolymer also has a narrow polydispersity index (PDI), generally a value of from 1.01 to 1.35, more particularly of from 1.10 to 1.30, and even more particularly of from 1.10 to 1.25.

More particularly, the cationic block copolymer is an amphiphilic block copolymer comprising two or more block copolymer chains linked to a chain fragment derived from a diol initiator. Each of the two or more block copolymer chains comprises a hydrophobic block and a hydrophilic block, and each of the two or more block copolymer chains can optionally be endcapped. In an embodiment, the hydrophilic block of each of the two or more block copolymer chains is linked to the chain fragment derived from a rigid diol initiator, and the hydrophobic block is linked to the hydrophilic block and the optional endcap group. In another embodiment, the hydrophobic block of each of the two or more block copolymer chains is linked to the chain fragment derived from a rigid diol initiator, and the hydrophilic block is linked to the hydrophobic block and the optional endcap group. In an embodiment, the diol initiator is selected from the group consisting of HPUBT, HPUPT, and BnMPA.

A method of preparing a cationic block copolymer comprises forming a reaction mixture comprising a catalyst, an accelerator, a diol initiator, and an optional solvent; sequentially adding to the reaction mixture and polymerizing to form a first block copolymer a first cyclic carbonyl monomer comprising a leaving group capable of reacting with a tertiary amine, and a second cyclic carbonyl monomer not capable of reacting with the tertiary amine, wherein the first block copolymer comprises first repeat units derived from the first cyclic carbonyl monomer by ring-opening polymerization, and second repeat units derived from the second cyclic carbonyl monomer by ring-opening polymerization; optionally endcapping the first block copolymer to form a precursor block copolymer; and treating the precursor block copolymer with a tertiary amine to form the cationic block copolymer, wherein more than 0% of the first repeat units derived from the first cyclic monomer comprise a side chain moiety comprising a quaternary amine. In an embodiment, 70% or more of the first repeat units derived from the first cyclic monomer comprise a moiety comprising a quaternary amine. In an embodiment, the diol initiator is monomeric alkylene diol initiator selected from the group consisting of ethylene glycols, propylene glycols, butylene glycols, pentylene glycols, hexylene glycols, and mixtures thereof. More particularly, the monomeric alkylene diol initiator is BnMPA.

Another method of forming a biodegradable cationic block copolymer comprises:

(i) forming a reaction mixture comprising an organocatalyst, an accelerator, an optional solvent, and a dinucleophilic initiator of the general formula (10):

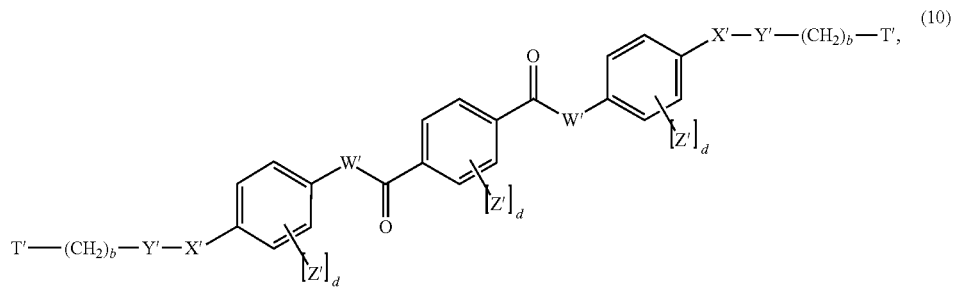

wherein each X' and each W' is independently a single bond or a divalent radical selected from the group consisting of —(CR'$_2$)$_c$—, —O—, —S—, —NR'—, and —NR'(CR'$_2$)$_c$—, each c is independently an integer from 1 to 5, R' is a monovalent radical selected from the group consisting of hydrogen, alkyl groups comprising 1 to 30 carbons, and aryl groups comprising 6 to 30 carbons, each Y' is a single bond or a divalent radical selected from the group consisting of —CO— (carbonyl), —NR'CO— (aminocarbonyl), —COO— (oxycarbonyl), —SCO— (thiocarbonyl), each T' is a monovalent nucleophile independently selected from the group consisting of —OH, —SH, —NH$_2$, and —NR$^d$H, wherein R$^d$ is a monovalent radical selected from the group consisting of hydrogen, alkyl groups comprising 1 to 30 carbons, and aryl groups comprising 6 to 30 carbons, each Z' is a monovalent radical independently selected from the group consisting of halides, alkyl groups comprising 1 to 20 carbons, alkoxy groups comprising 1 to 20 carbons, and aryl groups comprising 6 to 20 carbons, each b is an integer independently from 1 to 20, and each subscript d is independently 0 or an integer from 1 to 4;

(ii) sequentially adding to the reaction mixture and reacting by ring-opening polymerization a first cyclic carbonyl monomer followed by a second cyclic carbonyl monomer, thereby forming a first block copolymer, wherein the first cyclic carbonyl monomer comprises a monovalent leaving group capable of reacting with a tertiary amine to form a quaternary amine, and the second cyclic carbonyl monomer is not capable of reacting with the tertiary amine to form any quaternary amine, and wherein the first block copolymer comprises a chain fragment comprising two or more backbone aromatic rings derived from the dinucleophilic initiator;

(iii) optionally endcapping the first block copolymer, thereby forming a precursor block copolymer; and (iv) treating the precursor block copolymer with the tertiary amine to form the cationic block copolymer, wherein the cationic block copolymer comprises first repeat units derived from the first cyclic carbonyl monomer, more than 0% of the first repeat units comprise a side chain moiety comprising the quaternary amine, and the cationic block copolymer biodegrades 60% within 180 days in accordance with ASTM D6400. In an embodiment, the sequential reaction is performed in reverse order to form the first block copolymer. In another embodiment, the first block copolymer is endcapped using a carboxylic anhydride, thereby forming a terminal ester group. The hydrophilic block and the hydrophobic block can independently comprise a backbone selected from the group consisting of polyesters, polycarbonates, polyestercarbonates, and combinations thereof. The second repeat unit can comprise a latent carboxylic acid group, such as a side chain acetal ester group. The monovalent leaving group can be selected from the group consisting of halides, sulphonate esters, and epoxides. In an embodiment, the tertiary amine is trimethylamine. In another embodiment, the tertiary amine is a bis-tertiary amine and the side chain moiety comprises the quaternary amine and a tertiary amine. In another embodiment, the bis-tertiary amine is selected from the group consisting of N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof.

As stated above, the cationic block copolymer obtained by ring-opening polymerization comprises as many chain branches as the number of initiating sites on the initiator. Further, the cationic block copolymer comprises as many blocks per chain as the number of sequential ring-opening polymerizations prior to endcapping, with the understanding that successive ring-opening polymerizations are performed with different cyclic carbonyl monomer compositions.

In de-ionized water the cationic block copolymers self-assemble into nanoparticulate micelles. The cationic block copolymers have a critical micelle concentration (CMC) of from more than 0 micrograms/mL to about 300 micrograms/mL. More particularly, the cationic block copolymers have a CMC of from 1 microgram/mL to 90 micrograms/mL, 1 microgram/mL to 80 micrograms/mL, 1 microgram/mL to 70 micrograms/mL, 1 microgram/mL to 60 micrograms/mL, 1 microgram/mL to 50 micrograms/mL, 1 microgram/mL to 40 micrograms/mL, 1 microgram/mL to 30 micrograms/mL, 1 microgram/mL to 20 micrograms/mL, 1 microgram/mL to 10 micrograms/mL, or more particularly 1 microgram/mL to 6 micrograms/mL. In an embodiment, the cationic block copolymers have a CMC of from about 15 micrograms/mL to about 71 micrograms/mL.

The nanoparticulate micelles have an average particle size, for example, of more than 0 nm. More particularly, the micelles have an average particle size of from 10 nm to 500 nm, 10 nm to 250 nm, 10 nm to 200 nm, 10 nm to 150 nm, 10 nm to 120 nm, 10 nm to 100 nm, 10 nm to 90 nm, 10 nm to 80 nm, 10 nm to 70 nm, 10 nm to 60 nm, 10 nm to 50 nm, 10 nm to 40 nm, 10 nm to 30 nm, or 10 nm to 20 nm. In an embodiment, the micelles have an average particle size of from 50 nm to 100 nm. In another embodiment, the average particle size of the micelles is from about 20 nm to about 402 nm. Particle size is measured by dynamic light scattering (Brookhaven Instrument Corp., Holtsville, N.Y., U.S.A.) equipped with a He—Ne laser beam at 658 nm (scattering angle: 90°). The particle size measurements are repeated for 5 runs for each sample, and the particle size are reported as the average of 5 readings. For the foregoing particle sizes, the aqueous solution can have a pH of from 5.0 to 8.0. The particle size is the average hydrodynamic diameter of the micelles in water.

The zeta potential of the micelles at a concentration of 3000 mg of cationic block copolymer per liter in de-ionized water is about 20 mV to about 80 mV, more particularly 45 mV to about 69 mV.

The micelles have a minimum inhibitory concentration (MIC) for microbial growth of from more than 0 micromoles/L to about 100 micromoles/L. More particularly, the micelles have a MIC of from 1 micromole/L to 80 micromoles/L, 1 micromole/L to 70 micromoles/L, 1 micromole/L to 60 micromoles/L, 1 micromole/L to 50 micromoles/L, 1 micromole/L to 40 micromoles/L, 1 micromole/L to 30 micromoles/L, 1 micromole/L to 20 micromoles/L, 1 micromole/L to 10 micromoles/L, or more particularly 1 micromole/L to 6 micromoles/L. In an embodiment, the micelles have a MIC of from about 4 micromoles/L to about 66 micromoles/L, wherein micromoles are based on $M_n$ of the cationic block copolymer.

In an embodiment, an aqueous micelle mixture is disclosed comprising 5 to 500 micrograms/mL of the biodegradable cationic block copolymer. The biodegradable cationic block copolymer comprises a hydrophilic block comprising first repeat units derived from a first cyclic carbonyl monomer by ring-opening polymerization, wherein more than 0% of the first repeat units comprise a side chain moiety comprising a quaternary amine group; a hydrophobic block comprising second repeat units derived from a second cyclic carbonyl monomer by ring-opening polymerization; a chain fragment derived from a dinucleophilic initiator for the ring opening polymerization; and an optional endcap group. The aqueous micelle mixture inhibits microbial growth by inducing lysis of the microbial cell membrane, and the cationic block copolymer biodegrades 60% within 180 days in accordance with ASTM D6400. The chain fragment can comprise two or more backbone aromatic rings derived from the dinucleophilic initiator. In an embodiment, the chain fragment is derived from a dinucleophilic initiator having the formula (10), such as HPUBT or HPUPT. In another embodiment, the chain fragment is derived from a monomeric alkylene diol initiator selected from the group consisting of ethylene glycols, propylene glycols, butylene glycols, pentylene glycols, hexylene glycols, and mixtures thereof. More specifically, the monomeric alkylene diol initiator is BnMPA. In still another embodiment, the quaternary amine of the aqueous micelle is derived from trimethylamine. The aqueous micelles can have a rod-like structure or a spherical structure. The aqueous micelles can be loaded micelles comprising a biologically active material, wherein the biologically active material is not negatively charged.

The biologically active material can be a peptide, drug, or a combination thereof. Non-limiting examples of antimicrobial drugs include, but are not limited to, aminoglycosides such as amikacin, gentamicin, kanamycin, neomycin, streptomycin, and tobramycin; antibiotics such as bacitracin, clindamycin, daptomycin, lincomycin, linezolid, metronid, polymyxin, rifaximin, vancomycin; cephalosporins such as cephazolin; macrolide antibiotics such as erythromycin, azithromycin and the like; β-lactam antibiotics such as penicillins; quinolones such as ciprofloxacin; sulfonamides such as sulfadiazine; minocycline and tetracycline; and other antibiotics such as metronidazole, rifampin, triclosan and chlorhexidine. In an embodiment, the biologically active material is an antimicrobial drug that enhances or broadens the spectrum of antimicrobial activity of the micelles. The first cyclic carbonyl monomer can be a compound of formula (2), formula (3), formula (4), or formula (5).

A method of forming an aqueous micelle mixture comprises mixing with agitation, at a pH of from 5.0 to 8.0 and at a concentration of 5 to 500 micrograms/mL or more, a biodegradable cationic block copolymer in an aqueous solution, thereby forming the aqueous micelle mixture; wherein the micelles have an average particle size of 10 to 500 nm, and the block copolymer comprises a hydrophilic block comprising first repeat units derived from a first cyclic carbonyl monomer by ring-opening polymerization, wherein more than 0% of the first repeat units comprise a side chain moiety comprising a quaternary amine group, a hydrophobic block comprising second repeat units derived from a second cyclic carbonyl monomer by ring-opening polymerization, a chain fragment derived from a dinucleophilic initiator for the ring opening polymerization, and an optional endcap group. The method can further comprise contacting the first aqueous mixture with a second aqueous mixture comprising a biologically active material, wherein the biologically active material is not negatively charged. The aqueous micelle mixture induces 0 to 15% hemolysis, more particularly no hemolysis, and has a cytotoxicity of 0 to 20%, or more particularly no cytotoxicity.

Further disclosed is a method of treating a microbe, comprising: contacting a cell membrane of the microbe with an aqueous micelle mixture comprising a biodegradable cationic block copolymer at a pH of from 5.0 to 8.0 and at a concentration effective in inducing lysis of the cell membrane; wherein the cationic block copolymer comprises: a hydrophilic block comprising first repeat units derived from a first cyclic carbonyl monomer by ring-opening polymerization, wherein more than 0% of the first repeat units comprise a side chain moiety comprising a quaternary amine group; a hydrophobic block comprising second repeat units derived from a second cyclic carbonyl monomer by ring-opening polymerization; a chain fragment derived from a dinucleophilic initiator for the ring opening polymerization, and an optional endcap group; and wherein the cationic block copolymer biodegrades 60% within 180 days in accordance with ASTM D6400. In an embodiment, the chain fragment comprises two or more backbone aromatic rings derived from the dinucleophilic initiator. In another embodiment, the dinucleophilic initiator is a monomeric alkylene diol selected from the group consisting of ethylene glycols, propylene glycols, butylene glycols, pentylene glycols, hexylene glycols, and mixtures thereof. In another embodiment, the micelles are loaded micelles comprising a biologically active material that enhances or broadens the spectrum of antimicrobial activity of the micelles. The biologically active material is not negatively charged. The microbe can be exposed to the micelles or the loaded micelles in vitro, ex vivo and in an animal, or in vivo (for example, an animal or human).

The following examples demonstrate that the biodegradable polycarbonate and poly(estercarbonate) block copolymers produced by organocatalytic ring-opening polymerization are effective antimicrobial agents. The combination of biodegradable halogen-containing carbonate and a quaternization reaction with amines provides a versatile pathway to forming cationic block copolymers having diverse functionality for anti-microbial applications. The halide on the precursor block copolymers can be varied depending on the target architectures and type of application. The cationic polycarbonates can self-assemble into micellar nanoparticles having a hydrophobic core and a positively charged surface. A biologically active material can be loaded into the hydrophobic core to enhance or broaden the spectrum of antimicrobial activities of the micelles.

EXAMPLES

Materials for Polymer Synthesis.

THF, DMF, and methylene chloride used in the reaction were obtained by a solvents drying system (Innovative). N-(3, 5-trifluoromethyl)phenyl-N'-cyclohexyl-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, *Macromolecules*, 2006, 39 (23), 7863-7871, and dried by stirring in dry THF over $CaH_2$, filtering, and removing solvent under vacuum. BisMPA benzylester (BnMPA) was prepared as described below, and further dried by dissolving in dry THF, stirring with $CaH_2$, filtering, and removing the solvent in vacuo. DMSO, 1,8-diazabicyclo[5,4,0]undec-7-ene (DBU), and (−)-sparteine were stirred over $CaH_2$, vacuum distilled, then stored over molecular sieves (3 Å). L-lactide (LLA) and D-lactide (DLA) (Purac, 99%) were recrystallized from dry toluene 3 times prior to use. Trimethylenecarbonate (TMC) was azeotropically dried from toluene prior to use. Other reagents were used as received.

Materials for Physicochemical and Biological Characterizations of Polymers.

*Bacillus subtilius* and *Staphylococcus aureus* were obtained from ATCC, and grown in tryptic soy broth at 37° C. Methicillin-resistant *Staphylococcus aureus*, *Enterococcus faecalis* and *Cryptococcus neoformans* were extracted from patients' phlegm, and kindly provided by Y. S. Yu, Department of Infectious Diseases, The First Affiliated Hospital, College of Medicine, Zhejiang University, P. R. China. The clinical samples were grown in Mueller-Hinton broth at 37° C.

I. Cationic Block Copolymers Derived from a Monomeric Alkylene Diol Initiator.

A particularly useful synthon for functional biodegradable monomers is so-called MTC family of cyclic carbonate monomer derived from 2,2-bis(methylol)propionic acid (bisMPA). BisMPA provides a facile route to 5-methyl-5-carboxyl-1,3-dioxan-2-one (MTCOH) and derivative thereof, as shown in Scheme 1.

Scheme 1.

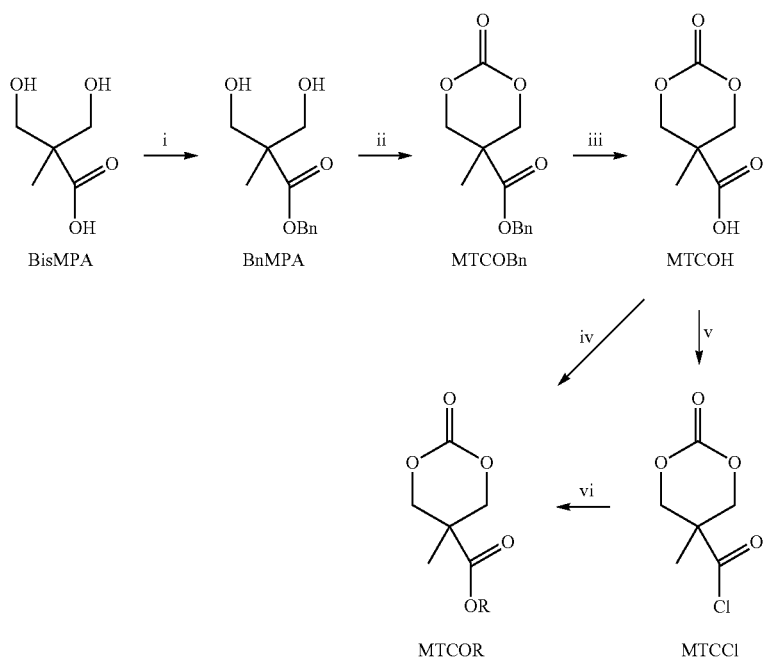

This approach parallels that of (meth)acrylate derivatization and has been demonstrated to create a wide selection of functional monomers capable of undergoing ring-opening polymerization. 2,2-Bis(methylol)propionic acid (BisMPA) is first converted (i) to a benzyl ester BnMPA (herein also used as an initiator for the polymerizations), followed by reaction (ii) of BnMPA with triphosgene to form a cyclic carbonyl monomer, MTCOBn. MTCOBn is debenzylated (iii) to produce the cyclic carbonyl carboxylic acid, MTCOH. Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCCl followed by treatment (vi) of MTCCl with ROH in the presence of a base to form MTCOR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bis-MPA; (ii) triphosgene, pyridine, $CH_2Cl_2$, −78° C. to 0° C., 95% yield of MTCOBn; (iii) Pd/C (10%), H2 (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCCl; (vi) ROH, $NEt_3$, RT, 3 hours yields MTCOR.

Using the above scheme, MTCCl was reacted with 3-bromopropanol, 3-chloropropanol, 2-iodoethanol, and ethanol to form the corresponding MTCOPrBr, MTCOPrCl, MTCOEtI, and MTCOEt. The haloesters were purified by either recrystallization or by flash chromatography (ethyl acetate/hexane) in high yields (>85%). MTCOEt was used as a non-functional counterpart for dilution effects and to introduce hydrophobic blocks to the polymer for self-assembly.

Monomer Preparations.

Preparation of 5-methyl-5-(3-chloropropyl)oxycarboxyl-1,3-dioxan-2-one, (MTCOPrCl), MW 236.65

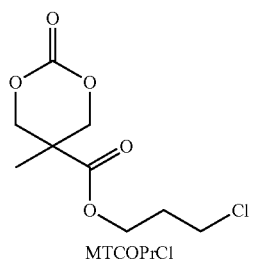

MTCOPrCl

MTCOH (8.82 g, 55 mmol) was converted to MTCOCl using standard procedures with oxalyl chloride. In a dry 250 mL round bottom flask equipped with a stir bar, the formed intermediate was dissolved in 150 mL of dry methylene chloride. Under nitrogen flow an addition funnel was attached in which 3-chloropropanol (4.94 g, 4.36 mL, 52.25 mmol), pyridine (3.95 g, 4.04 mL, 55 mmol), and 50 mL of dry methylene chloride was charged. The flask was cooled to 0° C. using an ice bath and the top solution was added drop wise during a period of 30 minutes. The formed solution was stirred for an additional 30 minutes before the ice bath was removed and the solution was stirred for an additional 16 hours under nitrogen. The crude product MTCOPrCl was directly applied onto a silica gel column and the product was separated by eluting with 100% methylene chloride. The product fractions were removed and the solvent was evaporated, yielding the product as off-white oil, which crystallized upon standing. Yield 11 g (85%). $^1$H-NMR ($CDCl_3$) delta: 4.63 (d, 2H, $CH_2$), 4.32 (t, 2H, CH$_2$), 4.16 (d, 2H, CH$_2$), 3.55 (t, 2H, CH$_2$), 2.09 (m, 2H, CH$_2$), 1.25 (s, 3H, CH$_3$).

Preparation of 5-methyl-5-(3-bromopropyl)oxycarboxyl-1,3-dioxan-2-one, (MTCOPrBr), MW 281.10

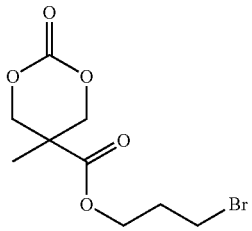

MTCOPrBr

MTCOPrBr was prepared by the procedure for MTCOPrCl on a 45 mmol scale using 3-bromo-1-propanol as the alcohol. The product was purified by column chromatography, and subsequently recrystallized to yield white crystals (6.3 g, 49%). $^1$H NMR (400 MHz, CDCl$_3$): delta 4.69 (d, 2H; CH$_2$OCOO), 4.37 (t, 2H; OCH$_2$), 4.21 (d, 2H; CH$_2$OCOO), 3.45 (t, 2H; CH$_2$Br), 2.23 (m, 2H; CH$_2$), 1.33 (s, 3H; CH$_3$). $^{13}$C NMR (100 MHz, CDCl$_3$): delta 171.0, 147.3, 72.9, 63.9, 40.2, 31.0, 28.9, 17.3.

Monomer 3. Preparation of 5-methyl-5-(2-iodoethyl)oxycarboxyl-1,3-dioxan-2-one, (MTCOEtI), MW 314.08

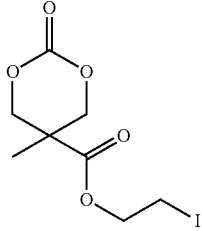

MTCOEtI

MTCOEtI was prepared by the procedure for MTCOPrCl on a 45 mmol scale, using 2-iodoethanol as the alcohol, and was purified by column chromatography and subsequent recrystallization to yield yellowish crystals (7.7 g, 54%). $^1$H NMR (400 MHz, CDCl$_3$): delta 4.73 (d, 2H; CH$_2$OCOO), 4.45 (t, 2H; OCH$_2$), 4.22 (d, 2H; CH$_2$OCOO), 3.34 (t, 2H; CH$_2$I), 1.38 (s, 3H; CH$_3$). $^{13}$C NMR (100 MHz, CDCl$_3$): delta 170.5, 147.3, 72.8, 65.6, 40.3, 17.5, −0.3.

Organocatalytic Ring-Opening Polymerizations. General Procedures.

Ring-opening polymerizations were conducted in the presence of organocatalysts, N-(3,5-trifluoromethyl)phenyl-N'-cyclohexyl-thiourea (TU) and 1,8-diazabicyclo[5,4,0]undec-7-ene (DBU), in methylene chloride at room temperature (1-2 hours) to yield first polymers comprising a pendant 3-halopropyl esters with molecular weight consistent with the feed ratio ([M]$_0$/[I]$_0$), narrow polydispersities (1.1-1.2), and end group fidelity. Endcapping of the first polymer was accomplished by treating the terminal hydroxyl group with acetic anhydride for 24 hours to 48 hours. This can prevent scission of polymer chain by the back-biting stemming from the terminal hydroxyl group in the presence of amine during the quaternization reaction.

The ROP polymers prepared below have the general formula (12):

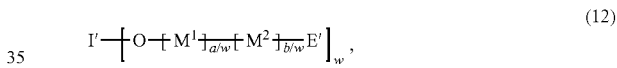

(12)

wherein I' is the subunit derived from the initiator, w is the number of initiating groups on I', M$^1$ is a cyclic carbonyl monomer, M$^2$ is a another cyclic cyclic monomer, E' is an optional endcap group, and a:b is the M$^1$:M$^2$ mole ratio. In the preparation of block copolymers, is M$^1$ added first, followed by M$^2$. For random copolymers, it is understood that either monomer M$^1$ or M$^2$ can be attached to the initiator I'. Examples 1 to 3 were initiated with BnMPA, a diol; therefore w=2 and two polymer chains are formed that are linked by the chain fragment derived from the initiator. Scheme 2 illustrates the steps used to make Examples 1 to 3 using BnMPA.

Scheme 2.

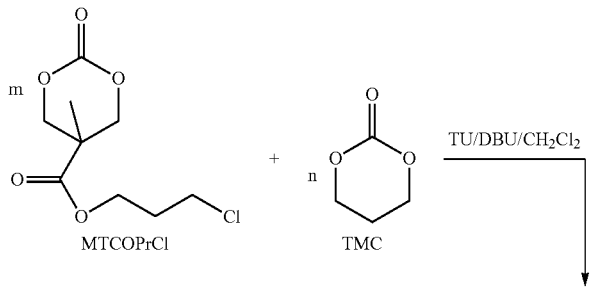

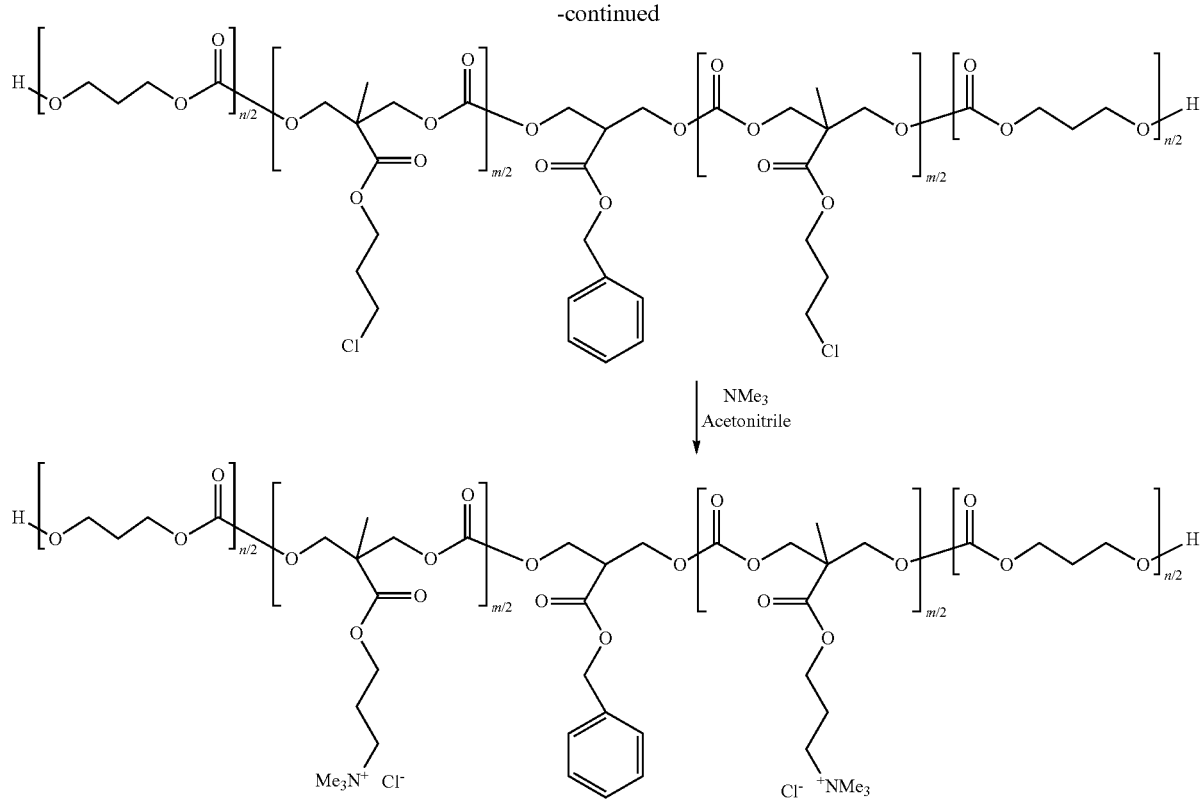

Examples 1 to 3

Preparation of BnMPA Initiated Cationic Block Copolymers

MTCOPrCl and trimethylene carbonate (TMC) were copolymerized using a mixture of the Lewis acid 1-(3,5-bis (trifluoromethyl)-phenyl)-3-cyclohexyl-2-thiourea (TU) with the Lewis base 1,8-diazabicyclo[5.4.0]undec-7-ene (DBU) (1:1 in mole) as the catalyst. In a glove-box 93 mg (0.422 mmol) of BnMPA initiator, 1.0 g (4.22 mmol) of MTCOPrCl (for a DP of 10), and 1.29 g (12.66 mmol) of TMC was charged in a 20 mL glass vial equipped with a stir bar. Dichloromethane was added and the concentration was adjusted to 2M. To the clear solution was added 80 mg (0.211 mmol) of thiourea catalyst and 32 mg (0.211 mmol) of DBU to initiate the polymerization. After five hours, 51 mg (0.422 mmol) of benzoic acid was added to quench the polymerization, after which the crude random copolymer was taken out off the glove-box, and precipitated in cold methanol. The precipitate was allowed to sediment, and the supernatant was decanted. The collected polymer was dried in a vacuum oven until a constant weight was reached. Yield ~2.1 g (~92%), GPC: $M_w$~6811 g/mol, $M_n$~5890 g/mol, PDI~1.15, $^1$H-NMR (CDCl$_3$) delta: 7.41-7.35 (m, 5H, initiator), 5.19 (s, 2H, initiator), 4.40-4.30 (m, 6H, MTC-polymer), 4.30-4.18 (t, 4H, TMC-polymer), 3.76 (t, 4H, end-group), 3.61 (t, 2H, MTC-polymer), 2.18-2.12 (m, 2H, MTC-polymer), 2.12-2.00 (m, 4H, TMC-polymer), 1.92 (m, 4H, end-group), 1.28 (s, 3H, MTC-polymer).

The chloride functional precursor block copolymer (2.0 g, about 0.4 mmol) was dissolved in acetonitrile (50 mL) and the solution was transferred (under nitrogen) into a 100 mL pressure safe Schlenk tube equipped with a stir bar. Under nitrogen the solution was cooled with dry ice after, which trimethylamine (about 0.5 g) was condensed into the Schlenk tube that was then sealed. The solution was heated to 50° C. and held for 48 hours under stirring. Following the reaction the solution was cooled to ambient temperature and nitrogen was bubbled through to remove excess trimethylamine. The solvent was removed by rotational evaporation, and the obtained product was dried in a vacuum oven until a constant weight was reached. $^1$H-NMR (DMSO-d$_6$) delta: 7.41-7.35 (m, 5H, initiator), 5.19 (s, 2H, initiator), 4.40-4.20 (m, 6H, MTC-polymer), 4.20-4.10 (t, 4H, TMC polymer), 3.50 (t, 4H, end-group), 3.50-3.40 (t, 2H, MTC-polymer), 3.10-3.0 (s, 9H, MTC-polymer), 2.10-2.0 (m, 2H, MTC-polymer), 2.0-1.90 (m, 4H, TMC-polymer), 1.85 (m, 4H, end-group), 1.22 (s, 3H, MTC-polymer).

Examples 1 to 3 differed in the molar ratio of MTCOPrCl and TMC. Table 8 lists the properties of Examples 1 to 3 prepared by the above procedure. Example 2 has a longer length of TMC (hydrophobic) block than Example 1, whereas Example 3 contains a longer length of cationic (hydrophilic) block.

TABLE 8

|  | PDI | m:n | $M_n$ (g/mol) | CMC Micrograms/mL in DI | Size (nm) | Zeta Potential |
|---|---|---|---|---|---|---|
| Example 1 | 1.15 | 1:3 | 4650 | 35.5 | 43 ± 7 | 47 ± 3 |
| Example 2 | 1.26 | 1:4.5 | 7520 | 15.8 | 402 ± 21 | 65 ± 5 |
| Example 3 | 1.25 | 2:3 | 8900 | 70.8 | 198 ± 9 | 60 ± 3 |

Critical micelle concentration (CMC) determination. CMC is an important parameter, above which an amphiphilic macromolecule forms core/shell structured nanoparticles (i.e., micelles). The CMC values of polymers in DI water and tryptic soy broth used to growing bacteria were estimated by fluorescence spectroscopy using pyrene as a probe. The fluorescence spectra were recorded by a LS 50B luminescence spectrometer (Perkin Elmer, U.S.A.) at room temperature. Aliquots of pyrene in acetone solution ($6.16 \times 10^{-5}$ M, 10 microliters) were added to containers and the acetone was left to evaporate. Polymer solutions (1 mL) at varying concentrations were added into the containers and left to equilibrate for 24 hours. The final pyrene concentration in each sample was $6.16 \times 10^{-7}$ M. The excitation spectra were scanned from 300 to 360 nm at an emission wavelength of 395 nm. Both the excitation and emission bandwidths were set at 2.5 nm. The intensity (peak height) ratios of $I_{337}/I_{334}$ from the excitation spectra were analyzed as a function of polymer concentration. The CMC was taken from the intersection between the tangent to the curve at the inflection and tangent of the points at low concentrations.

Figure 1B:
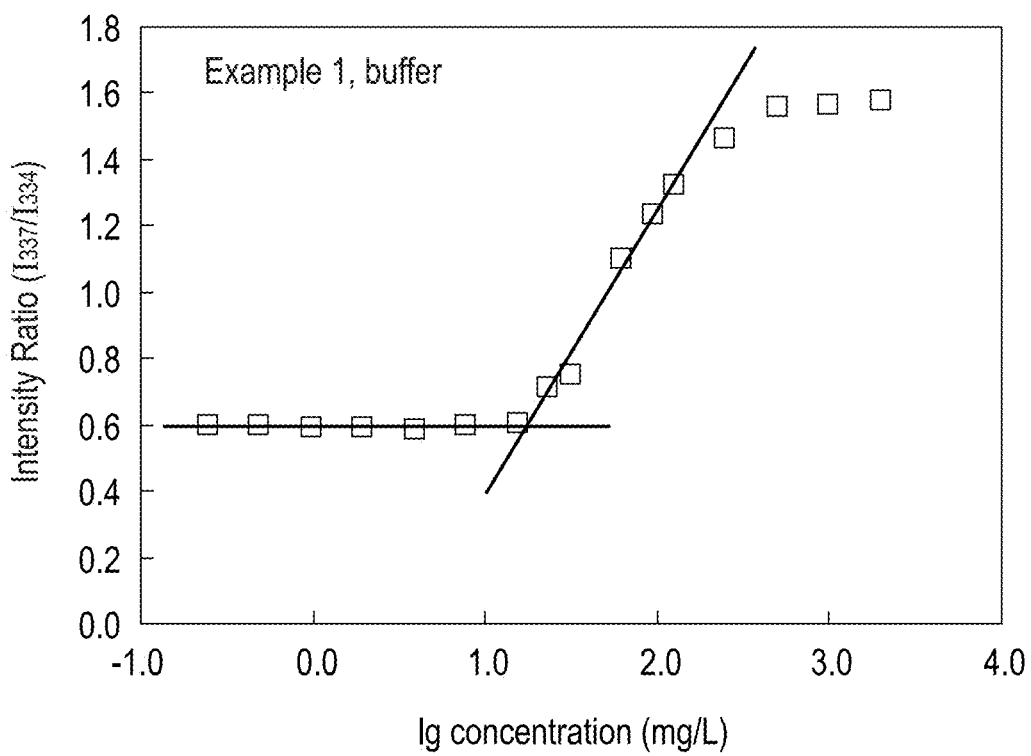
Figure 2A:
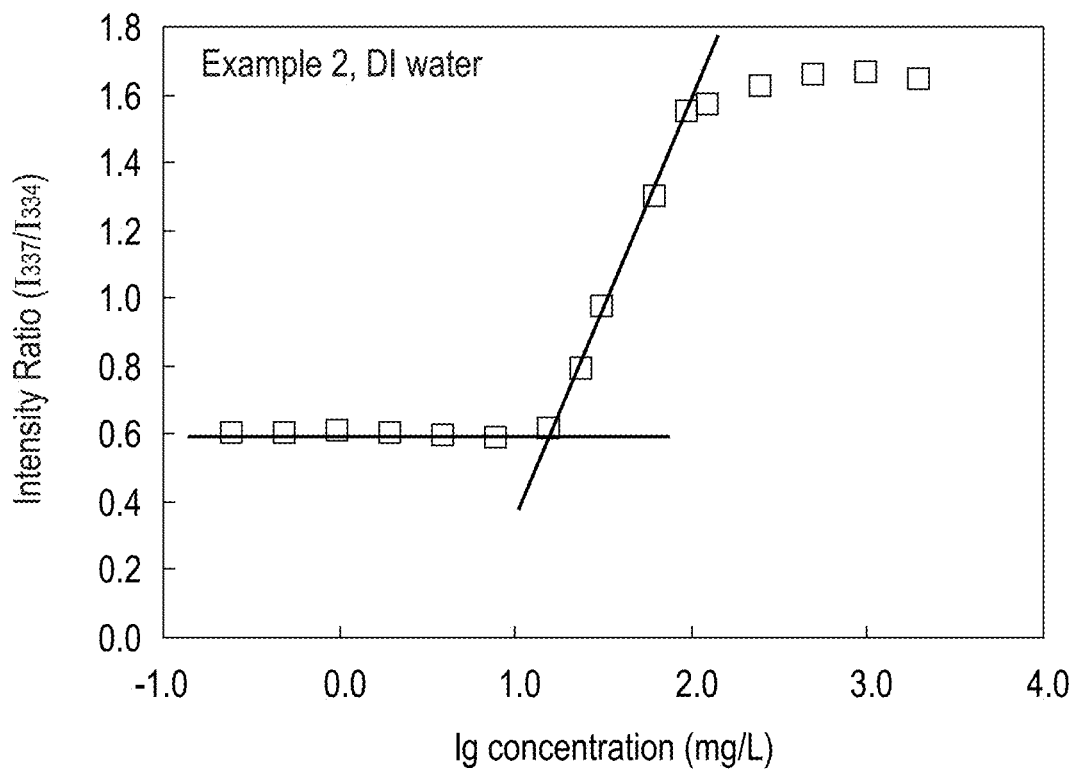
FIGS. 2A and 2B are graphs plotting $I_{337}/I_{334}$ ratio as a function of logarithm of polymer concentration (1 g C, mg/L) used in determining the CMC of the cationic block copolymer of Example 2 in de-ionized water and tryptic soy broth (medium for growth of bacteria), respectively.
Figure 2B:
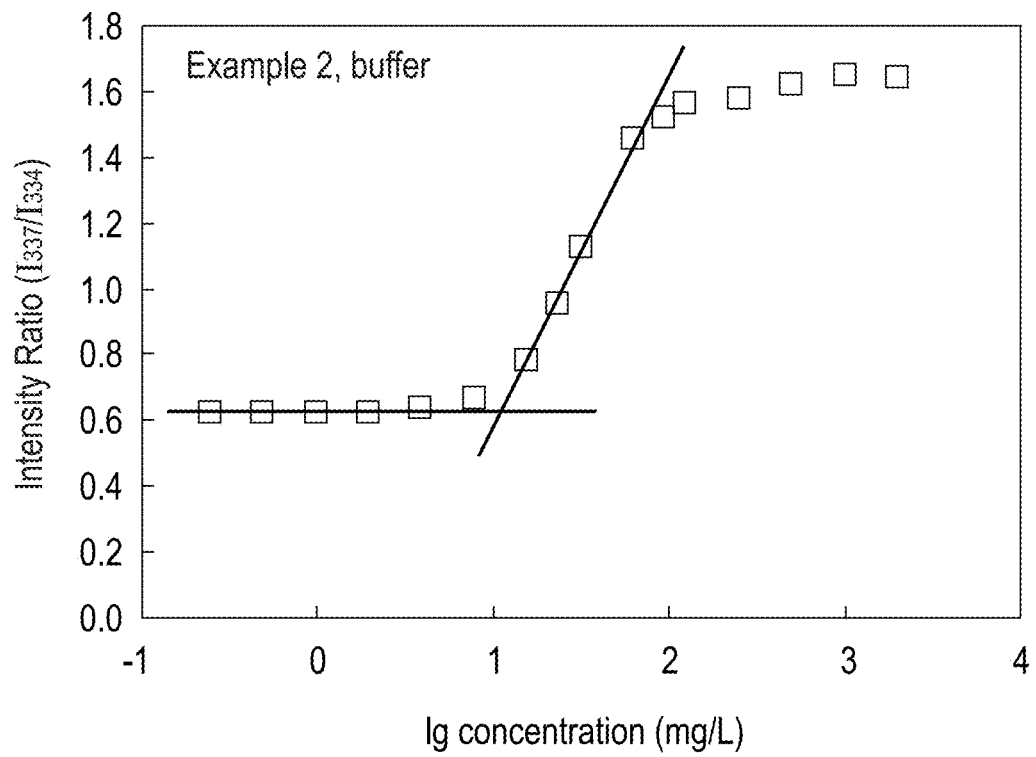
Figure 3A:
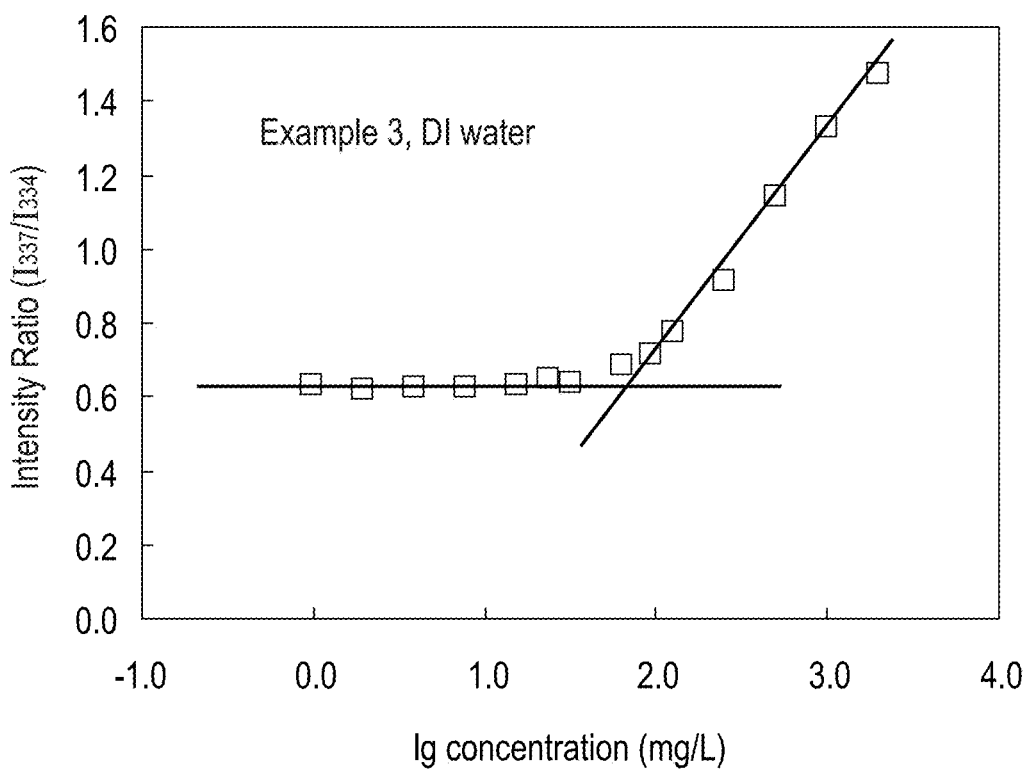
FIGS. 3A and 3B are graphs plotting $I_{337}/I_{334}$ ratio as a function of logarithm of polymer concentration (1 g C, mg/L) used in determining the CMC of the cationic block copolymer of Example 3 in de-ionized water and tryptic soy broth (medium for growth of bacteria), respectively.
Figure 3B:
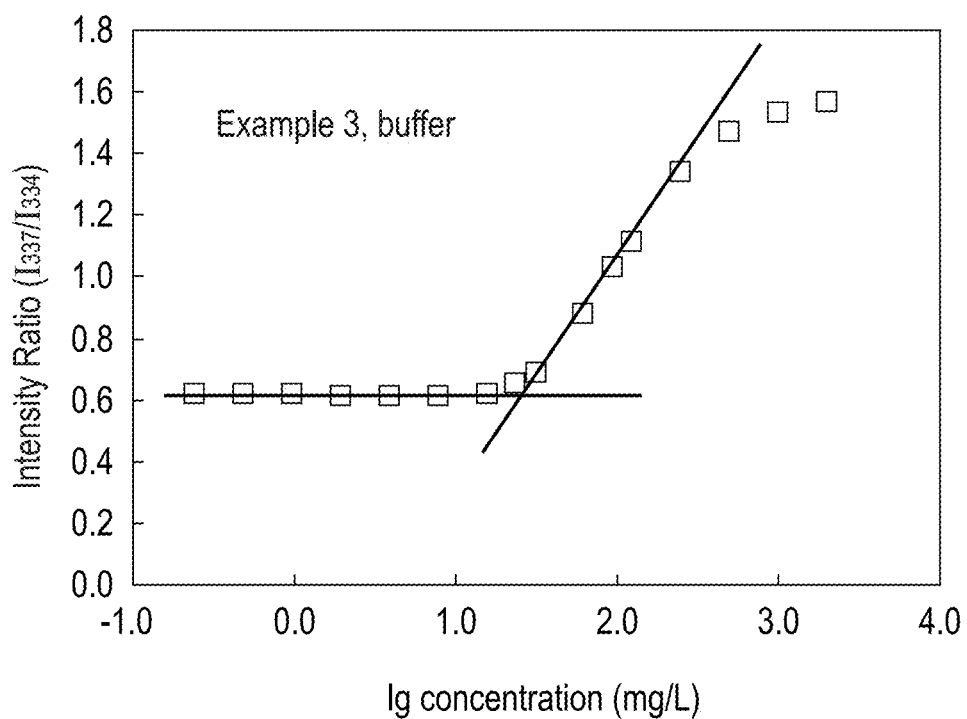

Polycarbonate Examples 1 to 3 form cationic micelles by dissolving the block copolymers in water, and have critical micelle concentrations (CMC) of 35.5, 15.8 and 70.8 micrograms/mL in de-ionized (DI) water. FIGS. 1A, 2A, and 3A are graphs showing the intersection points in the plot of $I_{337}/I_{334}$ ratio as a function of logarithm of polymer concentration (1 g C, mg/L) used in determining the CMC of Examples 1, 2 and 3, respectively, in de-ionized water. In tryptic soy broth, which is used for growing the bacteria employed in this study, Examples 1 to 3 have significantly lower CMC values, which are 17.8, 11.2 and 28.2 micrograms/mL, respectively. FIGS. 1B, 2B, and 3B are graphs showing the intersection points in the plot of $I_{337}/I_{334}$ ratio as a function of logarithm of polymer concentration (1 g C, mg/L) used in determining the CMC of Examples 1, 2 and 3, respectively, in tryptic soy broth. Example 2 has a lower CMC than Example 1, attributed to the relatively longer length of the hydrophobic block in Example 2, which is believed to provide stronger hydrophobic interactions between the chains of Example 2, leading to micelle formation at lower concentrations. Example 3 has a higher CMC than Example 1, which is attributed to the relatively longer length of the hydrophilic block in Example 3, believed to provide increased repulsive forces between chains in the longer hydrophilic block, requiring more polymer chains to come together to form a stable micelle. The average diameters of the self-assembled micelles from Examples 1 and 3 are below 200 nm (Table 8). Example 2, having the longest length of hydrophobic block, forms large aggregates that have an average diameter of 402 nm. The self-assembled micelles from Examples 1, 2 and 3 have positively charged surfaces with zeta potentials of 47, 65 and 60 mV respectively.

Figure 4:
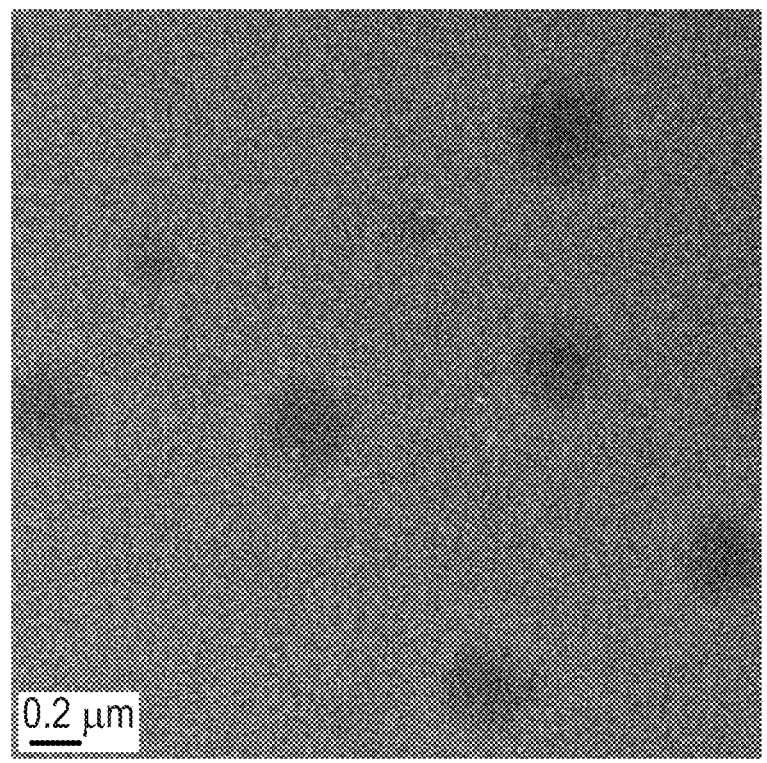
FIG. 4 is a transmission electron micrograph (TEM) image of the micelles formed with Example 3 in DI water.
Figure 5A:
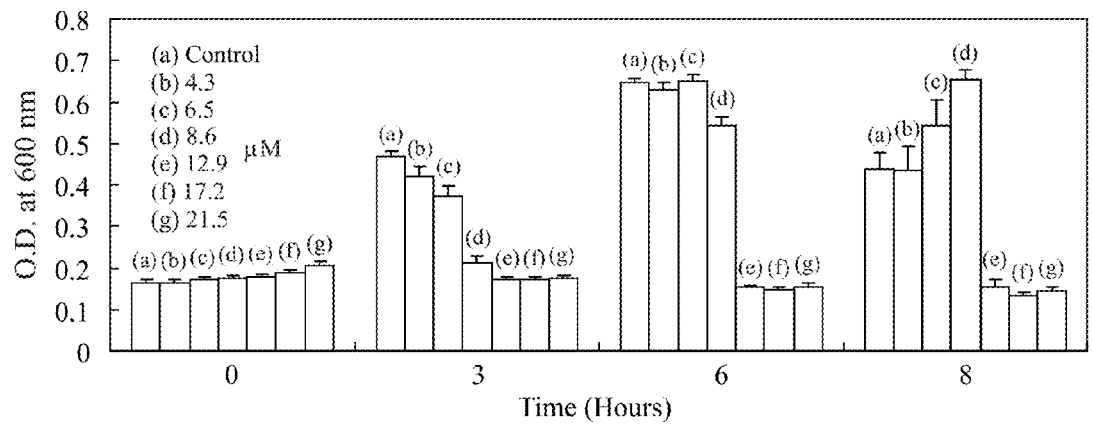
FIGS. 5A to 5E are bar charts showing the viability of Gram-positive bacteria *Bacillus subtilis, Staphylococcus aureus*, methicillin-resistant *Staphylococcus aureus* and *Enterococcus faecalis*, and the fungus *Cryptococcus neoformans*, respectively, when treated with micelles formed from Example 1.
Figure 5B:
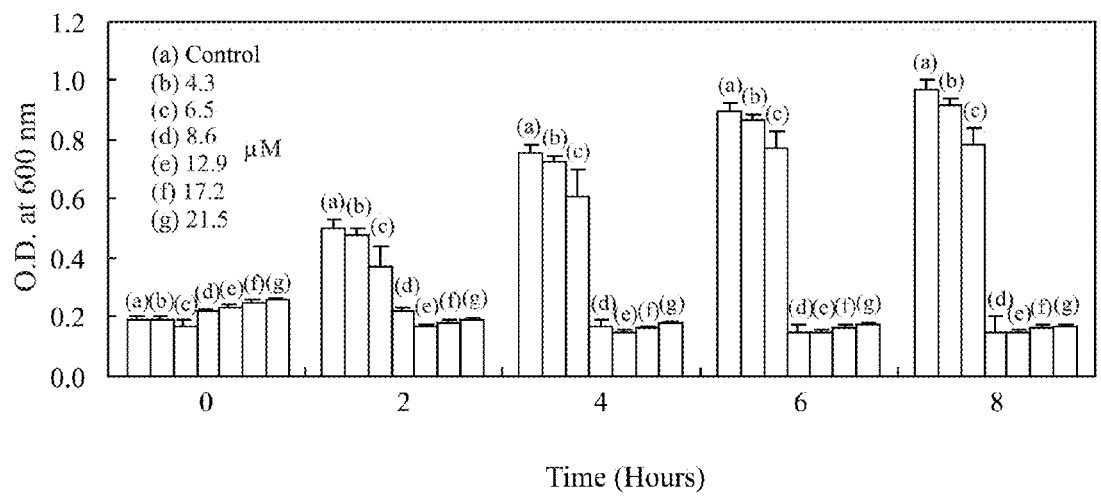
Figure 5C:
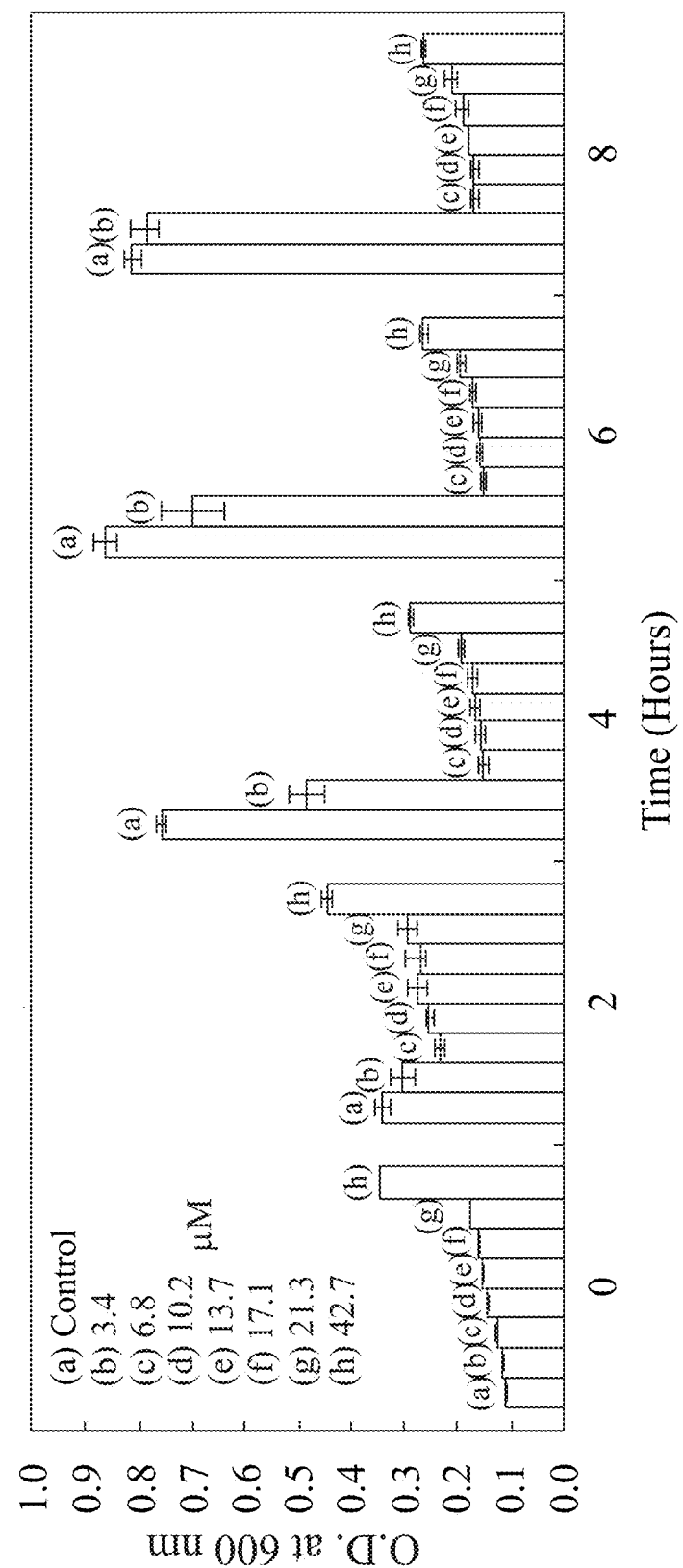
Figure 5D:
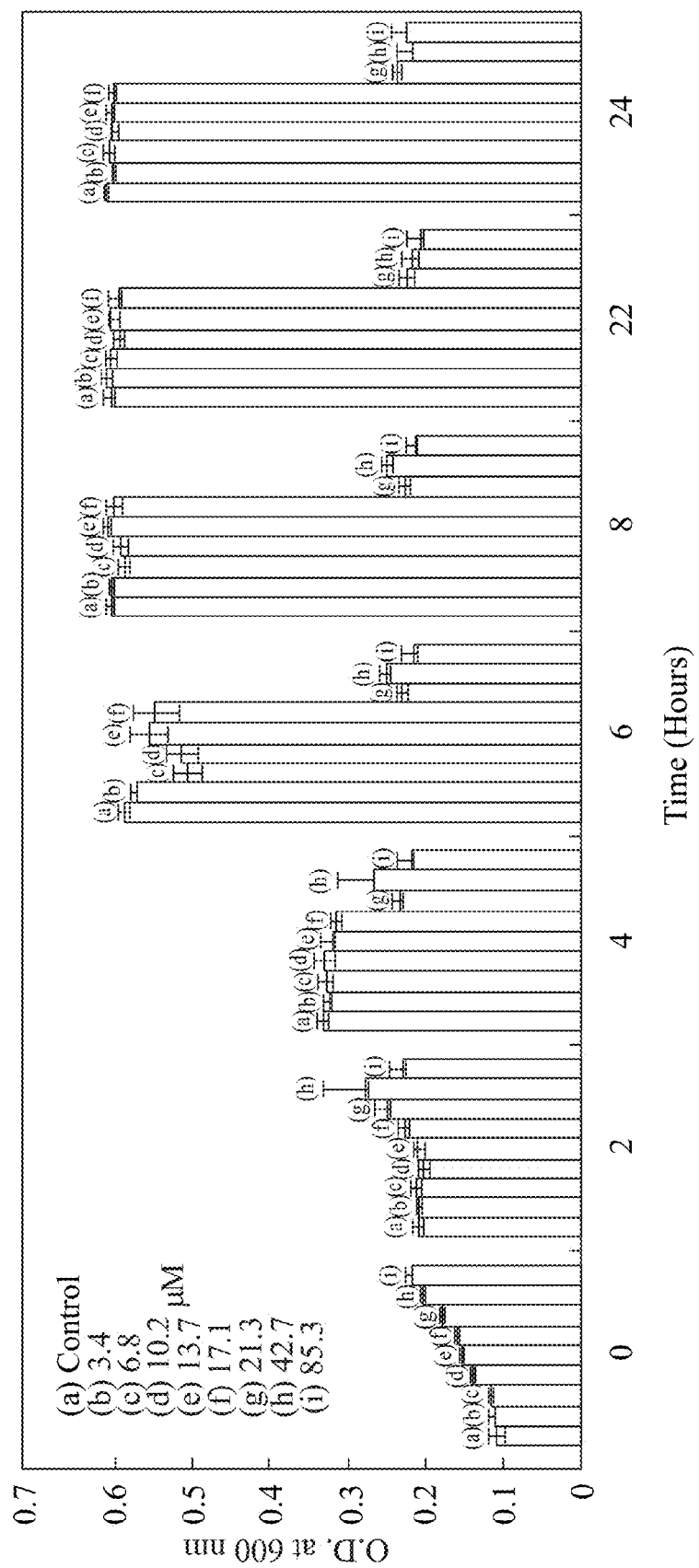
Figure 5E:
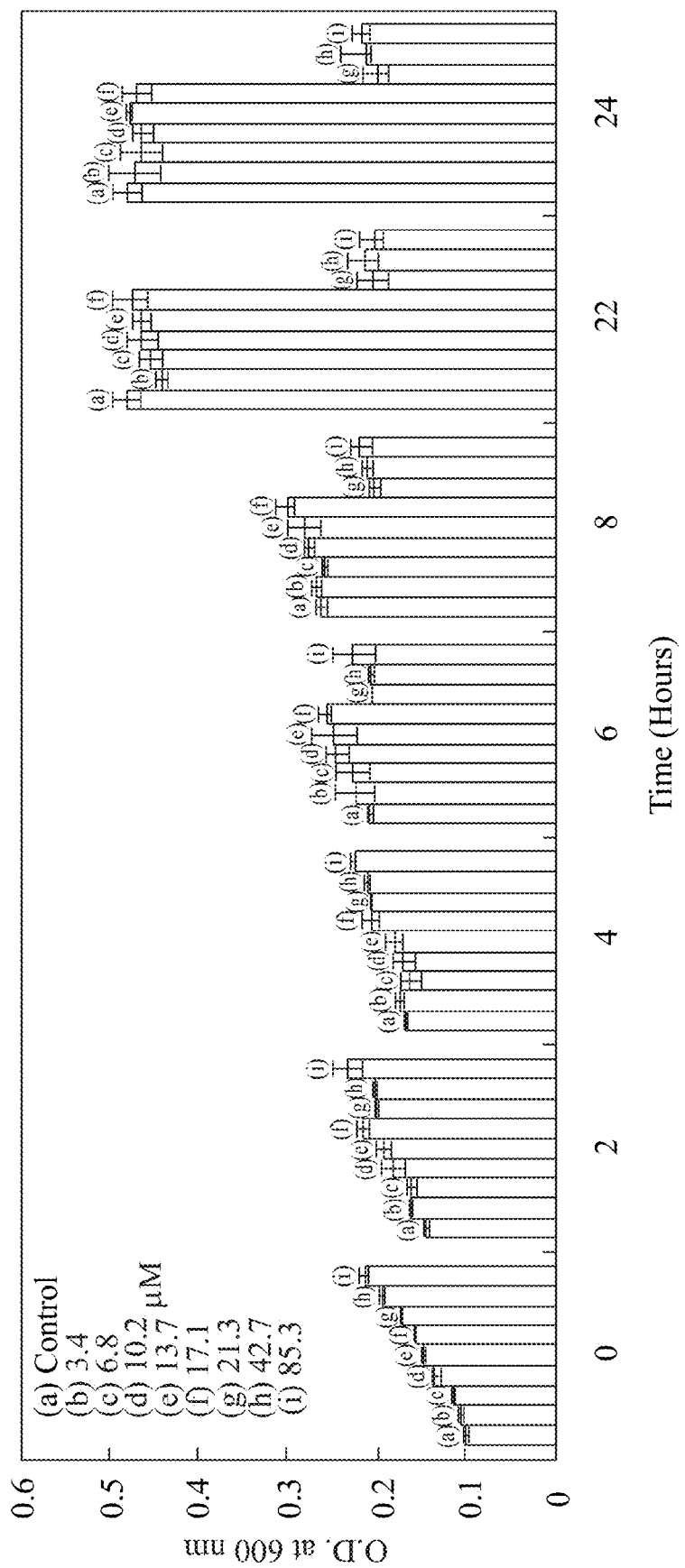
Figure 6C:
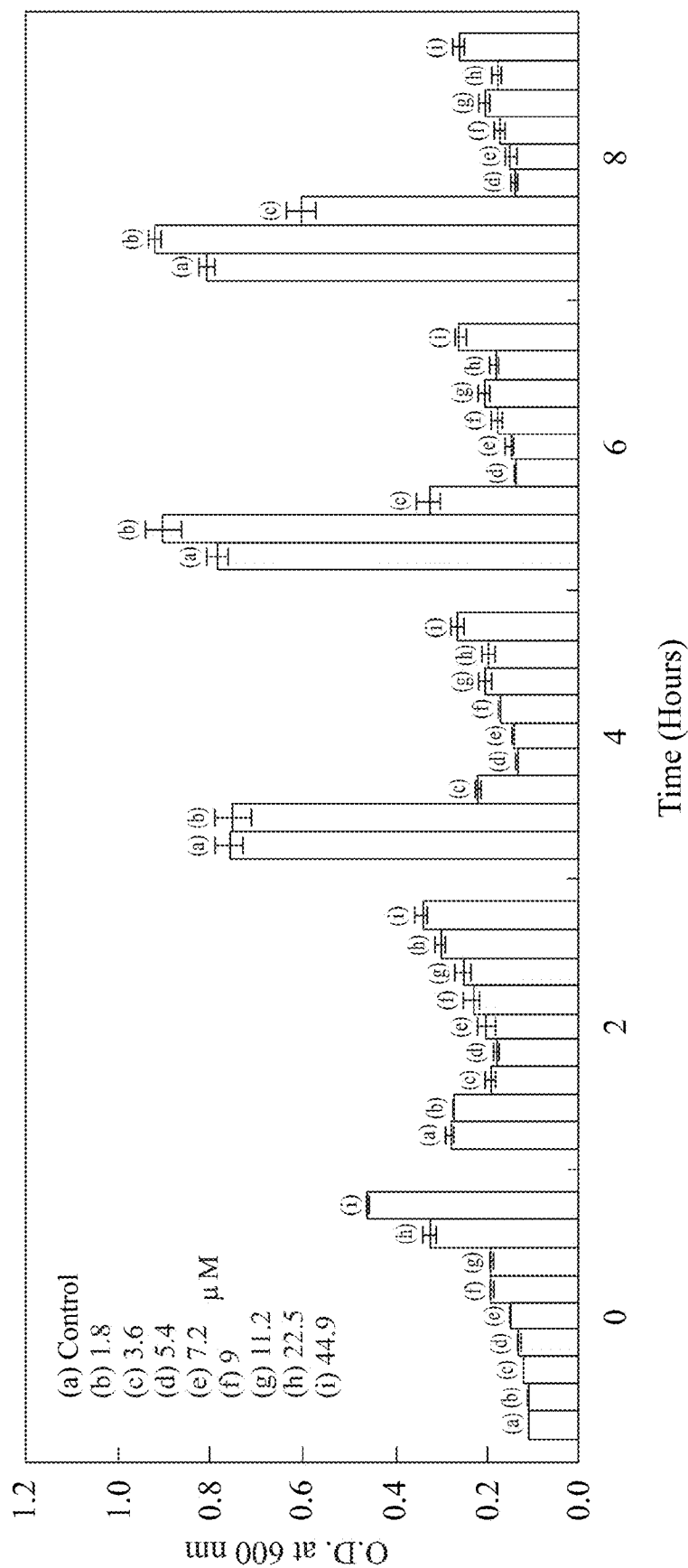
Figure 6D:
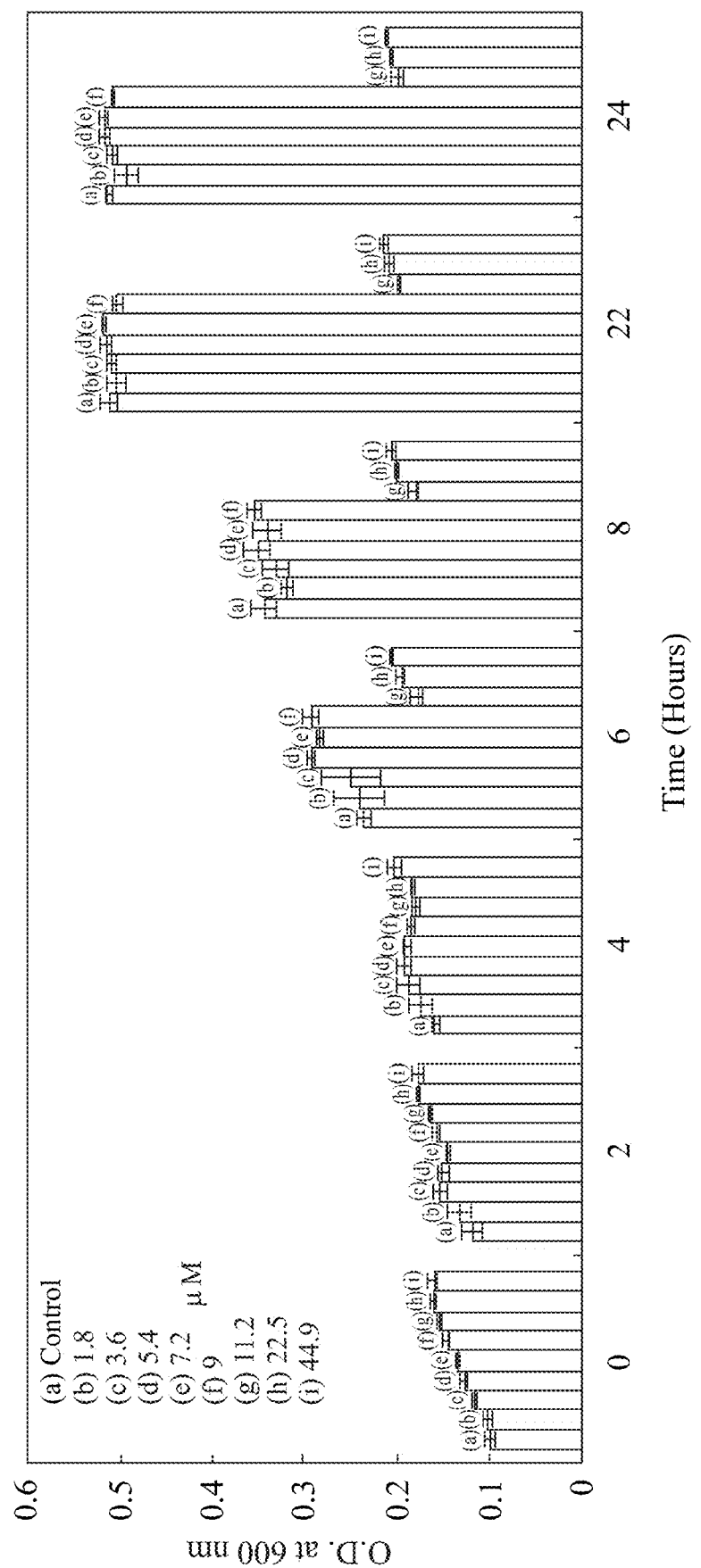
Figure 6E:
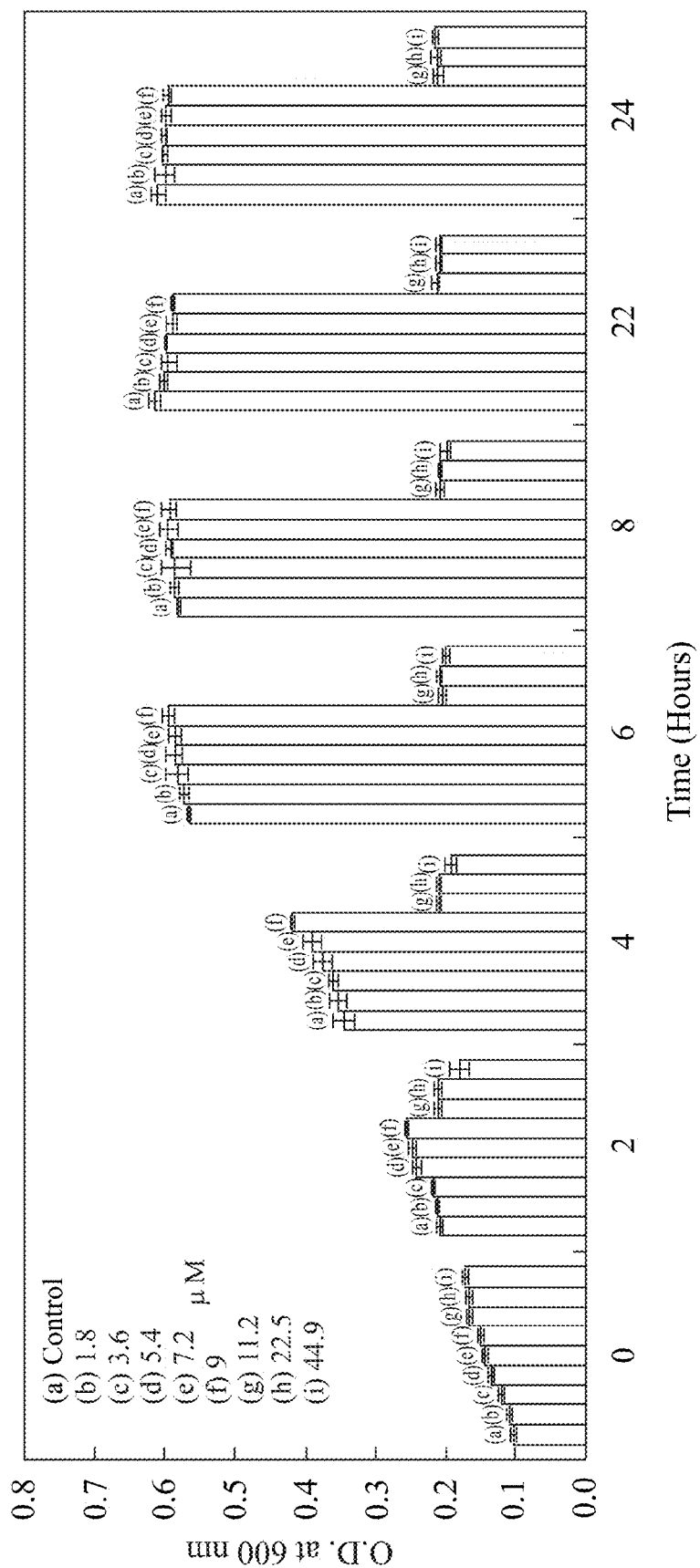

In addition, coarse grained simulation was performed to further study the micelle formation of polycarbonate in aqueous solution. The coarse grained simulation offered a microscopic understanding of the thermodynamic properties and a detailed molecular model of self-assembled micelles. The simulation results indicate the hydrophobic block assembled into the core of the spherical micelle, whereas the cationic and hydrophilic block formed the shell of the spherical micelle. TEM images of Example 3 in DI water further prove that the micelles are spherical as shown in FIG. 4. The positively charged self-assembled micelles interact with the negatively-charged surfaces of microbes via electrostatic interaction, and are readily taken up by the microbes.

Minimal inhibitory concentration (MIC) determination. The MICs of the polymers were measured using a broth microdilution method. Fifty microliters of polymer solution with a concentration ranging from about 1.0 to 500.0 micromoles/L (more specifically, 15.6, 31.3, 62.5, 125, 250, and 500 micromoles/L as shown in FIGS. 5A to 5E, and FIGS. 6A to 6E) was placed into each well of 96-well plates. The units micromoles was based on $M_n$ of the polymer. To each well was added 50 microliters of microorganism solution at a concentration that gave an optical density reading of ~0.1 to 0.2 at 600 nm. The optical density readings of microorganism solutions were measured as a function of time. The MIC was taken at the concentration, at which no growth was observed with the unaided eye and microplate reader (Bio-Teck Instruments, Inc), in the growing phase of the microorganisms. Broth containing cells alone was used as control. The tests were repeated at least three times.

Figure 7:
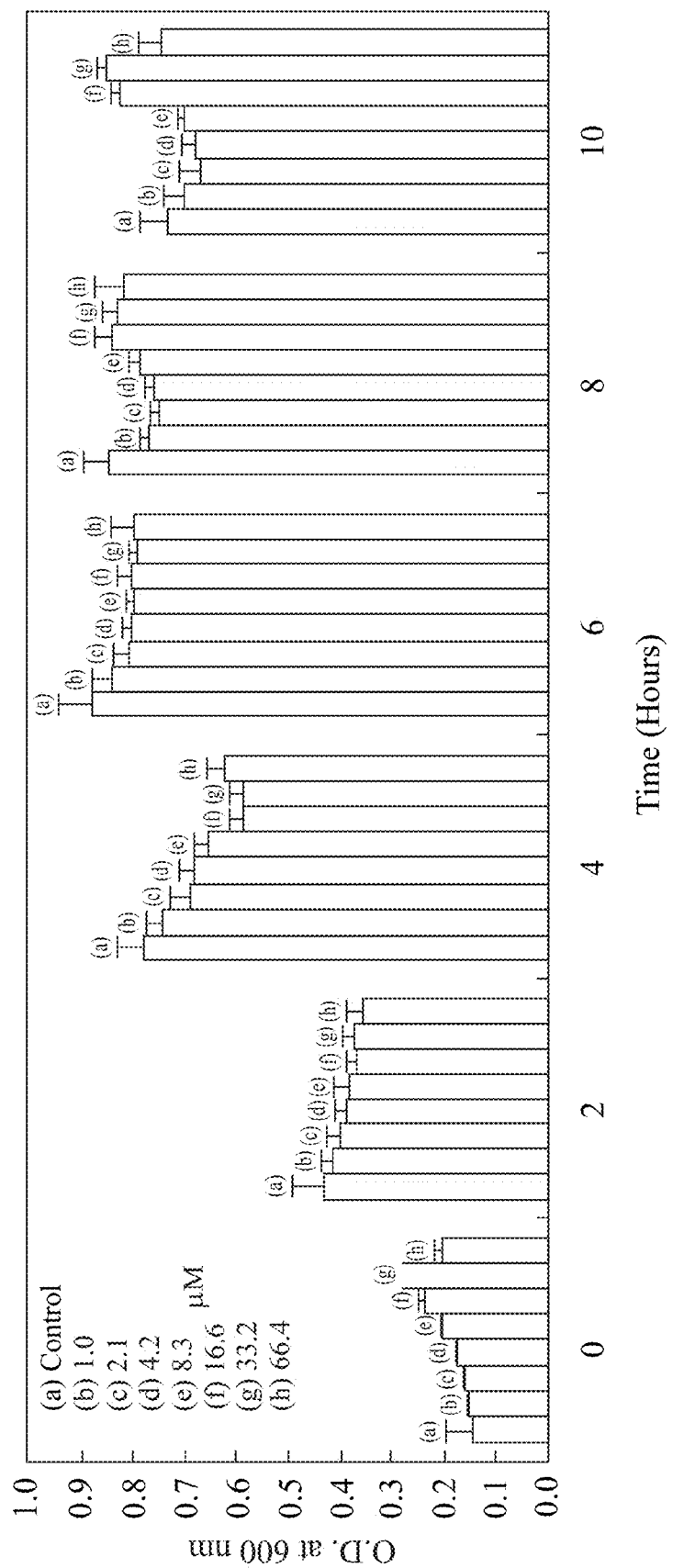
FIG. 7 is a bar chart showing the viability of Gram-positive bacteria *Bacillus subtilis* when treated with micelles formed from Example 2.

FIGS. 5A to 5E are bar charts showing the viability of Gram-positive bacteria *Bacillus subtilis, Staphylococcus aureus*, methicillin-resistant *Staphylococcus aureus* and *Enterococcus faecalis*, and the fungus *Cryptococcus neoformans*, respectively, when treated with micelles formed from Example 1. FIGS. 6A to 6E are bar charts showing the viability of Gram-positive bacteria *Bacillus subtilis, Staphylococcus aureus* and methicillin-resistant *Staphylococcus aureus*, and the fungus *Cryptococcus neoformans* as well as Gram-positive bacterium *Enterococcus faecalis*, respectively, when treated with micelles formed from Example 3. FIG. 7 is a bar chart showing the viability of Gram-positive bacteria *Bacillus subtilis* when treated with micelles formed from Example 2. Example 2 does not show a strong inhibition effect towards bacterial growth, having a MIC of higher than 66.4 micromole/L against *Bacillus subtilis* (FIG. 7). This is attributed to the polymer with the longest hydrophobic block precipitating when in contact with the growth buffer. In sharp contrast, Example 1 and Example 3 have a strong inhibitory effect on the growth of the Gram-positive and drug-resistant Gram-positive bacteria, as well as fungus. Their MIC was cell type dependent. Example 1 has MIC of 12.9, 8.6, 6.8, 21.3 and 21.3 micromole/L against *Bacillus subtilis, Staphylococcus aureus*, methicillin-resistant *Staphylococcus aureus, Enterococcus faecalis*, and *Cryptococcus neoformans*, respectively (FIGS. 5A-5E, respectively). The MICs of Example 3 against these microbes are 4.5, 6.7, 7.2, 11.2 and 11.2 micromoles/L, respectively (FIGS. 6A to 6E, respectively), which are in general lower than those for Example 1 probably due to the longer cationic block in Example 3. Thus the MICs of Examples 1 and 3 ranged from 4.5 to 21.3 micromoles/L, approximately more than 7% to 32% of the MIC of Example 2 (>66.4 micromoles/L). The MICs of Examples 1 and 3 against all of the types of the microbes tested are higher than their CMCs in the buffer (i.e., the CMC of Example 1 is 17.8 micrograms/mL, equivalent to 3.8 micromoles/L, and the CMC of Example 3 is 28.2 micrograms/mL, equivalent to 3.2 micromoles/L). Thus, at concentrations less than or equal to CMC, the polymers are not potent against bacterial growth. The formation of micelles increases the local concentration of cationic charge and polymer mass, leading to stronger interactions between the micelle and cell wall/cell membrane, which translates to effective antimicrobial activity. Adjusting hydrophobicity of either block of the copolymer can significantly enhance antimicrobial activity. For example, a hydrophobic monomer can be copolymerized into the cationic hydrophilic block to further enhance the anti-microbial activity. Alternatively, a more hydrophobic alkyl group can be incorporated into the tertiary amine group to enhance the antimicrobial activity.

Hemolysis assays. Fresh mouse red blood cells were washed with PBS three times. 100 microliters of red blood cell suspension in PBS (4% in volume) was placed in each well of 96-well plates and 100 microliters of polymer solution was added to each well. The plates were incubated for one hour at 37° C. The cell suspensions were taken out and centrifuged at 1000 g for 5 minutes. Aliquots (100 microliters) of supernatant were transferred to 96-well plates, and hemoglobin release was monitored at 576 nm using a microplate reader (Bio-Teck Instruments, Inc). The red blood cell suspension in PBS was used as negative control. Absorbance of wells with red blood cells lysed with 0.5% Triton X-100 was taken as 100% hemolysis. Percentage of hemolysis was calculated using the following formula: Hemolysis (%)= [(O.D.$_{576nm}$ in the nanoparticle solution–O.D.$_{576nm}$ in PBS)/ (O.D.$_{576nm}$ in 0.5% Triton X-100–O.D.$_{576nm}$ in PBS)]×100.

Figure 8:
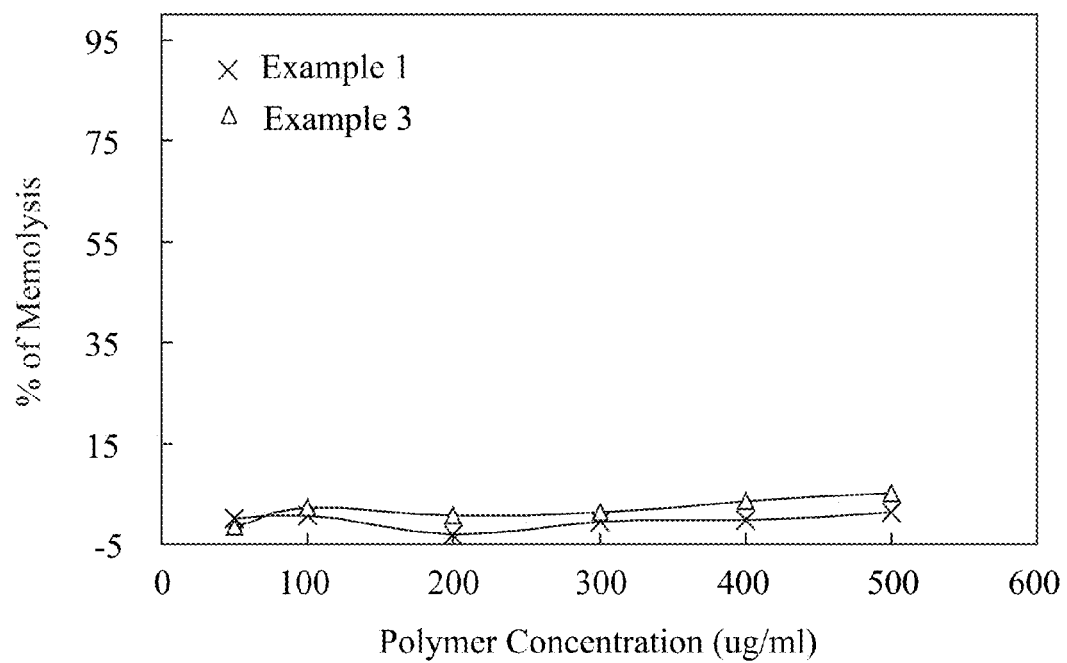
FIG. 8 is a graph of the % hemolysis as a function of concentration for Example 1 and Example 3, and shows the % hemolysis was less than 10% at all concentrations for each.

FIG. 8 is a graph of the % hemolysis as a function of concentration for Example 1 and Example 3. The polymers do not show significant hemolytic activity even at a concentration of 500 micrograms/mL (108 and 56 micromoles/L for Example 1 and 3, respectively) which is well above their MICs. The surfaces of Gram-positive bacteria and fungus are much more negatively charged than those of red blood cells. Therefore, the electrostatic interaction between the surfaces of the bacteria/fungus and cationic micelles is much stronger than that between the surfaces of the red blood cells and cationic micelles, leading to excellent antimicrobial activity, yet keeping hemolytic activity insignificant.

Transmittance electron microscopy (TEM). The morphologies of the microorganisms before and after treatment with the micelles were observed under a JEM-1230 transmittance electron microscope (JEOL, Japan) using an acceleration voltage of 80 keV. The microorganism solution (1.5 mL) was incubated with 0.5 mL of micelle solution (1000 mg/L) for 3 hours. The solution was centrifuged at 5000 rpm for 10 minutes, and the supernatant was removed. Phosphate buffer (pH 7.0, 1.5 mL) was mixed with the microorganisms, and then centrifuged at 5000 rpm for 10 minutes to remove the phosphate buffer. Phosphate buffer (pH7.0, 0.5 mL) containing 2.5% glutaraldehyde was added to the microorganisms, and incubated overnight at 4° C. for fixation. The sample was washed three times with the phosphate buffer (15 minutes each), and then post-fixed with 1% OsO4 in the phosphate buffer (pH7.0) for one hour. The fixed sample was washed three times in the phosphate buffer (15 minutes each), followed by dehydration in a graded ethanol series. The sample was incubated with the mixture of acetone and Spurr resin (1:1 in volume) for one hour at room temperature, which was then transferred to 1:3 mixture of acetone and Spun resin for 3 hours, and to Spun resin for overnight. Ultrathin sections (70-90 nm) were cut using a Reichert-Jung Ultracut E ultramicrotome, and post-stained with uranyl acetate and lead citrate for 15 minutes each prior to TEM observations. TEM image of the micelles were obtained using a FEI Tecnai G2 F20 electron microscope with an acceleration voltage of 200 keV. To prepare the TEM sample, several drops of the micelle solution were placed on a formvar/carbon coated 200 mesh copper grid and left to dry under room temperature.

Figure 9:
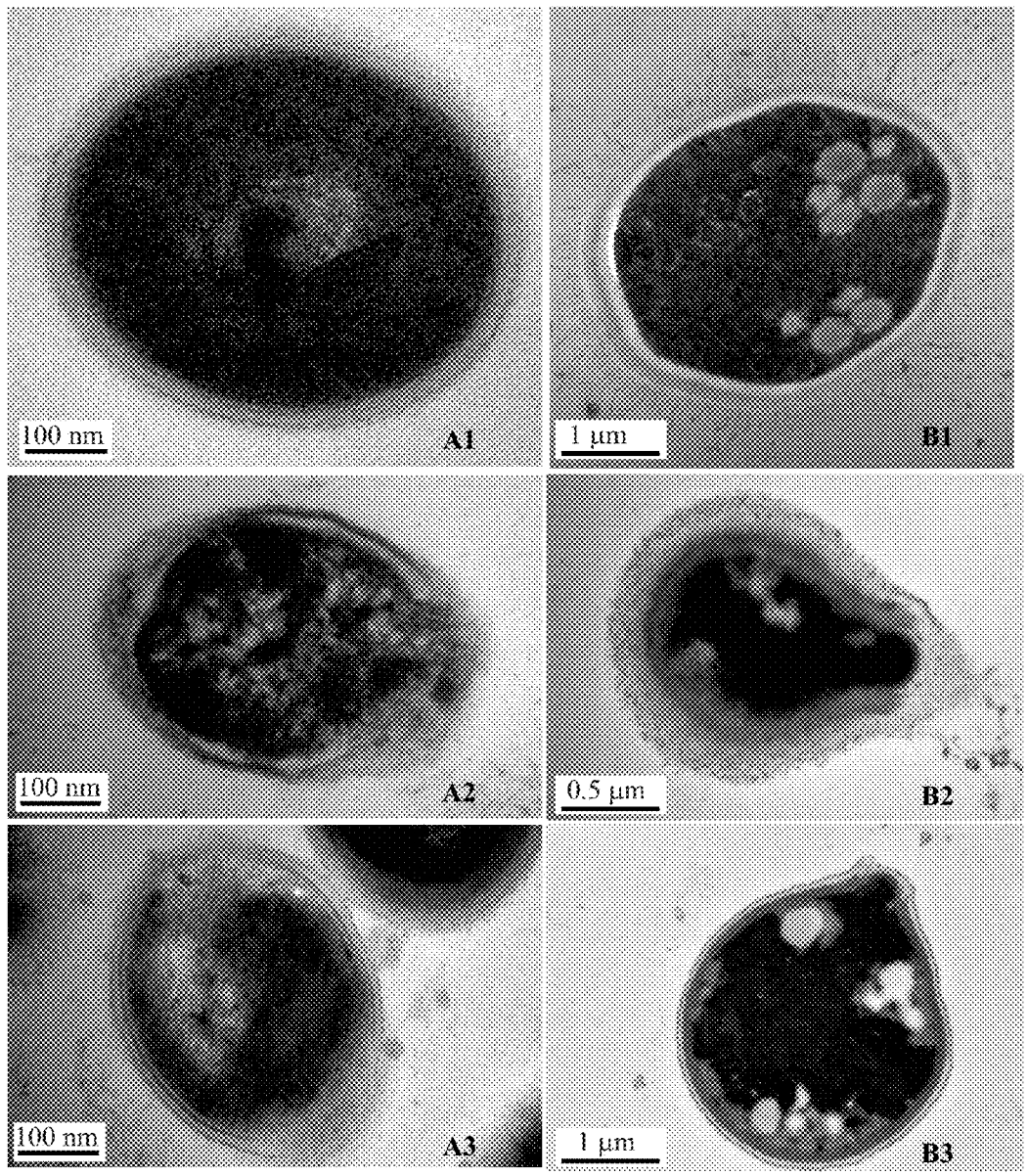
FIG. 9 is a set of TEM images following over a 3 hour period the morphological changes of *Enterococcus faecalis* (TEM images labeled A1, A2, and A3) and *Cryptococcus neoformans* (labeled B1, B2 and B3). TEM images labeled A1 and B1 are before incubation. TEM images labeled A2 and B2 are after incubation with Example 1 at a lethal dose (1000 mg/L). TEM images labeled A3 and B3 are after incubation with Example 3 at a lethal dose (1000 mg/L). As shown in TEM images labeled A2 and A3 of FIG. 9, the cell wall and membrane of the microorganisms were disrupted, and cell lysis was observed after the treatment with the micelles. The burst of cytoplast was also observed from the damaged cell wall and membrane of the microorganisms as shown in TEM images labeled B2 and B3 of FIG. 9 after the treatment with the micelles.

Using the above procedure the mechanism of antimicrobial behavior of the micelles was studied by TEM. FIG. 9 is a set of TEM images following over a 3 hour period the morphological changes of *Enterococcus faecalis* (TEMs labeled A1, A2, and A3) and *Cryptococcus neoformans* (TEMs labeled B1, B2, and B3). TEM images labeled A1 and B1 are before incubation. TEM images labeled A2 and B2 are after incubation with Example 1 at a lethal dose (1000 mg/L). TEM images labeled A3 and B3 are after incubation with Example 3 at a lethal dose (1000 mg/L). As shown in FIG. 9 images A2 and A3, the cell wall and membrane of the microorganisms were disrupted, and cell lysis was observed after the treatment with the micelles. The burst of cytoplast was also observed from the damaged cell wall and membrane of the microorganisms as shown in TEM images labeled B2 and B3 of FIG. 9 after the treatment with the micelles. Thus, the cationic micelles formed from Examples 1 and 3 readily interact with the negatively-charged cell wall through electrostatic interaction. The steric hindrance imposed by the mass of micelles in the cell wall and electrostatic interaction between the cationic micelle and the cell wall, inhibit cell wall synthesis and/or damage the cell wall, resulting in cell lysis. In addition, the micelles can easily permeate the cytoplasmic membrane of the organisms due to the presence of the relatively large volume of the micelles, thus destabilizing the membrane based on electroporation and/or a sinking raft model, and leading to cell death.

II. Antimicrobial Polymers with Shape-Persistent Moiety.

Preparation of bis(4-aminobenzyl)terephthalamide (BAMT)

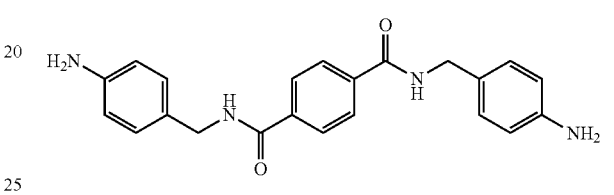

(BAMT)

To a schlenk tube were placed poly(ethylene terephthalate) (PET) flakes (1.92 g, 3 mm×3 mm; obtained from recycled PET drink bottles), p-aminobenzylamine (3.5 mL, 30.8 mmol), 1,5,7-Triazabicyclo[4.4.0]dec-5-ene (TBD: 147 mg, 1.1 mmol), and a stir bar. The inhomogeneous mixture was heated at 120° C. for 20 hours under nitrogen atmosphere and allowed to cool down to room temperature. Unreacted excess amine was washed out of the crude product with ethyl acetate and THF several times. The residue was dried in vacuum to yield BAMT clean enough to use the next step (2.57 g, 69%). $^1$H NMR (400 MHz, DMSO-d$_6$): delta 8.97 (t, 2H; NH), 7.93 (s, 4H; Ph), 6.99 (d, 2H; Ph), 6.51 (d, 2H; Ph), 4.97 (s, 4H; NH$_2$), 4.30 (d, 4H; CH$_2$). $^{13}$C NMR (125 MHz, DMSO-d$_6$): delta 165.4, 147.6, 136.7, 128.4, 127.3, 126.4, 113.8, 42.5.

Preparation of bis(4-aminophenyl)terephthalamide (BAPT)

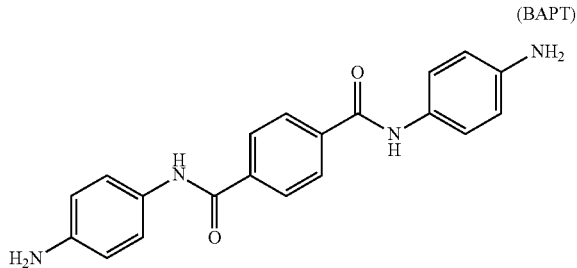 [SMILES: Nc1ccc(NC(=O)c2ccc(C(=O)Nc3ccc(N)cc3)cc2)cc1]

(BAPT)

To a schlenk tube were placed PET flakes (1.96 g), p-phenylenediamine (3.42 g, 33.5 mmol), TBD (143 mg, 1.0 mmol), and a stir bar. The inhomogeneous mixture was heated at 160° C. for 66 hours under nitrogen atmosphere and allowed to cool down to room temperature. Unreacted excess amine was washed out of the crude product with ethyl acetate and THF several times. The residue was dried in vacuum to yield BAPT clean enough to use the next step (2.42 g, 68%). $^1$H NMR (400 MHz, DMSO-d$_6$): delta 10.0 (s, 2H; NH), 8.02 (s, 4H; Ph), 7.39 (d, 2H; Ph), 6.55 (d, 2H; Ph), 5.00 (s, 4H; NH$_2$). $^{13}$C NMR (125 MHz, DMSO-d$_6$): delta 164.0, 145.4, 137.4, 127.9, 127.4, 122.3, 113.7.

Preparation of bis(4-(3-(5-hydroxypentyl)ureido)benzyl)terephthalamide (HPUBT)

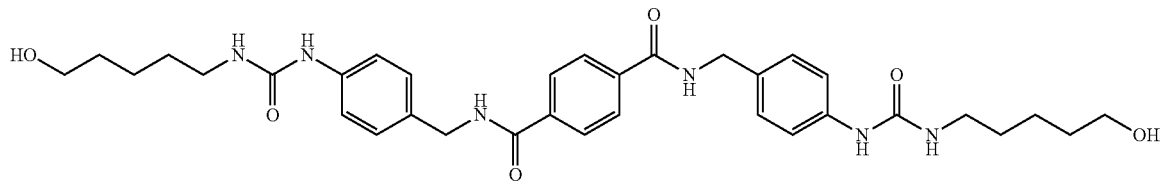
(HPUBT)

To a DMF solution (4 mL) of bis(pentafluorophenyl)carbonate (1.0 g, 2.53 mmol) was added a solution of BAMT (0.37 g, 1.0 mmol) in DMF (4 mL). The reaction mixture was stirred for 1 hour at room temperature, 5-amino-1-pentanol (0.45 mL, 4.15 mmol) was added, and the mixture was kept stirring for additional 2 hours. Methanol (200 mL) was added to the mixture to stir for 3 h where only the product was precipitated. The precipitate was then filtered and dried in vacuum at 80° C. to give HPUBT as a yellowish solid (0.56 g, 89%). $^1$H NMR (400 MHz, DMSO-$d_6$): delta 9.09 (t, 2H; PhNH), 8.37 (s, 2H; PhCONH), 7.95 (s, 4H; Ph), 7.32 (d, 4H; Ph), 7.17 (d, 4H; Ph), 6.08 (t, 2H; NHCH$_2$), 4.43-4.34 (m, 6H; PhCH$_2$NH and OH), 3.38 (q, 4H; CH$_2$OH), 3.05 (q, 4H; NHCH$_2$CH$_2$), 1.47-1.35 (m, 8H; CH$_2$), 1.34-1.23 (m, 4H; CH$_2$). $^{13}$C NMR (125 MHz, DMSO-$d_6$): delta 165.4, 155.1, 139.3, 136.6, 131.8, 127.7, 127.2, 117.4, 60.6, 42.3, 32.2, 29.6, 22.9

Preparation of bis(4-(3-(5-hydroxypentyl)ureido)phenyl)terephthalamide (HPUPT)

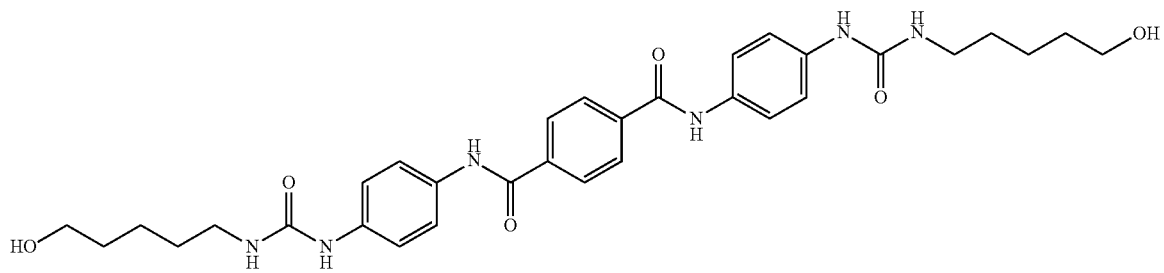
(HPUPT)

This compound was obtained by the same procedure as used for HPUBT using BAPT instead of BAMT. The product was yielded as a grey solid (0.44 g, 72%). $^1$H NMR (400 MHz, DMSO-$d_6$): delta 10.3 (s, 2H; PhNH), 8.39 (s, 2H; PhCONH), 8.06 (s, 4H; Ph), 7.63 (d, 4H; Ph), 7.37 (d, 4H; Ph), 6.10 (t, 2H; NHCH$_2$), 4.38 (t, 2H; OH), 3.40 (q, 4H; CH$_2$OH), 3.07 (q, 4H; CH$_2$NH), 1.50-1.36 (m, 8H; CH$_2$), 1.36-1.25 (m, 4H; CH$_2$). $^{13}$C NMR (125 MHz, DMSO-$d_6$): delta 164.3, 155.2, 137.4, 136.8, 132.4, 127.5, 121.1, 117.7, 60.6, 32.2, 29.7, 22.9.

Preparation of HPUBT-[P(LLA)]$_2$. ROP of L-Lactide (LLA) Initiated by HPUBT

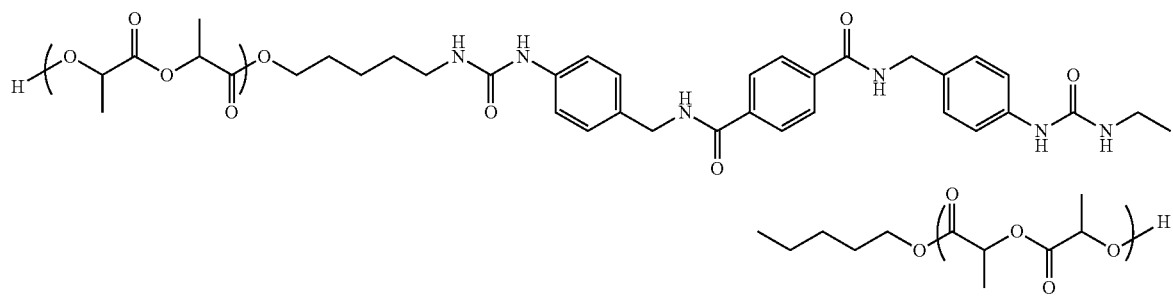
HPUBT-[P(LLA)]$_2$

In the globe box, HPUBT (63 mg, 0.10 mmol) and 1,8-diazabicyclo[5.4.0]undec-7-ene (DBU; 1.7 mg, 0.01 mmol) were dissolved in dry DMSO (1.0 mL) and allowed to be homogeneous with slight heating. A solution (1.0 mL) of L-lactide (302 mg, 2.1 mmol) and N-(3,5-bis(trifluoromethyl)phenyl-N'-cyclohexylthiourea (TU; 37 mg, 0.1 mmol) was combined to the initiator/catalyst solution and the mixture was stirred for 5 hours at room temperature ([LA]/[HPUBT]=21, ~80% conversion), quenched by adding benzoic acid (11.6 mg, 0.09 mmol), and precipitated in 2-propanol (240 mg, 66%). GPC (THF, PS standard): $M_n$=6100, PDI=1.09. $^1$H NMR (400 MHz, DMSO-$d_6$): delta 9.08 (t, 2H; PhNH), 8.37 (s, 2H; CONH), 7.95 (s, 4H; Ph), 7.32 (d, 4H; Ph), 7.17 (d, 4H; Ph), 6.09 (t, 2H; NHCH$_2$), 5.26-5.05 (m, ~40H; CH$_{PLA}$), 4.39 (d, 4H; NHCH$_2$), 4.20 (q, 2H; CH$_{PLA\ end\ group}$), 4.14-4.02 (m, 4H; CH$_2$O), 3.05 (q, 4H; NHCH$_2$), 1.66-1.53 (m, 4H; CH$_2$), 1.53-1.35 (m, ~124H; CH$_3$ $_{PLA}$ and CH$_2$), 1.36-1.23 (m, 10H; CH$_2$ and CH$_3$ $_{PLA\ end\ group}$).

Preparation of HPUPT-[P(LLA)]$_2$. ROP of L-lactide Initiated by HPUPT

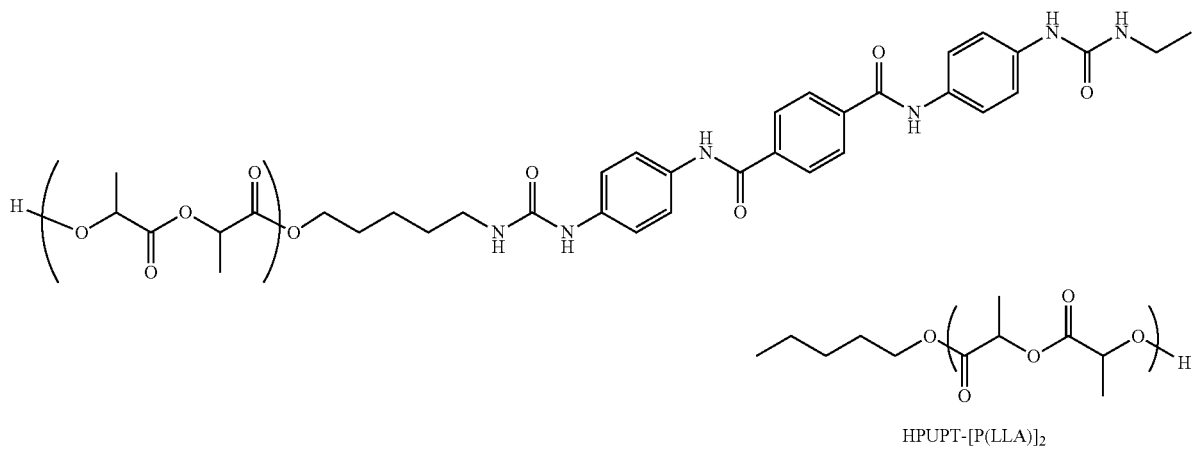

HPUPT-[P(LLA)]$_2$

The ROP was carried out by the same procedure as described for HPUBT-P(LLA) using HPUPT instead of HPUBT (~90% conversion, 237 mg, 65%). GPC (THF, PS standard): $M_n$=5900, PDI=1.22. $^1$H NMR (400 MHz, DMSO-$d_6$): delta 10.3 (s, 2H; PhNH), 8.39 (s, 2H; CONH), 8.06 (s, 4H; Ph), 7.62 (d, 4H; Ph), 7.37 (d, 4H; Ph), 6.12 (s, 2H; NHCH$_2$), 5.21-5.19 (m, ~40H; CH$_{PLA}$), 4.26-4.02 (m, 6H; CH$_{PLA\ end\ group}$ and CH$_2$O), 3.07 (q, 4H; NHCH$_2$), 1.67-1.55 (m, 4H; CH$_2$), 1.54-1.37 (m, ~124H; CH$_3$ $_{PLA}$ and CH$_2$), 1.37-1.23 (m, 10H; CH$_2$ and CH$_3$ $_{PLA\ end\ group}$).

Preparation of Acetyl Endcapped Precursor Block Copolymer HPUBT-[P(LLA)$_{n/2}$-b-P(MTCO-PrBr)$_{m/2}$Ac]$_2$

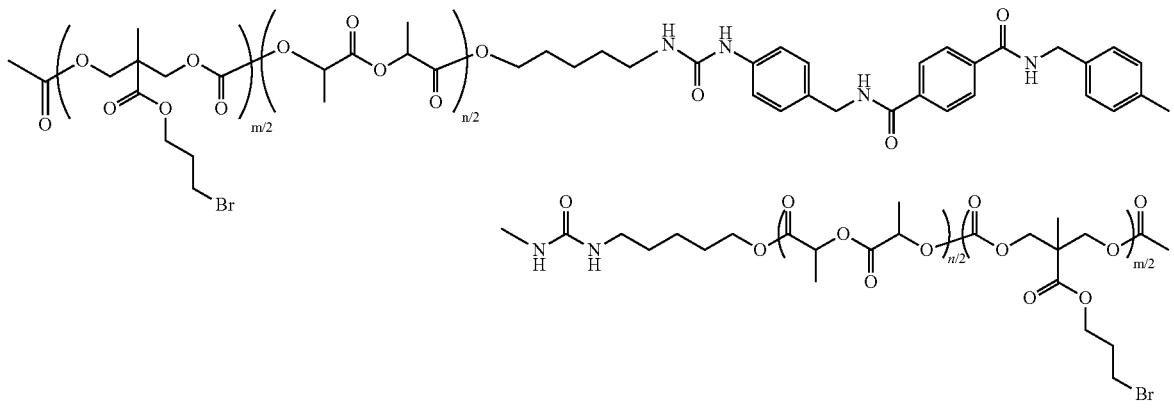

H HPUBT-[P(LLA)$_{n/2}$-b-P(MTCOPrBr)$_{m/2}$Ac]$_2$

A first block copolymer was formed by initiating ROP of 2-(3-bromopropyl)oxycarbonyl-2-methyl trimethylenecarbonate (MTCOPrBr) using HPUBT-[P(LLA)]$_2$. The first block copolymer was endcapped with acetyl groups. Thus, HPUBT-[P(LLA)]$_2$ (155 mg, [OH]=0.08 mmol), MTCOPrBr (282 mg, 1.0 mmol), TU (10.5 mg, 0.03 mmol) were dissolved in dry methylene chloride (2.0 mL) and transferred to a vial containing DBU (3.8 mg, 0.02 mmol) to conduct ROP at room temperature for 2.5 hours in the globe box ([MTCOPrBr]/[OH]=12). Acetic anhydride (59 mg, 0.6 mmol) was added to the mixture in order both to quench the reaction and to cap the terminal hydroxyl groups (~90% conversion). The mixture was stirred for 60 h, precipitated in cold methanol, isolated, and dried in vacuum for 20 hours to yield the above precursor block copolymer HPUBT-[P(LLA)-b-P(MTCOPrBr)Ac]$_2$ (390 mg, 89%). GPC (THF, PS standard): $M_n$=9400, PDI=1.23. $^1$H NMR (400 MHz, DMSO-d$_6$): delta 9.08 (t, 2H; PhNH), 8.39 (s, 2H; CONH), 7.95 (s, 4H; Ph), 7.32 (d, 4H; Ph), 7.16 (d, 4H; Ph), 6.12 (s, 2H; NHCH$_2$), 5.26-5.02 (m, ~40H; CH$_{PLA}$), 4.39 (d, 4H; NHCH$_2$), 4.33-4.00 (m, ~144H; CH$_2$O$_{PCBP}$ and CH$_2$O), 3.58-3.49 (m, ~45H; CH$_2$Br$_{PCBP}$), 3.05 (q, 4H; NHCH$_2$), 2.16-2.04 (m, ~49H; CH$_{2\ PCBP}$ and CH$_{3\ end\ group}$), 1.64-1.53 (m, 4H; CH$_2$), 1.52-1.35 (m, ~130H; CH$_{3\ PLA}$ and CH$_2$), 1.36-1.26 (m, 4H; CH$_2$), 1.23-1.13 (s, ~70H; CH$_{3\ PCBP}$).

Preparation of Acetyl Endcapped Precursor Block Copolymer HPUPT-[P(LLA)-b-P(MTCOPrBr)Ac]$_2$

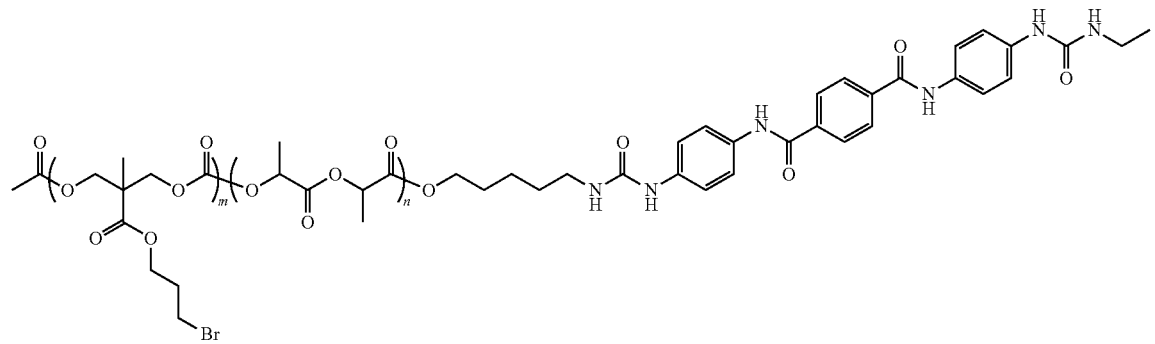

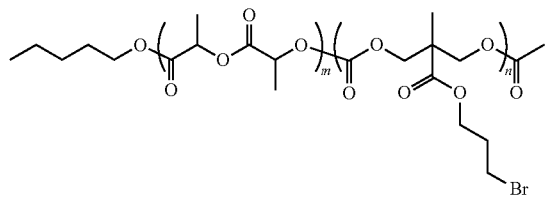

HPUPT-[P(LLA)$_{n/2}$-b-P(MTCOPrBr)$_{n/2}$Ac]$_2$

A first block copolymer was formed by initiating ROP of 2-(3-bromopropyl)oxycarbonyl-2-methyl trimethylenecarbonate (MTCOPrBr) from HPUPT-[P(LLA)]$_2$. This precursor block copolymer is endcapped with acetyl groups. The ROP was carried out by the same procedure as described above for HPUBT-[P(LLA)-b-P(MTCOPrBr)Ac]$_2$ using HPUPT-[P(LLA)]$_2$ as an initiator instead of HPUBT-[P(LLA)]$_2$ (~88% conversion, 324 mg, 74%). GPC (THF, PS standard): $M_n$=9900, PDI=1.26. $^1$H NMR (400 MHz, DMSO-d$_6$): delta 10.2 (s, 2H; PhNH), 8.44 (s, 2H; CONH), 8.06 (s, 4H; Ph), 7.62 (d, 4H; Ph), 7.37 (d, 4H; Ph), 6.17 (s, 2H; NHCH$_2$), 5.25-5.00 (m, ~40H; CH$_{PLA}$), 4.35-4.03 (m, ~151H; CH$_2$O$_{PCBP}$ and CH$_2$O), 3.58-3.47 (m, ~49H; CH$_2$Br$_{PCBP}$), 3.07 (q, 4H; NHCH$_2$), 2.16-2.04 (m, ~48H; CH$_{2\ PCBP}$ and CH$_{3\ end\ group}$) 1.67-1.55 (m, 4H; CH$_2$), 1.52-1.36 (m, ~128H; CH$_{3\ PLA}$ and CH$_2$), 1.36-1.28 (m, 4H; CH$_2$), 1.23-1.12 (s, ~75H; CH$_{3\ PCBP}$).

Example 4

Quaternization of HPUBT-[P(LLA)-b-P(MTCOPrBr)Ac]$_2$

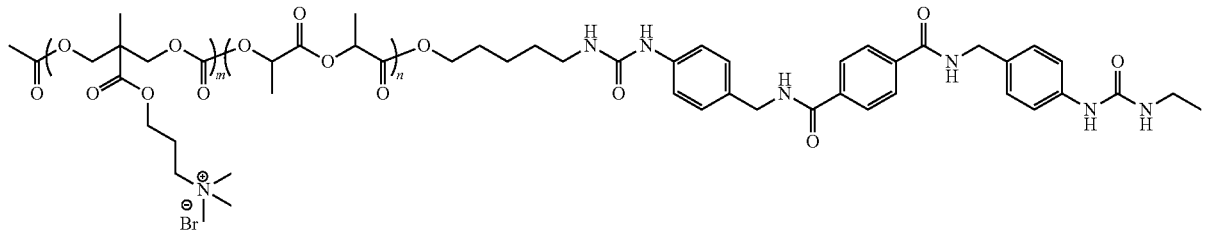

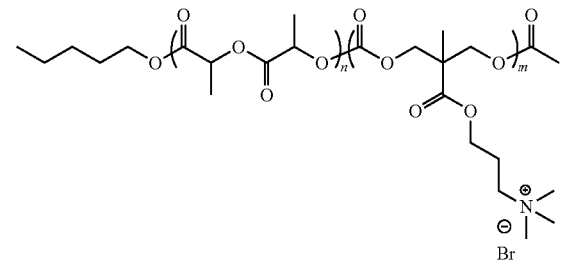

HPUBT-[P(LLA)$_{n/2}$-b-P(MTCOPrBr$_{m/2}$*NMe$_3$)Ac]$_2$

Trimethylamine gas (274 mg, 4.6 mmol) was charged to a mixed solution of acetonitrile and DMF (4+2 mL) of HPUBT-[P(LLA)$_{n/2}$-b-P(MTCOPrBr)$_{m/2}$Ac]$_2$ (390 mg, [Br]=0.9 mmol) immersed in a dry-ice/acetone bath. The solution was then allowed to warm to room temperature and kept stirring for 18 h before acetonitrile and excess gasses were removed under vacuum. The concentrated residue was precipitated in THF, isolated, and dried in vacuum to give the cationic block copolymer HPUBT-[P(LLA)$_{n/2}$-b-P(MTCOPrBr$_{m/2}$*NMe$_3$)Ac]$_2$, referred to below as Example 4 (324 mg, 73%). n=10, m=12 in the above formula. The "*" after MTCOPrBr in the formula indicates the NMe$_3$ forms a quaternary salt with the halide containing repeat unit formed by MTCOPrBr. $^1$H NMR (400 MHz, DMSO-d$_6$): delta 9.09 (s, 2H; PhNH), 8.43 (s, 2H; CONH), 7.95 (s, 4H; Ph), 7.32 (d, 4H; Ph), 7.16 (d, 4H; Ph), 6.16 (s, 2H; NHCH$_2$), 5.27-5.02 (m, ~40H; CH$_{PLA}$), 4.44-4.00 (m, ~166H; NHCH$_2$, CH$_2$O$_{PCPAB}$ and CH$_2$O), 3.52-3.38 (m, ~52H; CH$_2$N$^+$$_{PCPAB}$), 3.22-2.99 (m, ~234H; N$^+$CH$_3$ $_{PCPAB}$ and NHCH$_2$), 2.14-1.96 (m, ~51H; CH$_2$ $_{PCPAB}$ and CH$_3$ $_{end\ group}$), 1.66-1.53 (m, 4H; CH$_2$), 1.53-1.35 (m, ~117H; CH$_3$ $_{PLA}$ and CH$_2$), 1.33-1.25 (m, 4H; CH$_2$), 1.26-1.14 (s, ~80H; CH$_3$ $_{PCPAB}$). 97% quaternized; M$_n$=12,000 g/mol (NMR).

Example 5

Quaternization of HPUPT-[P(LLA)-b-P(MTCOPrBr)Ac]$_2$

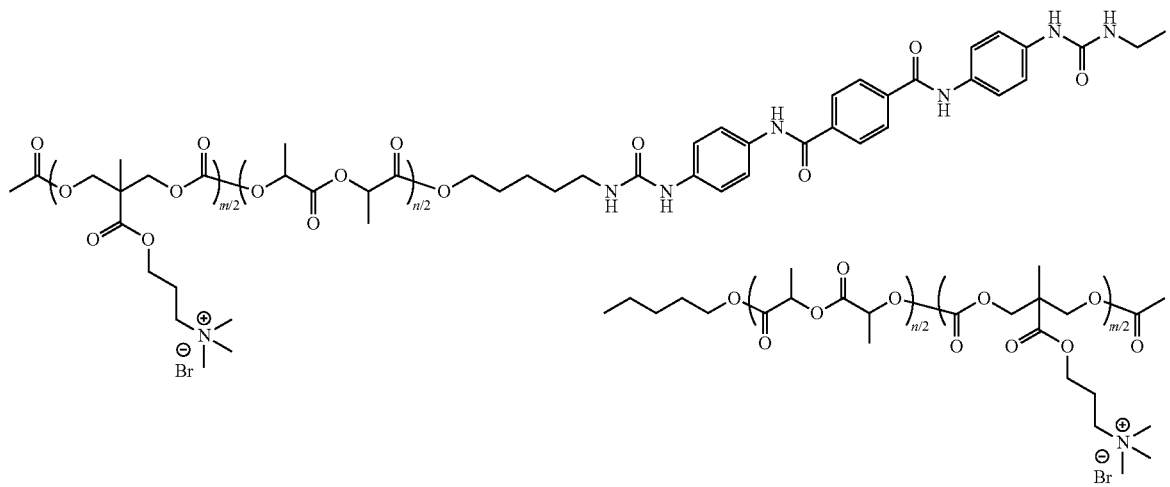

HPUPT-[P(LLA)$_{n/2}$-b-P(MTCOPrBr)$_{m/2}$*NMe$_3$)Ac]$_2$

Trimethylamine gas (246 mg, 4.2 mmol) was charged to a mixed solution of acetonitrile and DMF (4+2 mL) of HPUPT-[P(LLA)-b-P(MTCOPrBr)Ac]$_2$ (324 mg, [Br]=0.8 mmol) immersed in a dry-ice/acetone bath. The solution was then allowed to warm to room temperature and kept stirring for 18 hours before acetonitrile and excess gasses were removed under vacuum. The concentrated residue was precipitated in THF, isolated, and dried in vacuum to give the cationic block copolymer HPUPT-[P(LLA)-b-P(MTCOPrN$^+$Me$_3$Br$^-$)Ac]$_2$, referred to below as Example 5 (314 mg, 85%). n=10, m=12 in the above formula. $^1$H NMR (400 MHz, DMSO-d$_6$): delta 10.3 (s, 2H; PhNH), 8.46 (s, 2H; CONH), 8.07 (s, 4H; Ph), 7.63 (d, 4H; Ph), 7.37 (d, 4H; Ph), 6.19 (s, 2H; NHCH$_2$), 5.35-5.01 (m, ~40H; CH$_{PLA}$), 4.56-4.00 (m, ~137H; CH$_2$O$_{PCPAB}$ and CH$_2$O), 3.59-3.43 (m, ~59H; CH$_2$N$^+$$_{PCPAB}$), 3.28-3.02 (m, ~208H; N$^+$CH$_3$ $_{PCPAB}$ and NHCH$_2$), 2.16-1.99 (m, ~52H; CH$_2$ $_{PCPAB}$ and CH$_3$ $_{end\ group}$) 1.66-1.55 (m, 4H; CH$_2$), 1.55-1.37 (m, ~114H; CH$_3$ $_{PLA}$ and CH$_2$), 1.36-1.15 (m, ~79H; CH$_2$ and CH$_3$ $_{PCBAB}$). 93% quaternized; M$_n$=11800 g/mol (NMR).

The properties of cationic block copolymer Examples 4 and 5 are shown in Table 9.

of Example 4 micelles is 67 and 57 mV at 1000 and 3000 mg/L respectively, and that of Example 5 spherical micelles is 69 mV at 1000 mg/L.

Figure 12:
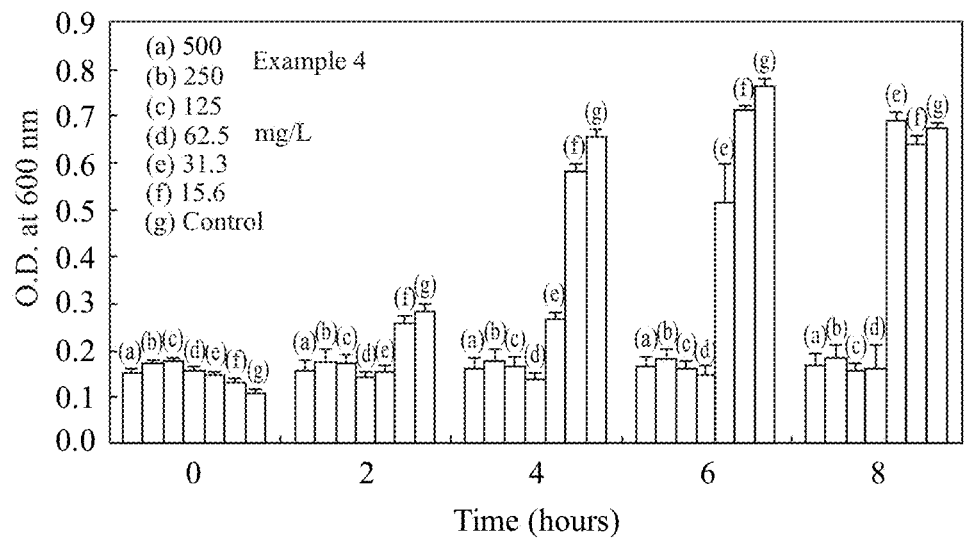
FIG. 12 is a bar chart showing the viability of Gram-positive bacteria *Bacillus subtilis* when treated with various concentrations of micelles formed from Example 4.
Figure 13:
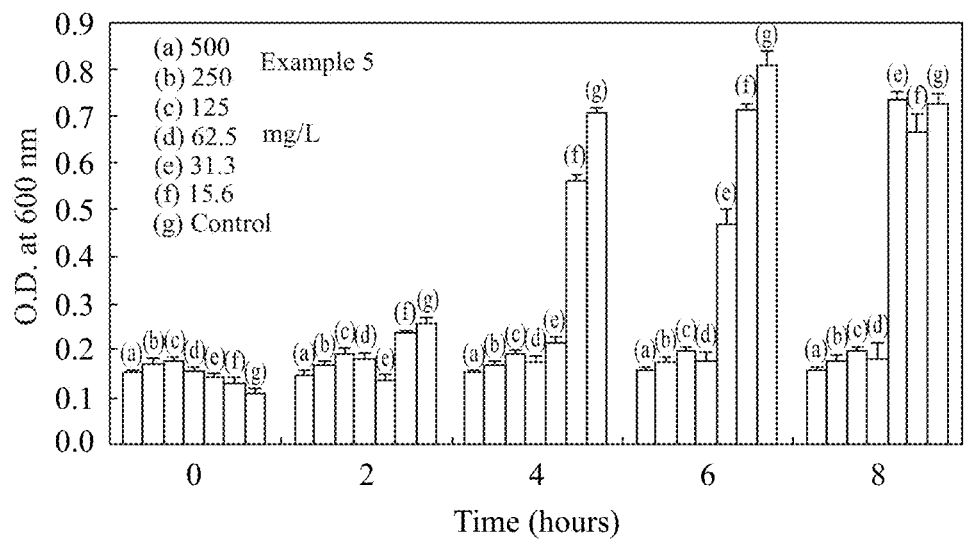
FIG. 13 is a bar chart showing the viability of Gram-positive bacteria *Bacillus subtilis* when treated with various concentrations of micelles formed from Example 5.
Figure 14:
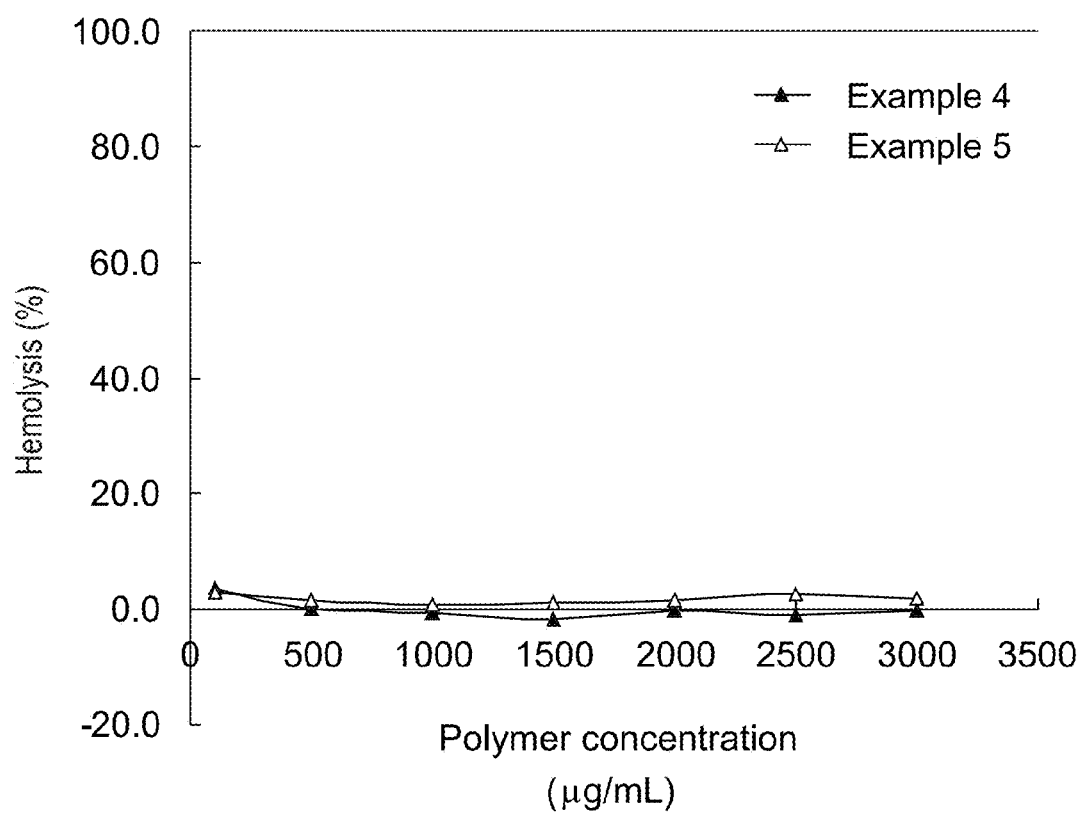
FIG. 14 is a graph of the % hemolysis as a function of concentration for Example 4 and Example 5, and shows the % hemolysis was less than 10% up to a concentration of 3000 mg/L, which is well above the MIC, which is 62.5 mg/L for each of Example 4 and Example 5.

Example 4 (FIG. 12) and Example 5 (FIG. 13) kill *Bacillus subtilis* efficiently, and their MIC values are the same, which is 62.5 mg/L. Importantly, they do not cause hemolysis up to a concentration of 3000 mg/L (FIG. 14), which is well above the MIC. Thus, these cationic block polymers comprising a shape-persistent moiety can be a promising antimicrobial agent due to their non-toxicity and strong antimicrobial activities.

The micelles formed with the cationic block copolymer Examples 1 to 5 have an average particle size of from about 20 nm to about 402 nm, and a have a MIC of about 4 micromoles/L to about 66 micromoles/L, wherein moles are based on M$_n$ of the cationic block copolymer. The CMC of Examples 1 to 3 is about 15 micrograms/mL to about 70.8 micrograms/mL.

TABLE 9

|  | Polymer | PDI | m:n | M$_n$ (g/mol) | CMC micrograms/mL in DI | Size (nm) | Zeta Potential |
|---|---|---|---|---|---|---|---|
|  | HPUBT-[P(LLA)]$_2$ | 1.09 |  | 6100 |  |  |  |
|  | HPUPT-[P(LLA)]$_2$ | 1.22 |  | 5900 |  |  |  |
|  | HPUBT-[P(LLA)-b-P(MTCOPrBr)Ac]$_2$ | 1.23 |  | 9400 |  |  |  |
|  | HPUPT-[P(LLA)-b-P(MTCOPrBr)Ac]$_2$ | 1.26 |  | 9900 |  |  |  |
| Example 4 | HPUBT-[P(LLA)$_{n/2}$-b-P(MTCOPrBr$_{m/2}$*NMe$_3$)Ac]$_2$ |  | 12:10 | 12000 |  | 97 nm (1000 mg/L) 209 nm (3000 mg/L) | 67 mV (1000 mg/L) 57 mV (3000 mg/L) |
| Example 5 | HPUPT--[P(LLA)$_{n/2}$-b-P(MTCOPrBr$_{m/2}$*NMe$_3$)Ac]$_2$ |  | 12:10 | 11800 |  | 20 nm (1000 mg/L) | 69 mV (1 mg/L) |

Figure 10:
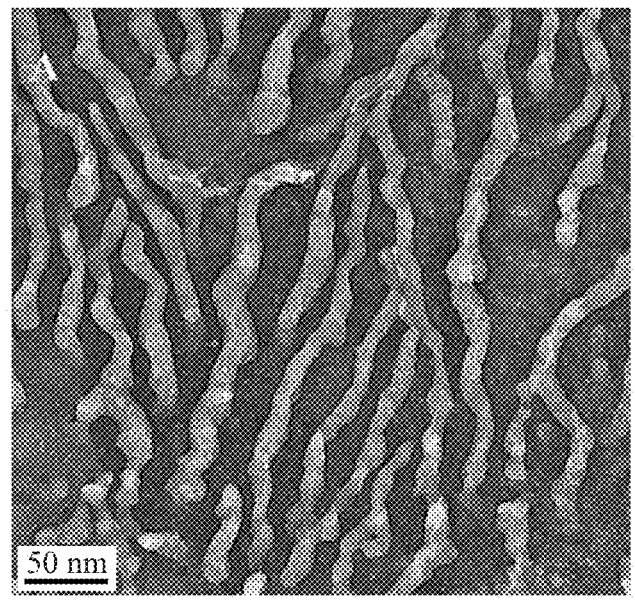
FIG. 10 is a TEM image of the micelles formed with Example 4 (derived from HPUBT initiator) in water at a concentration of 3000 mg/L. The micelles have a rod-like structure in water.
Figure 11:
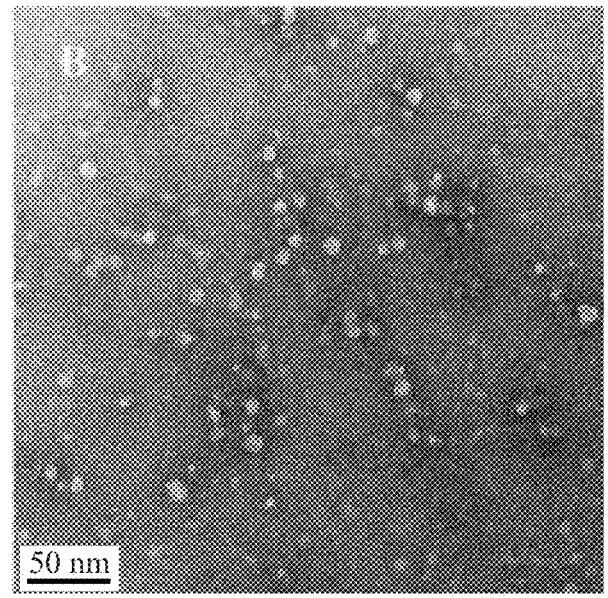
FIG. 11 is a TEM image of the micelles formed with Example 5 (derived from HPUPT initiator) in water at a concentration of 3000 mg/L. The micelles have a spherical structure.

The antimicrobial cationic block copolymers of Examples 4 and 5 comprise a shape-persistent moiety derived from the HPUBT and HPUPT initiators, respectively. Example 4, derived from the less rigid HPUBT initiator, forms rod-like nanostructures in water, as shown in the TEM of FIG. 10. Example 5, derived from the more constrained HPUPT initiator, forms spherical micelles by direct dissolution into water, as shown in the TEM of FIG. 11.

Physicochemical and biological characterization of Examples 4 and 5 (i.e., hemolysis and TEM analyses) and nanostructures was performed using the same methods as those employed for Examples 1 to 3, as described above.

The size of Example 4 micelles measured from dynamic light scattering was 97 nm and 209 nm at concentrations of 1000 and 3000 mg/L, respectively, and that of Example 5 spherical micelles is 20 nm at 1000 mg/L. The zeta potential Other Precursor and Cationic Polymers Example 6

Polymerization of MTCOPrCl

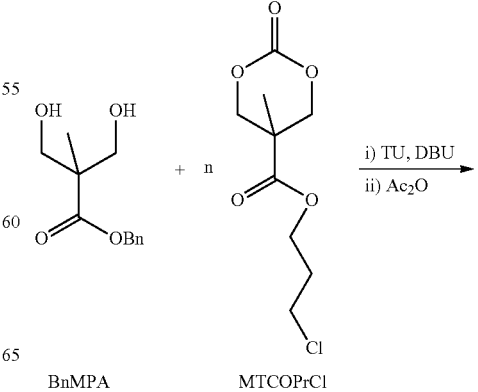

BnMPA     MTCOPrCl

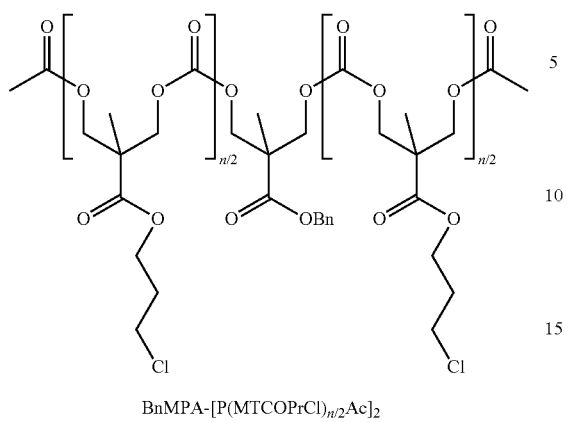

BnMPA-[P(MTCOPrCl)_{n/2}Ac]_2          BnMPA-[P(MTCOPrBr)_{n/2}Ac]_2

MTCOPrCl (501 mg, 2.1 mmol), BnMPA (4.7 mg, 0.02 mmol, initiator), and TU (37.2 mg, 0.1 mmol) were dissolved in methylene chloride (1 mL), and this solution was transferred to a vial containing DBU (15.2 mg, 0.1 mmol) to start polymerization at room, temperature ($[M]_0/[I]_0=100$). After 2 hours, acetic anhydride (72.4 mg, 0.71 mmol) was added into the mixture and the mixture was stirred for 48 hours (conversion ~95%). The solution was then precipitated into cold methanol twice and the precipitate was centrifuged and dried in vacuum. Yield: 466 mg (93%), GPC (THF): $M_n$ 12200 g/mol, PDI 1.17, $^1$H NMR (400 MHz, CDCl$_3$): delta 7.39-7.29 (m, 5H; Ph), 5.16 (s, 2H; PhCH$_2$), 4.38-4.19 (br, ~350H; CH$_2$OCOO, OCH$_2$ polymer), 3.64-3.55 (m, ~117H; CH$_2$Cl polymer), 2.15-2.07 (m, ~114H; CH$_2$ polymer), 2.06 (s, 6H; OCH$_3$ acetyl end), 1.27 (br, ~169H; CH$_3$ polymer).

MTCOPrBr (280 mg, 1.0 mmol), BnMPA (4.5 mg, 0.02 mmol, initiator), and TU (9.8 mg, 0.026 mmol) were dissolved in methylene chloride (1 mL), and this solution was transferred to a vial containing DBU (3.9 mg, 0.026 mmol) to start polymerization at room, temperature ($[M]_0/[I]_0=50$). After 1 hour, acetic anhydride (19.2 mg, 0.18 mmol) was added into the mixture and stirred for 75 hours (conversion 94%). The solution was then precipitated into cold methanol twice and the precipitate was centrifuged and dried in vacuum. Yield: 233 mg (82%), GPC (THF): $M_n$ 11700 g/mol, PDI 1.11, $^1$H NMR (400 MHz, CDCl$_3$): delta 7.41-7.28 (m, 5H; Ph), 5.17 (s, 2H; PhCH$_2$), 4.41-4.14 (m, ~313H; CH$_2$OCOO, OCH$_2$ $_{polymer}$), 3.55-3.36 (m, ~98H; CH$_2$Br$_{polymer}$), 2.26-2.12 (m, ~97H; CH$_2$ $_{polymer}$), 2.06 (s, 6H; OCH$_3$ $_{end\ group}$), 1.36-1.17 (m, ~152H; CH$_3$ $_{polymer}$).

Example 7

Polymerization of MTCOPrBr

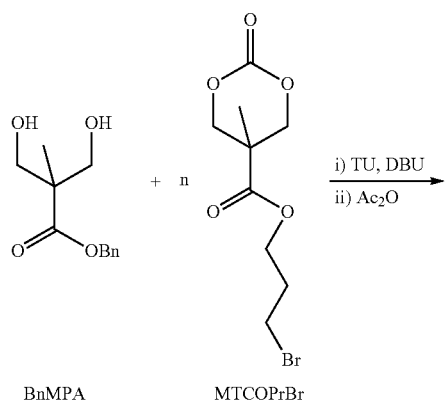

Example 8

Polymerization of MTCOEtI

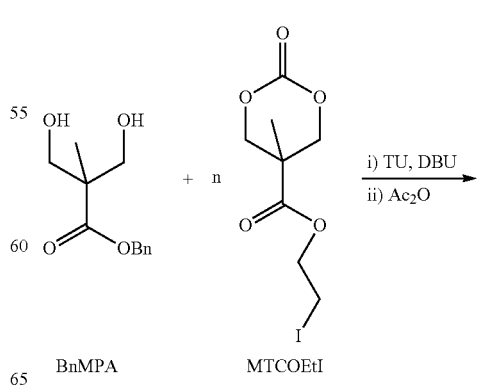

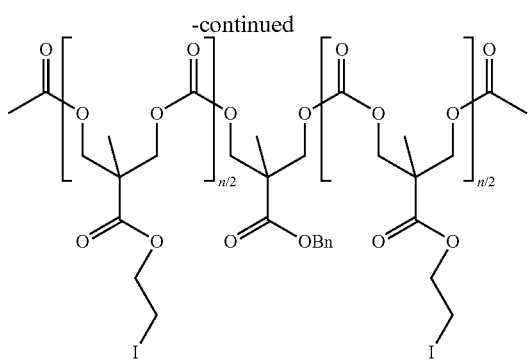

BnMPA-[P(MTCOEtI)_{n/2}Ac]_2

MTCOEtI (312 mg, 1.0 mmol), BnMPA (4.4 mg, 0.02 mmol, initiator), and TU (9.4 mg, 0.03 mmol) were dissolved in methylene chloride (1 mL), and this solution was transferred to a vial containing DBU (3.3 mg, 0.02 mmol) to start polymerization at room temperature ($[M]_0/[I]_0=51$). After 2 hours, acetic anhydride (107.2 mg, 1.05 mmol) was added into the mixture and stirred for 2 nights (conversion 94%). The solution was then precipitated into cold methanol twice and the precipitate was centrifuged and dried in vacuum. Yield: 268 mg (86%), GPC (THF): $M_n$ 10500 g/mol, PDI 1.22, $^1$H NMR (400 MHz, CDCl$_3$): delta 7.37-7.31 (m, 5H; Ph), 5.17 (s, 2H; PhCH$_2$), 4.44-4.36 (m, ~92H; OCH$_2$ polymer), 4.36-4.24 (m, ~178H; CH$_2$OCOO polymer), 3.35-3.27 (m, ~89H; CH$_2$I polymer), 2.07 (s, 6H; OCH$_3$ acetyl end), 1.34-1.24 (br, ~144H; CH$_3$ polymer).

Example 9

Block Polymerization of TMC and MTCOPrCl

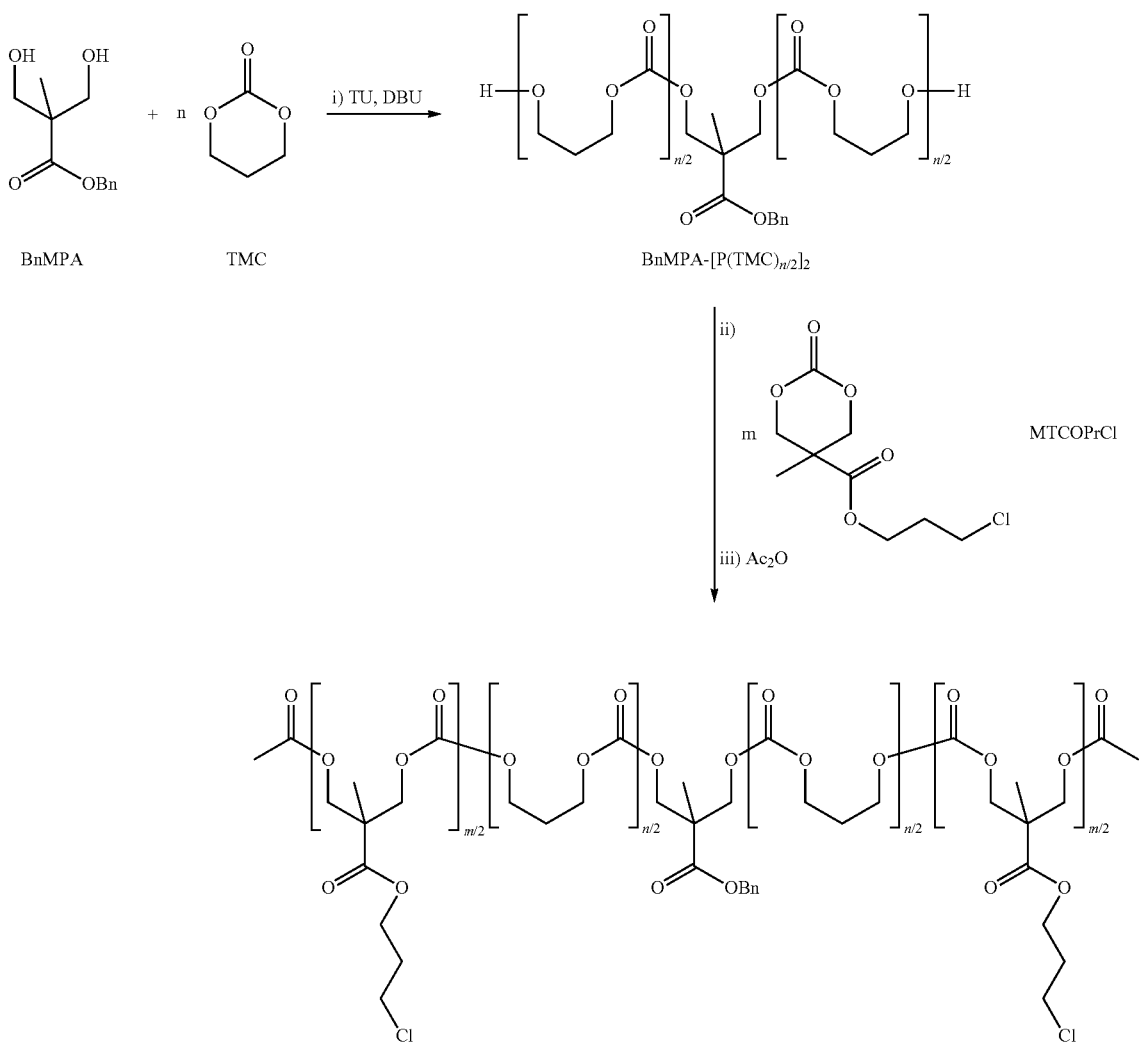

BnMPA-[P(TMC)_{n/2}-b-P(MTCOPrCl)_{m/2}Ac]_2

TMC (108 mg, 1.0 mmol, designated M₁), BnMPA (11 mg, 0.05 mmol), and TU (17.5 mg, 0.05 mmol) were dissolved in methylene chloride (1 mL), and this solution was transferred to a vial containing DBU (7.3 mg, 0.05 mmol) to start polymerization at room temperature ($[M_1]_0/[I]_0=20$). After complete consumption of the first monomer ($M_1$) was confirmed by NMR (3 hours, conversion 97%), the reaction mixture was transferred to a vial containing MTCOPrCl (603 mg, 2.55 mmol), the second monomer $M_2$, for the second polymerization ($[M_2]_0/[I]_0=50$) and stirred for another 18 hours (conversion 96%). Acetic anhydride (117 mg, 1.15 mmol) was then added into the mixture and stirred for 2 nights. The solution was then precipitated into cold methanol twice and the precipitate was centrifuged and dried in vacuum. Yield: 640 mg (90%), GPC (THF): $M_n$ 12000 g/mol, PDI 1.19, ¹H NMR (400 MHz, CDCl₃): delta 7.38-7.30 (m, 5H; Ph), 5.17 (s, 2H; PhCH₂), 4.33-4.26 (m, ~208H; CH₂OCOO, OCH₂ $_{P(MTCprCl)}$), 4.26-4.20 (m, ~70H, CH₂OCOO$_{PTMC}$), 3.63-3.56 (m, ~73H; CH₂Cl$_{P(MTCprCl)}$), 2.15-2.00 (m, ~111H; CH₂ $_{P(MTCprCl)}$, CH₂ $_{PTMC}$, OCH₃ acetyl end), 1.27 (br, ~107H, CH₃ $_{P(MTCprCl)}$).

Polyester-Polycarbonate Block Copolymers.

Example 10

Block Polymerization of LLA and MTCOPrBr

In the following preparation, the stereochemistry of L-lactide (LLA) is not shown.

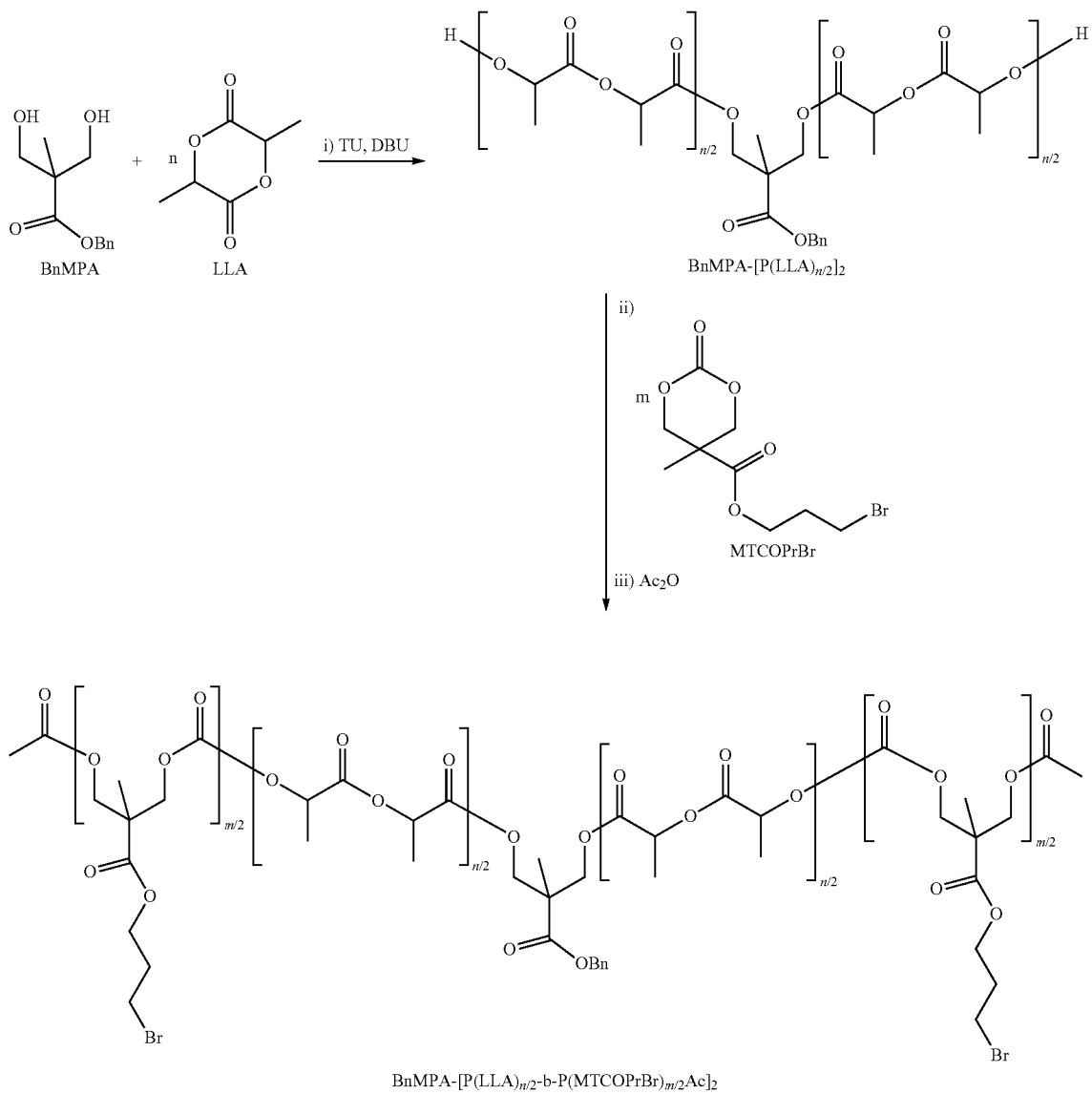

L-lactide (146 mg, 1.0 mmol) (LLA), BnMPA (12 mg, 0.05 mmol), and TU (9.0 mg, 0.024 mmol) were dissolved in methylene chloride (1 mL), and this solution was transferred to a vial containing (−)-sparteine (3.0 mg, 0.013 mmol) to start polymerization at room, temperature ([$M_1$]$_0$/[I]$_0$=20). After complete consumption of the first monomer was confirmed on NMR (1.5 h, conversion 96%), the reaction mixture containing the polyester was transferred to a vial containing MTCOPrBr (427 mg, 1.52 mmol), which was further transferred to a vial containing TU (9.7 mg, 0.026 mmol) and DBU (4.1 mg, 0.027 mmol) for the second polymerization ([$M_2$]$_0$/[I]$_0$=29). The second reaction mixture was stirred for another 1 hour (conversion 97%). Acetic anhydride (205 mg, 2.01 mmol) was then added into the mixture and stirred for 2 nights. The solution was then precipitated into cold methanol twice and the precipitate was centrifuged and dried in vacuum to provide the polyester-polycarbonate block copolymer. Yield: 524 mg (90%), GPC (THF): $M_n$ 12200 g/mol, PDI 1.14, $^1$H NMR (400 MHz, CDCl$_3$): delta 7.38-7.28 (m, 5H; Ph), 5.22-5.09 (m, ~35H; PhCH$_2$, CH$_{PLA}$), 4.38-4.19 (m, ~158H; CH$_2$OCOO, OCH$_2$ $_{P(MTCprBr)}$), 3.48-3.41 (m, ~56H, CH$_2$Br), 2.23-2.14 (m, ~55H; CH$_2$), 2.06 (s, 6H; OCH$_3$ acetyl end), 1.61-1.52 (m, ~106H; CH$_3$ $_{PLA}$), 1.32-1.27 (br, ~86H, CH$_3$ $_{P(MTCprBr)}$).

Example 11

Block Polymerization of DLA and MTCOPrBr

This polymer was prepared by the same procedure as Example 10, adding D-lactide (DLA) as the first monomer instead of L-lactide (LLA). Yield: 503 mg (87%), GPC (THF): $M_n$ 12400 g/mol, PDI 1.13. $^1$H NMR (400 MHz, CDCl$_3$): delta 7.38-7.28 (m, 5H; Ph), 5.22-5.09 (m, ~39H; PhCH$_2$, CH$_{PLA}$), 4.38-4.19 (m, ~195H; CH$_2$OCOO, OCH$_2$ $_{P(MTCprBr)}$), 3.48-3.41 (m, ~63H, CH$_2$Br), 2.23-2.14 (m, ~62H; CH$_2$), 2.06 (s, 6H; OCH$_3$ acetyl end), 1.61-1.52 (m, ~119H; CH$_3$ $_{PLA}$), 1.32-1.27 (br, ~97H, CH$_3$ $_{P(MTCprBr)}$) Random Polycarbonate Copolymer.

Example 12

Random Polymerization of MTCOEt and MTCOPrBr

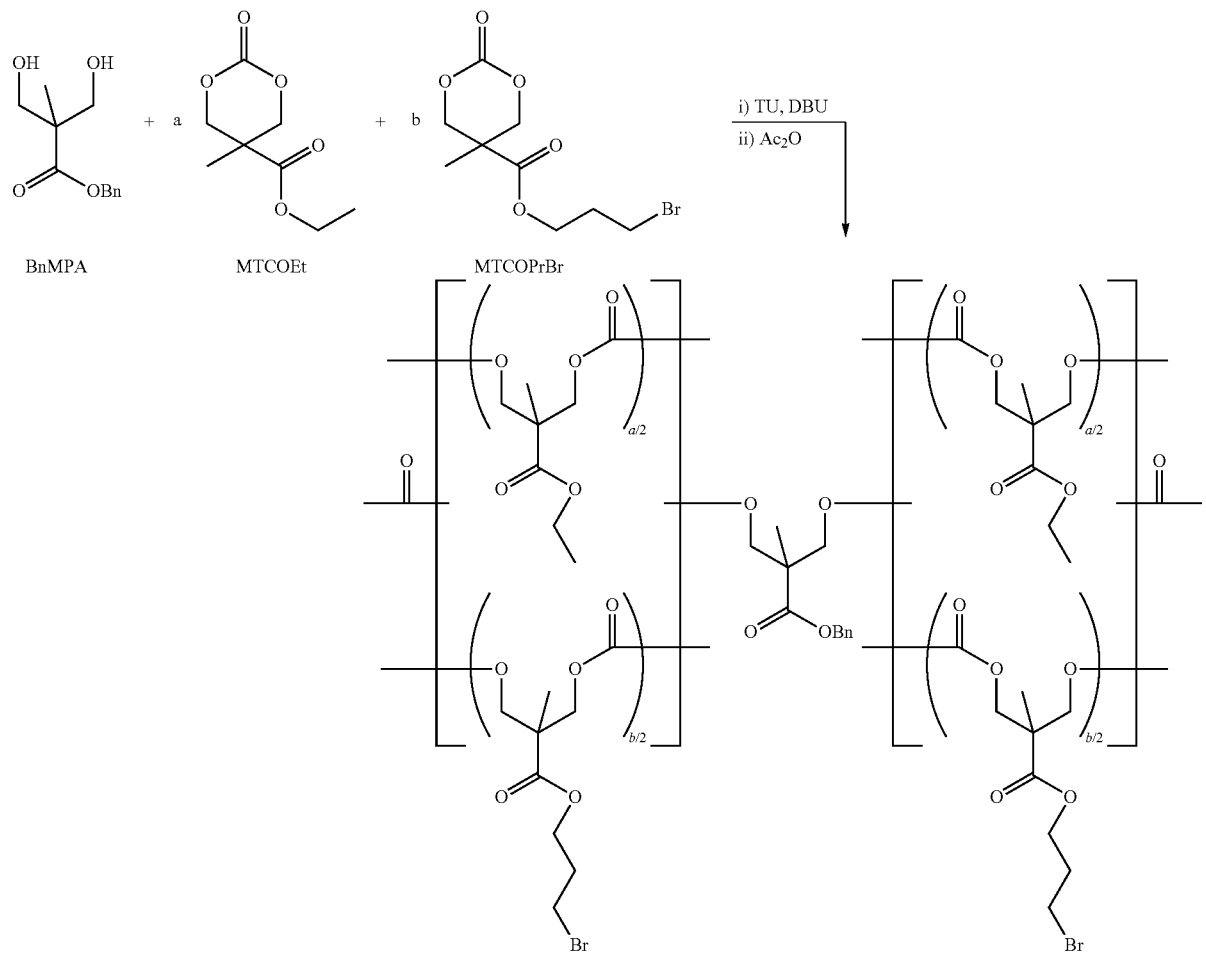

BnMPA-[P(MTCOEt$_{a/2}$-r-MTCOPrBr$_{b/2}$)Ac]$_2$

The vertical brackets in the above structure indicate that either of the repeat units derived from MTCOPrBr or MTCOEt can be bonded to the subunit derived from the initiator, as well as the acetyl group.

MTCOPrBr (282 mg, 1.0 mmol), MTCOEt (188 mg, 1.0 mmol), BnMPA (9.0 mg, 0.04 mmol), and TU (18.7 mg, 0.05 mmol) were dissolved in methylene chloride (1 mL), and this solution was transferred to a vial containing DBU (7.8 mg, 0.05 mmol) to start polymerization at room, temperature ([M]$_0$/[I]$_0$=50). After 2 hours, acetic anhydride (194 mg, 1.90 mmol) was added into the mixture and stirred for 2 nights (conversion 93%). The solution was then precipitated into cold methanol twice and the precipitate was centrifuged and dried in vacuum. Yield: 370 mg (77%), GPC (THF): $M_n$ 11400 g/mol, PDI 1.20, $^1$H NMR (400 MHz, CDCl$_3$): delta 7.37-7.31 (m, 5H; Ph), 5.16 (s, 2H; PhCH$_2$), 4.35-4.24 (m, ~247H; CH$_2$OCOO, OCH$_2$ $_{PMTC(prBr)}$), 4.23-4.14 (m, ~56H; OCH$_2$ $_{PMTC(Et)}$), 3.48-3.41 (m, ~47H; CH$_2$Br), 2.23-2.14 (m, ~47H; CH$_2$ $_{PMTC(prBr)}$), 2.06 (s, 6H; OCH$_3$ acetyl end), 1.30-1.20 (m, ~227H; CH$_3$, CH$_2$CH$_3$ $_{PMTC(Et)}$).

Preparation of Cationic Polymers.

The pre-cationic halo-functional polymers (i.e., first or initial ROP polymers) were reacted with N,N,N',N'-tetramethylethylenediamine (TMEDA) in DMSO to provide the corresponding cationic polymers. Several bis-amines were surveyed, but only tertiary amines were chosen as feasible reagents because the primary and secondary amines led to a significant reduction in the polycarbonate backbone. The "*" before TMEDA or NMe$_3$ in the formula indicates the tertiary amine forms a quaternary salt with the halide containing repeat unit.

Example 13

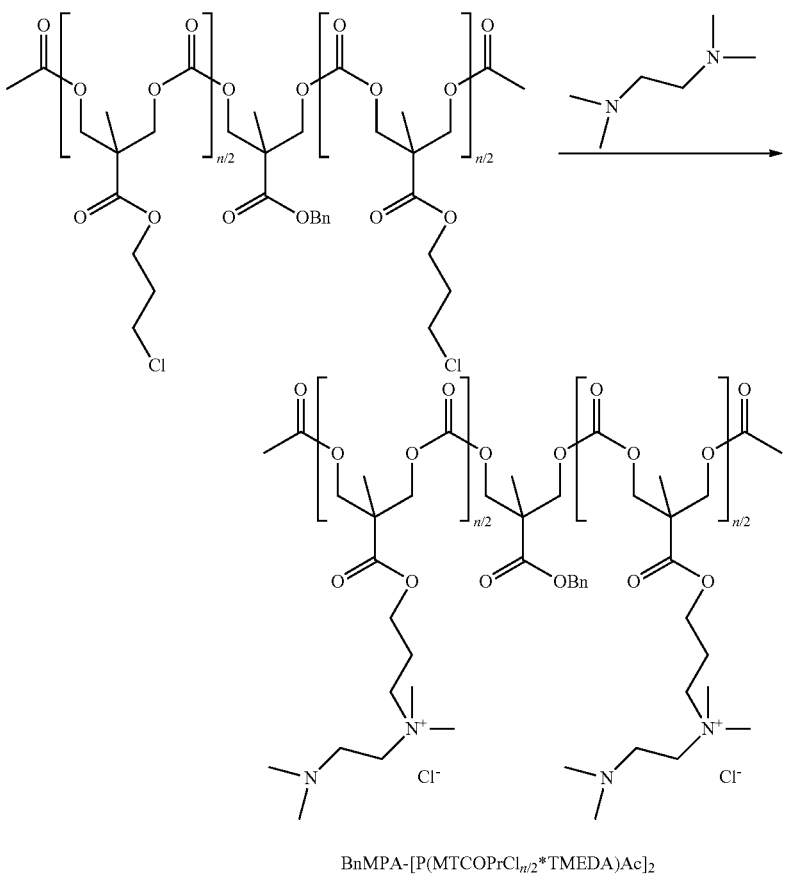

BnMPA-[P(MTCOPrCl$_{n/2}$*TMEDA)Ac]$_2$

The homopolymer of Example 6 (427 mg, [Cl]=1.77 mmol) was dissolved in DMSO (8 mL) and mixed with TMEDA (1.1 mL, 7.22 mmol), and stirred for 6 h at 90° C. The mixture was then precipitated into THF twice and the precipitate was collected by centrifugation and dried in vacuum. Yield: 546 mg (86%), GPC (DMF): $M_n$ 11300 g/mol, PDI 1.27, $^1$H NMR (400 MHz, MeOH-d$_4$): delta 7.42-7.32 (br, 5H; Ph), 5.19 (s, 2H; PhCH$_2$), 4.45-4.17 (m, ~252H; CH$_2$OCOO, OCH$_2$ polymer), 3.63-3.44 (br, ~149H; CH$_2$N$^+$ polymer), 3.27-3.18 (br, ~210H; N$^+$CH$_3$ polymer), 2.85-2.76 (br, ~73H; CH$_2$N polymer), 2.36-2.30 (br, ~213H; NCH$_3$ polymer), 2.28-2.17 (br, ~70H; CH$_2$ polymer), 2.06 (s, 3H; OCH$_3$ acetyl end), 1.34-1.25 (br, ~119H; CH$_3$ polymer), 1.22 (s, 3H; CH$_3$ end group). 85% quaternized; $M_n$=13,900 g/mol (NMR).

Example 14

BnMPA-[P(MTCOPrBr$_{n/2}$*TMEDA)Ac]$_2$

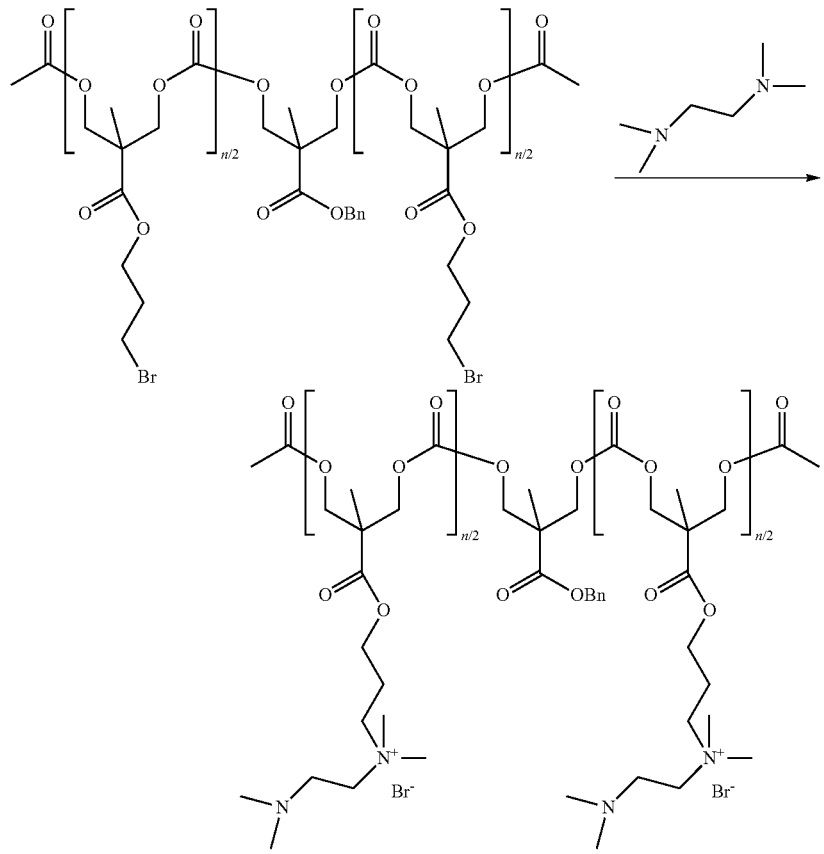

BnMPA-[P(MTCOPrBr$_{n/2}$*TMEDA)Ac]$_2$

TMEDA (0.38 mL, 2.5 mmol) was added to a DMSO solution (3 mL) of the polymer formed in Example 7 (177 mg, [Br]=0.62 mmol). The solution was stirred overnight at room temperature and precipitated into THF twice, and the precipitate was centrifuged and dried in vacuum. Yield: 220 mg (88%), $^1$H NMR (400 MHz, MeOH-d$_4$): delta 7.42-7.30 (br, 5H; Ph), 5.20 (s, 2H; PhCH$_2$), 4.46-4.13 (m, ~266H, CH$_2$OCOO, OCH$_2$ polymer), 3.66-3.42 (br, ~168H; CH$_2$N$^+$ polymer), 3.28-3.17 (br, ~243H; N$^+$CH$_3$ polymer), 2.87-2.75 (br, ~84H; NCH$_2$ polymer), 2.37-2.29 (br, ~251H; NCH$_3$ polymer), 2.30-2.16 (br, ~85H; CH$_2$ polymer), 2.07 (s, 6H; OCH$_3$ acetyl end), 1.37-1.23 (br, ~133H; CH$_3$ polymer). 93% quaternized; M$_n$=17,500 g/mol (NMR).

Example 15

BnMPA-[P(MTCOEtI$_{n/2}$*TMEDA)Ac]$_2$

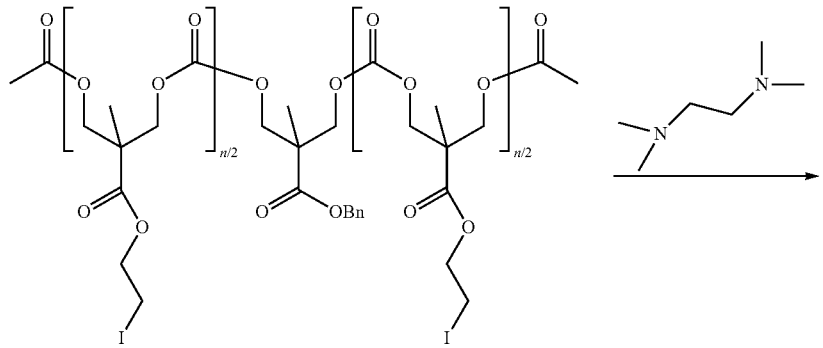

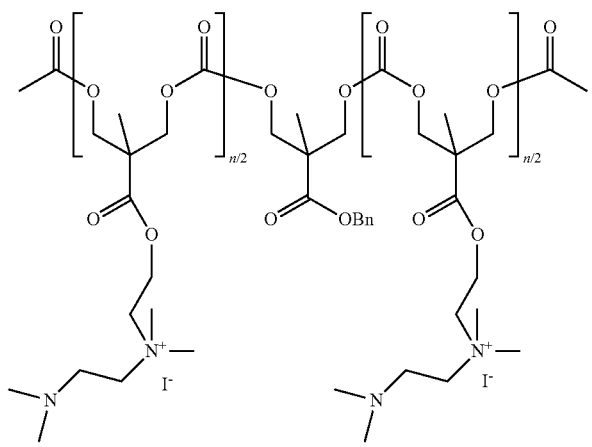

BnMPA-[P(MTCOEtI$_{n/2}$*TMEDA)Ac]$_2$

This cationic polymer was prepared using the same procedure described in Example 14 except with the polymer prepared in Example 8, on a 201 mg scale. Yield: 211 mg (77%), $^1$H NMR (400 MHz, D$_2$O): delta 7.49-7.31 (m, 5H; Ph), 5.22 (s, 2H; PhCH$_2$), 4.69-4.56 (br, ~68H; OCH$_2$), 4.47-4.23 (m, ~176H; OCOCH$_2$), 3.90-3.76 (br, ~74H; N$^+$CH$_2$), 3.66-3.51, (br, ~78H; OCH$_2$CH$_2$N), 3.29-3.15 (br, ~220H; N$^+$CH$_3$), 2.93-2.82 (br, ~76H; NCH$_2$), 2.33-2.23 (br, ~222H; NCH$_3$), 2.07 (s, 6H; CH$_3$ acetyl), 1.38-1.20 (br, ~124H; CH$_3$). 90% quaternized; M$_n$=17,400 g/mol (NMR).

Example 16

BnMPA-[P(TMC)$_{n/2}$-b-P(MTCOPrCl$_{m/2}$*TMEDA)Ac]$_2$

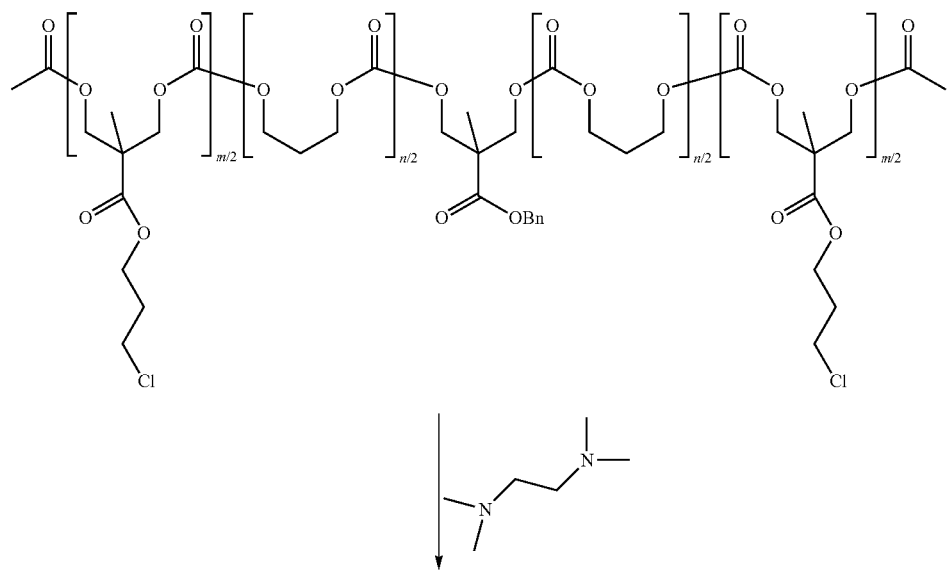

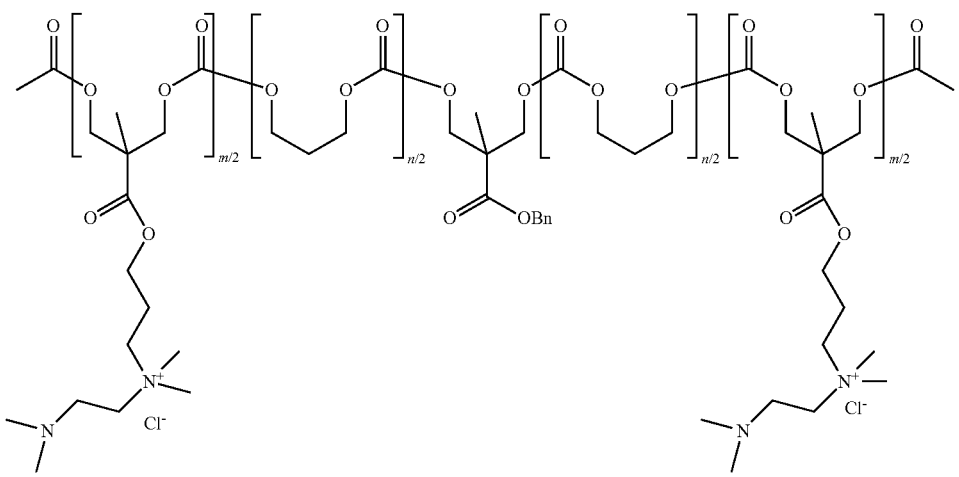

BnMPA-[P(TMC)$_{n/2}$-b-P(MTCOPrCl$_{m/2}$*TMEDA)Ac]$_2$

To a DMSO solution (10 mL) of the polymer formed in Example 9 (578 mg, [Cl]=1.93 mmol), TMEDA (1.27 mL, 8.5 mmol) was added. The reaction mixture was stirred for 6 h at 90° C. and precipitated into THF twice. The precipitate was centrifuged and dried into vacuum. Yield: 735 mg (92%), GPC (DMF): M$_n$ 15700 g/mol, PDI 1.27, $^1$H NMR (400 MHz, MeOH-d$_4$): delta 7.41-7.32 (br, 5H; Ph), 5.19 (br, 2H; PhCH$_2$), 4.48-4.13 (br, ~388H; CH$_2$OCOO, OCH$_2$ polymer), 3.65-3.45 (br, ~179H; CH$_2$N$^+$ polymer), 3.28-3.18 (br, ~270H; N$^+$CH$_3$ polymer), 2.87-2.77 (br, ~88H; NCH$_2$ polymer), 2.38-2.30 (br, ~272H; NCH$_3$ polymer), 2.28-2.16 (br, ~88H; CH$_2$ polymer), 2.08-1.98 (m, ~44H; CH$_2$ polymer, OCH$_3$ acetyl end), 1.35-1.25 (br, ~149H, CH$_3$ polymer). 91% quaternized; M$_n$=18,100 g/mol. (NMR).

Example 17

BnMPA-[P(LLA)$_{n/2}$-b-P(MTCOPrBr$_{m/2}$*TMEDA)Ac]$_2$

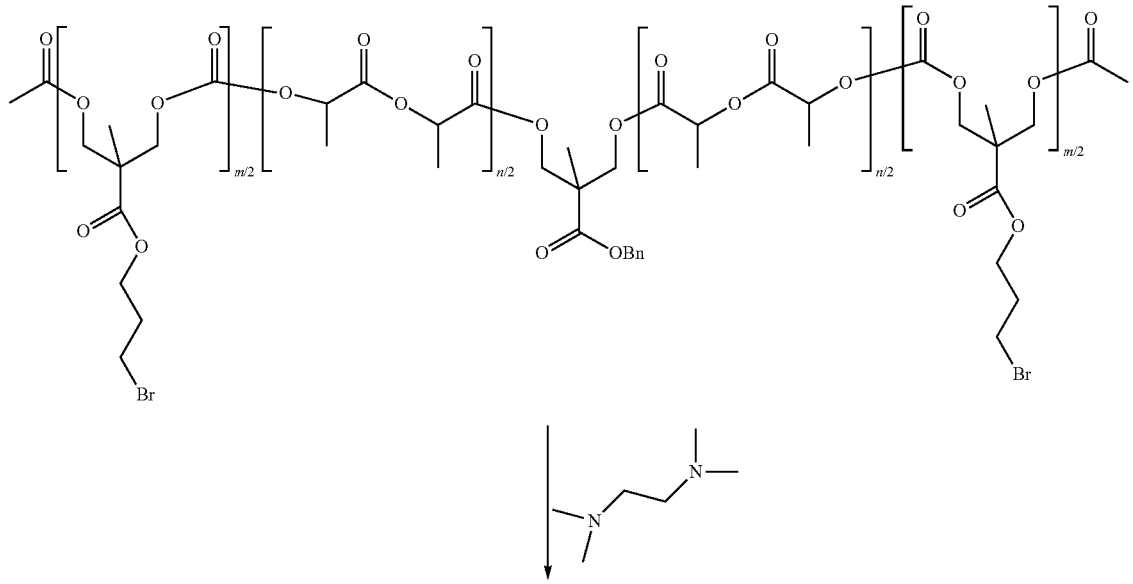

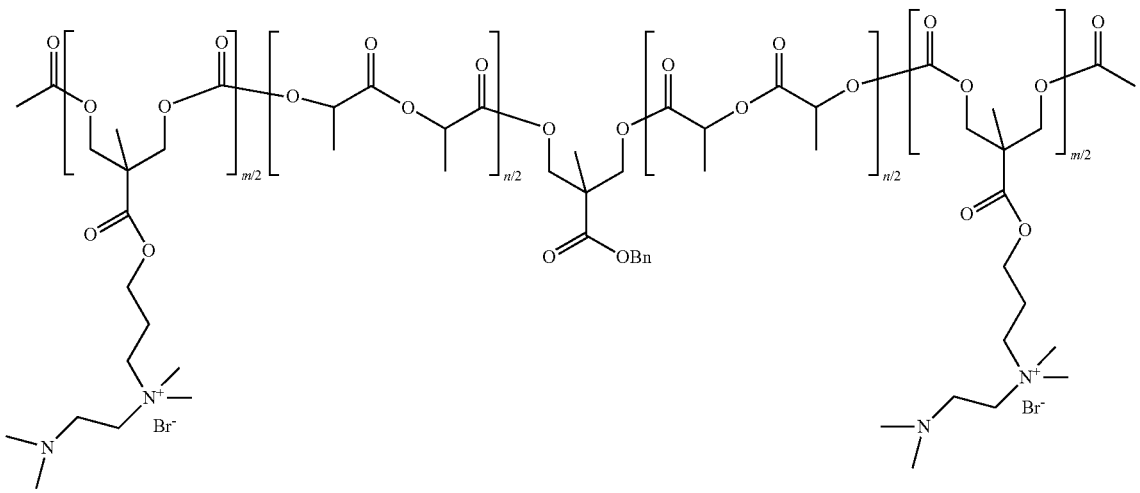

BnMPA-[P(LLA)$_{n/2}$-b-P(MTCOPrBr$_{m/2}$*TMEDA)Ac]$_2$

The polymer formed in Example 10 (406 mg, [Br]=1.07 mmol) and TMEDA (0.65 mL, 4.3 mmol) were mixed in DMSO (4.0 mL), stirred overnight at room temperature and precipitated into THF twice. The precipitate was centrifuged and dried into vacuum. Yield: 515 mg (97%), $^1$H NMR (400 MHz, MeOH-d$_4$): delta 7.42-7.30 (br, 5H; Ph initiator), 5.29-5.11 (m, ~42H; PhCH$_2$ initiator, CH$_{PLA}$), 4.49-4.15 (br, ~204H, CH$_2$OCOO, OCH$_2$ polymer), 3.67-3.43 (br, ~123H, CH$_2$N$^+$ polymer), 3.29-3.15 (br, ~177H, N$^+$CH$_3$ polymer), 2.85-2.74 (br, ~61H, NCH$_2$ polymer), 2.37-2.28 (br, ~189H, NCH$_3$ polymer), 2.29-2.15 (br, ~62H, CH$_2$ polymer), 2.06 (s, 6H, OCH$_3$ acetyl end), 1.60-1.50 (m, ~128H; CH$_{3\ PLA}$), 1.35-1.24 (br, ~103H, CH$_3$). 90% quaternized; M$_n$=16,500 g/mol (NMR).

Example 18

BnMPA-[P(DLA)$_{n/2}$-b-P(MTCOPrBr$_{m/2}$*TMEDA) Ac]$_2$

This polymer from Example 11 was treated with TMEDA according to the procedure used in Example 16 to obtain a cationic polymer, the difference being the subunit derived from DLA rather than LLA. Yield: 497 mg (96%), $^1$H NMR (400 MHz, MeOH-d$_4$): delta 7.42-7.31 (br, 5H; Ph initiator), 5.24-5.13 (m, ~41H; PhCH$_2$ initiator, CH$_{PLA}$), 4.46-4.18 (m, ~206H, CH$_2$OCOO, OCH$_2$ polymer), 3.66-3.45 (br, ~124H, CH$_2$N$^+$ polymer), 3.28-3.18 (br, ~173H, N$^+$CH$_3$ polymer), 2.84-2.75 (br, ~57H, NCH$_2$ polymer), 2.35-2.28 (br, ~175H, NCH$_3$ polymer), 2.28-2.16 (br, ~59H, CH$_2$ polymer), 2.06 (s, 6H, OCH$_3$ acetyl end), 1.59-1.52 (m, ~121H; CH$_{3\ PLA}$), 1.35-1.25 (br, ~110H, CH$_3$). 85% quaternized; M$_n$=16,100 g/mol (NMR).

Example 19
BnMPA-[P(MTCOEt$_{a/2}$-r-MTCOPrBr$_{b/2}$*TMEDA)Ac]$_2$
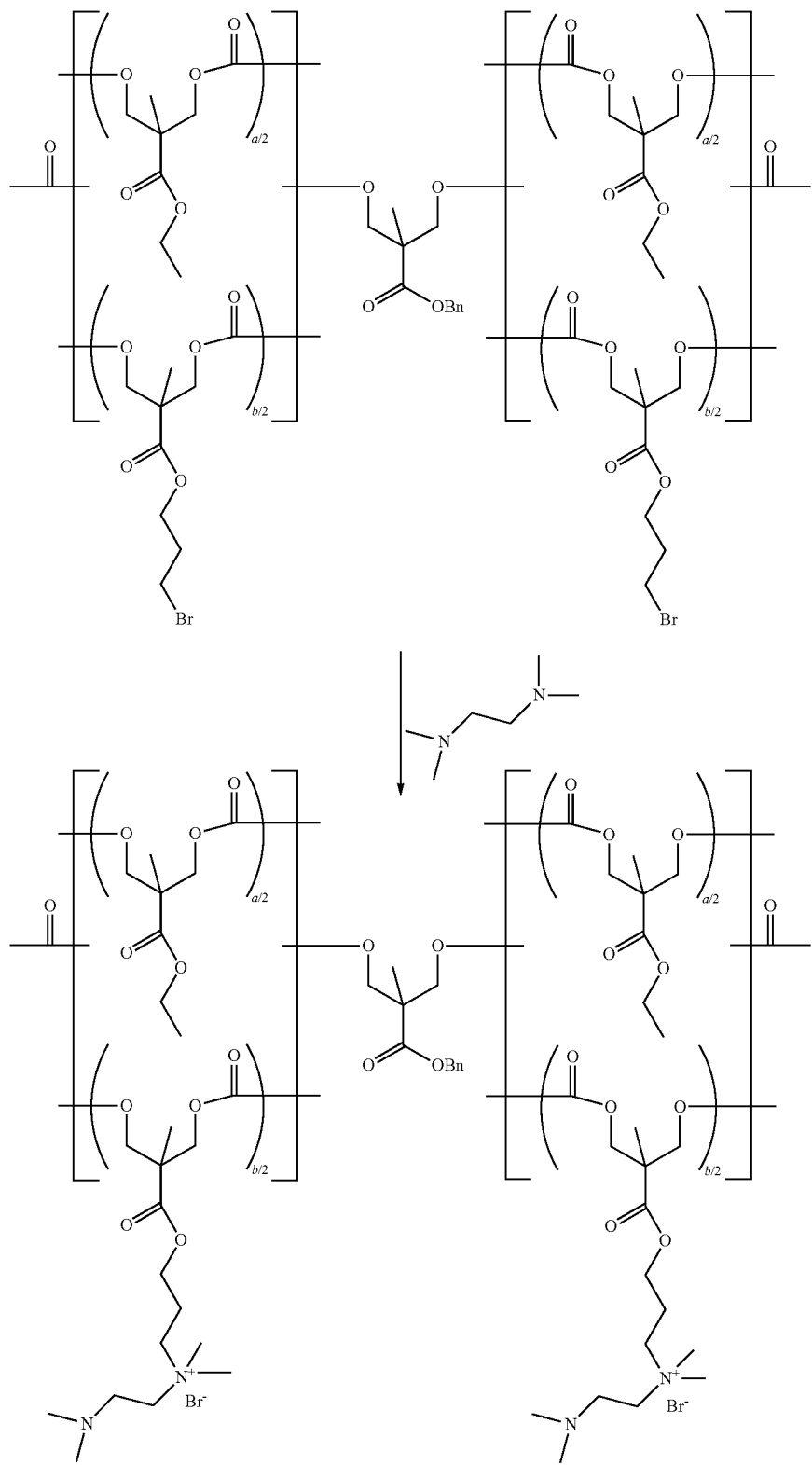
BnMPA-[P(MTCOEt$_{a/2}$-r-MTCOPrBr$_{b/2}$*TMEDA)Ac]$_2$ TMEDA (0.40 mL, 2.69 mmol) was added to a DMSO solution (3 mL) of the polymer from Example 12 (342 mg, [Br]=0.67 mmol). The solution was stirred overnight at room temperature and precipitated into the mixture of THF/hexane (3:1) twice, and the precipitate was centrifuged and dried in vacuum. Yield: 377 mg (90%), $^1$H NMR (400 MHz, MeOH-$d_4$): delta 7.41-7.35 (br, 5H; Ph), 5.19 (s, 2H; PhCH$_2$), 4.42-4.23 (m, ~253H, CH$_2$OCOO, OCH$_2$ $_{PMTC(prBr-N)}$), 4.28-4.13 (m, ~56H; OCH$_2$ $_{PMTC(Et)}$), 3.64-3.49 (br, ~96H; CH$_2$N), 3.28-3.19 (br, ~142H; N$^+$CH$_3$), 2.84-2.75 (br, ~52H; NCH$_2$), 2.35-2.28 (br, ~145H; NCH$_3$), 2.29-2.17 (br, ~49H; CH$_2$ $_{PMTC(prBr-N)}$), 2.06 (s, 6H; OCH$_3$ acetyl end), 1.35-1.19 (m, ~234H; CH$_3$ polymer). 100% quaternized; $M_n$=15,300 g/mol (NMR).

Example 20

BnMPA-[P(MTCOPrBr$_{n/2}$*NMe$_3$)Ac]$_2$

Trimethylamine gas (907 mg, 15.3 mmol) was charged to an acetonitrile solution (5 mL) of BnMPA-[P(MTCOPrBr$_{n/2}$)Ac]$_2$ from Example 7 (203 mg, [Br]=0.71 mmol) immersed in a dry-ice/acetone bath. The solution was then allowed to warm to room temperature and kept stirring for 19 h before acetonitrile and excess gasses were removed under vacuum. The concentrated residue was dried in vacuum. Yield: 207 mg (84%), $^1$H NMR (400 MHz, MeOH-$d_4$): δ 7.45-7.31 (m, 5H; Ph), 5.21 (s, 2H; PhCH$_2$), 4.45-4.20 (m, ~347H; CH$_2$OCOO and CH$_2$O$_{polymer}$), 3.66-3.48 (b, ~113H; N$^+$CH$_2$ $_{polymer}$), 3.29-3.17 (m, ~502H; N$^+$CH$_3$ $_{polymer}$), 2.29-2.17 (b, ~109H; CH$_2$ $_{polymer}$), 2.07 (s, 6H; OCH$_3$ $_{end\ group}$), 1.36-1.25 (m, ~170H; CH$_3$ $_{polymer}$). ~97% quaternized; $M_n$=14,800 g/mol (NMR).

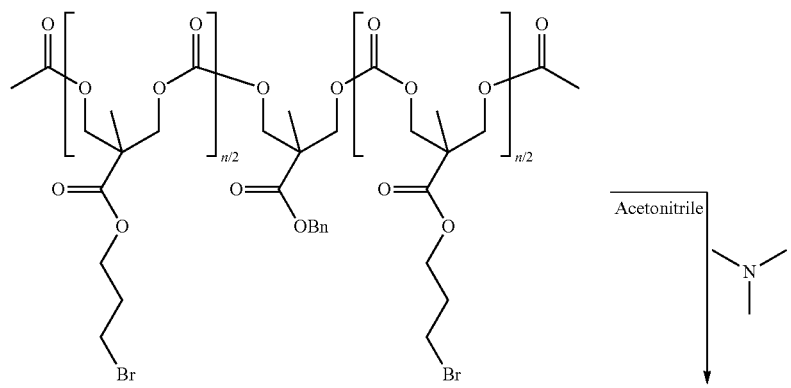

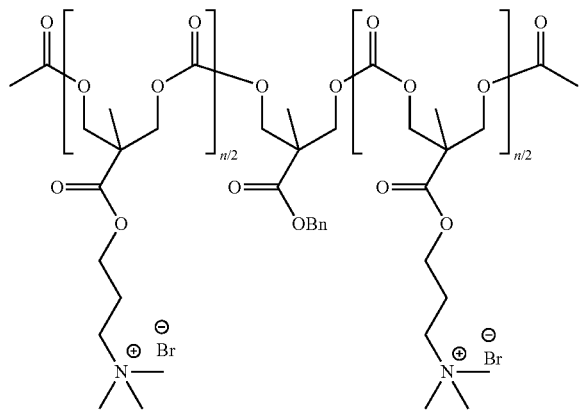

BnMPA-[P(MTCOPrBr$_{n/2}$*NMe$_3$)Ac]$_2$

Example 21

Repeat ROP of MTCOEt and MTCOPrBr with No Endcap

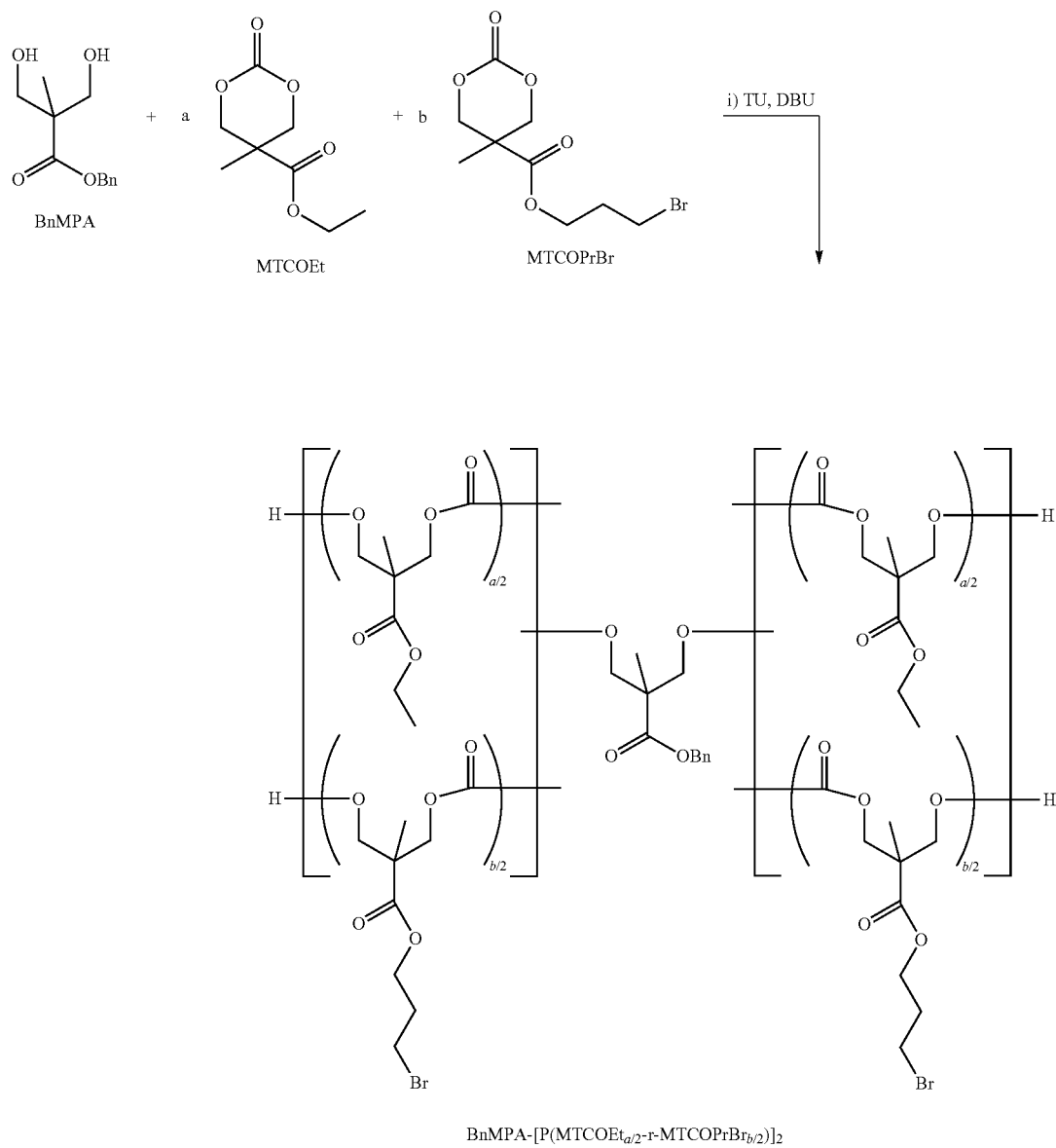

BnMPA-[P(MTCOEt$_{a/2}$-r-MTCOPrBr$_{b/2}$)]$_2$

MTCOEt (50 mg, 0.27 mmol), MTCOPrBr (213 mg, 0.76 mmol), BnMPA (4.5 mg, 0.02 mmol), and TU (18.6 mg, 0.05 mmol) were dissolved in methylene chloride (1.1 mL), and this solution was transferred to a vial containing DBU (8.2 mg, 0.05 mmol) to start polymerization at room, temperature ([M]$_0$/[I]$_0$=51). After 2 hours, the reaction mixture was precipitated into cold methanol and the precipitate was centrifuged and dried in vacuum (conversion ~99%). Yield: 242 mg (91%), GPC (THF): M$_n$ 10900 g/mol, PDI 1.21, $^1$H NMR (400 MHz, acetone-d$_6$): δ 7.46-7.33 (m, 5H; Ph), 5.20 (s, 2H; PhCH$_2$), 4.39-4.25 (m, ~269H; CH$_2$OCOO$_{polymer}$, OCH$_2$ $_{PMTC(BP)}$), 4.22-4.13 (m, ~32H; OCH$_2$ $_{PMTC(Et)}$), 3.74-3.71 (m, 4H; CH$_2$OH$_{end\ group}$), 3.63-3.55 (m, ~70H; CH$_2$Br$_{PMTC(BP)}$), 2.26-2.17 (m, ~69H; CH$_2$ $_{polymer}$), 1.32-1.18 (m, ~201H; CH$_2$CH$_3$ $_{PMTC(Et)}$, CH$_3$ $_{polymer}$).

Example 22

BnMPA-[P(MTCOEt$_{a/2}$-r-MTCOPrBr$_{b/2}$*NMe$_3$)]$_2$

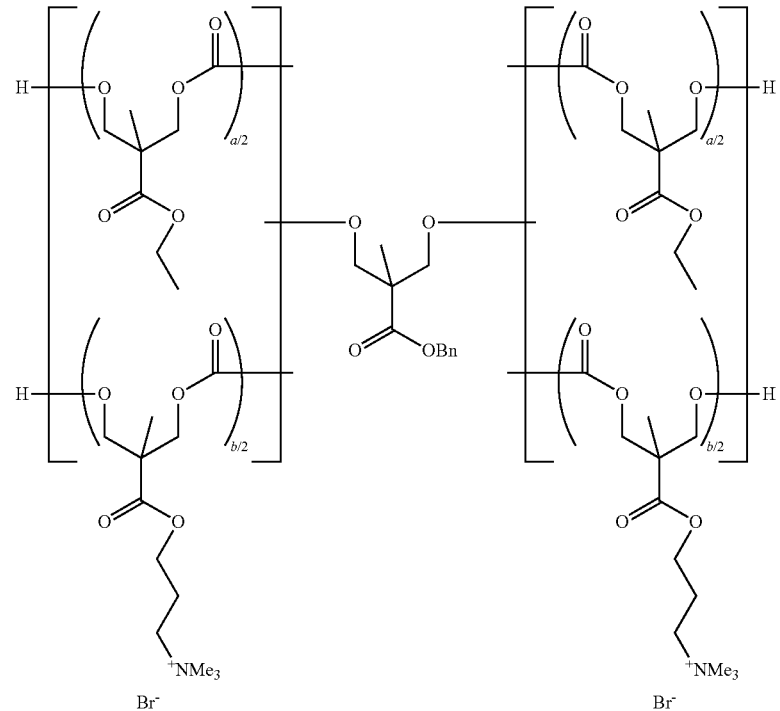

Trimethylamine gas (199 mg, 3.37 mmol) was charged to an acetonitrile solution (4 mL) of BnMPA-[P(MTCOEt$_{a/2}$-r-MTCOPrBr$_{b/2}$)]$_2$ of Example 21 (202 mg, [Br]=0.54 mmol) immersed in a dry-ice/acetone bath. The solution was then allowed to warm to room temperature and kept stirring for 18 hours before acetonitrile and excess gasses were removed under vacuum. The concentrated residue was dried in vacuum. Yield: 182 mg (78%), $^1$H NMR (400 MHz, MeOH-d$_4$): delta 7.44-7.30 (m, 5H; Ph), 5.19 (s, 2H; PhCH$_2$), 4.44-4.24 (m, ~258H; CH$_2$OCOO$_{polymer}$ and CH$_2$O$_{PCPAB}$), 4.23-4.13 (m, ~31H; CH$_2$O$_{PCEt}$), 3.69-3.66 (m, 4H; CH$_2$OH$_{end\ group}$), 3.62-3.47 (b, ~70H; N$^+$CH$_2$ $_{PCPAB}$), 3.29-3.17 (m, ~298H; N$^+$CH$_3$ $_{PCPAB}$), 2.30-2.16 (b, ~69H; CH$_2$ $_{PCPAB}$), 1.37-1.16 (m, ~200H; CH$_2$CH$_3$ $_{PMTC(Et)}$, CH$_3$ $_{polymer}$). ~97% quaternized; M$_n$=14,800 g/mol (NMR).

(i) A mixture of bisMPA (30.4 g, 0.227 mol), potassium hydroxide (88% assay; 13.5 g, 0.241 mol), and a mixture of DMF (20 mL) and acetonitrile (180 mL) was heated to 100° C. for 1 hour. Lauryl bromide (60 mL, 0.250 mol) was added to the warm solution, and stirring was continued at 100° C. for 16 hours. The reaction mixture was cooled to filter salts out and the filtrate was evaporated under vacuum. Ethyl acetate (200 mL) was added to the residue. The organic layer was retained, washed with water (200 mL×3), stirred with MgSO$_4$, and evaporated to give lauryl 2,2-bis(methylol)propionate as a clear oil that solidified after standing for several days (62.2 g, 91%). $^1$H NMR (400 MHz in CDCl$_3$): δ 4.13 (t, 2H, OCH$_2$CH$_2$), 3.88 (d, 2H, CH$_2$OH), 3.69 (d, 2H, CH$_2$OH), 3.02 (b, 2H; OH), 1.64 (m, 2H, OCH$_2$CH$_2$), 1.46-1.17 (m, 18H, CH$_2$), 1.05 (s, 3H, CH$_3$), 0.86 (t, 3H, CH$_2$CH$_3$).

Preparation of Cl2MPA

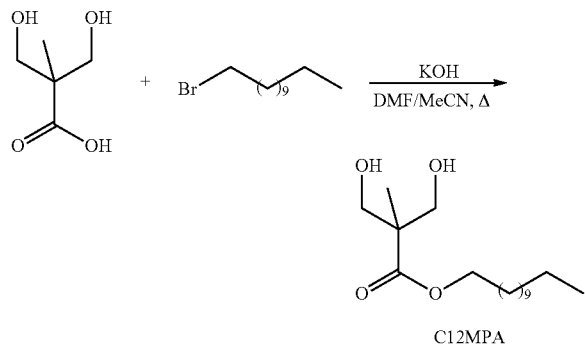

Preparation of MTCOCl2

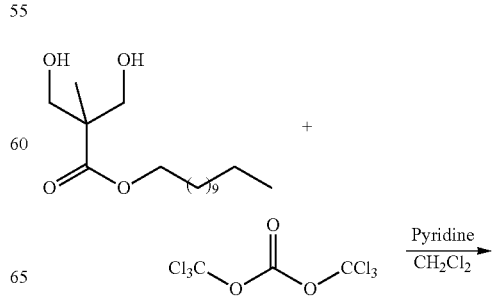

-continued

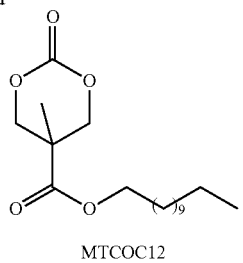
MTCOC12

Lauryl 2,2-bis(methylol)propionate (Cl2MPA) (30.1 g, 0.100 mol) was dissolved in $CH_2Cl_2$ (300 mL) and pyridine (50 mL, 0.6 mol) and the solution was chilled to −78° C. under $N_2$. A solution of triphosgene (15.0 g, 0.05 mol) in $CH_2Cl_2$ was added dropwise over 1 hour, at which point the reaction mixture was allowed to warm to room temperature for 2 hours. The reaction was quenched by addition of saturated aqueous $NH_4Cl$ (200 mL), after which the organic layer was washed with 1 M aqueous HCl (200 mL×3), saturated aqueous $NaHCO_3$ (200 mL), dried over $MgSO_4$, filtered and evaporated to give MTCOCl2 as a white solid (28.1 g, 86%). Material for polymerization was purified by recrystallization from ethyl acetate. $^1H$ NMR (400 MHz in $CDCl_3$): delta 4.68 (d, 2H, $CH_2OCOO$), 4.19 (d, 2H, $CH_2OCOO$), 4.18 (t, 1H, $OCH_2CH_2$), 1.65 (m, 2H, $OCH_2CH_2$), 1.33 (s, 3H, $CH_3$), 1.32-1.21 (m, 18H, $CH_2$), 0.87 (t, 3H, $CH_2CH_3$). $^{13}C$ NMR (100 MHz in $CDCl_3$):delta 171.1, 147.4, 72.9, 66.3, 40.1, 31.8, 29.5, 29.4, 29.3, 29.2, 29.1, 28.3, 25.6, 22. 6, 17.5, 14.0.

Example 23

BnMPA-[P(TMC)$_{n/2}$-b-{P(MTCOPrBr$_{b/2}$-r-MTCOCl2$_{a/2}$}$_m$]$_2$

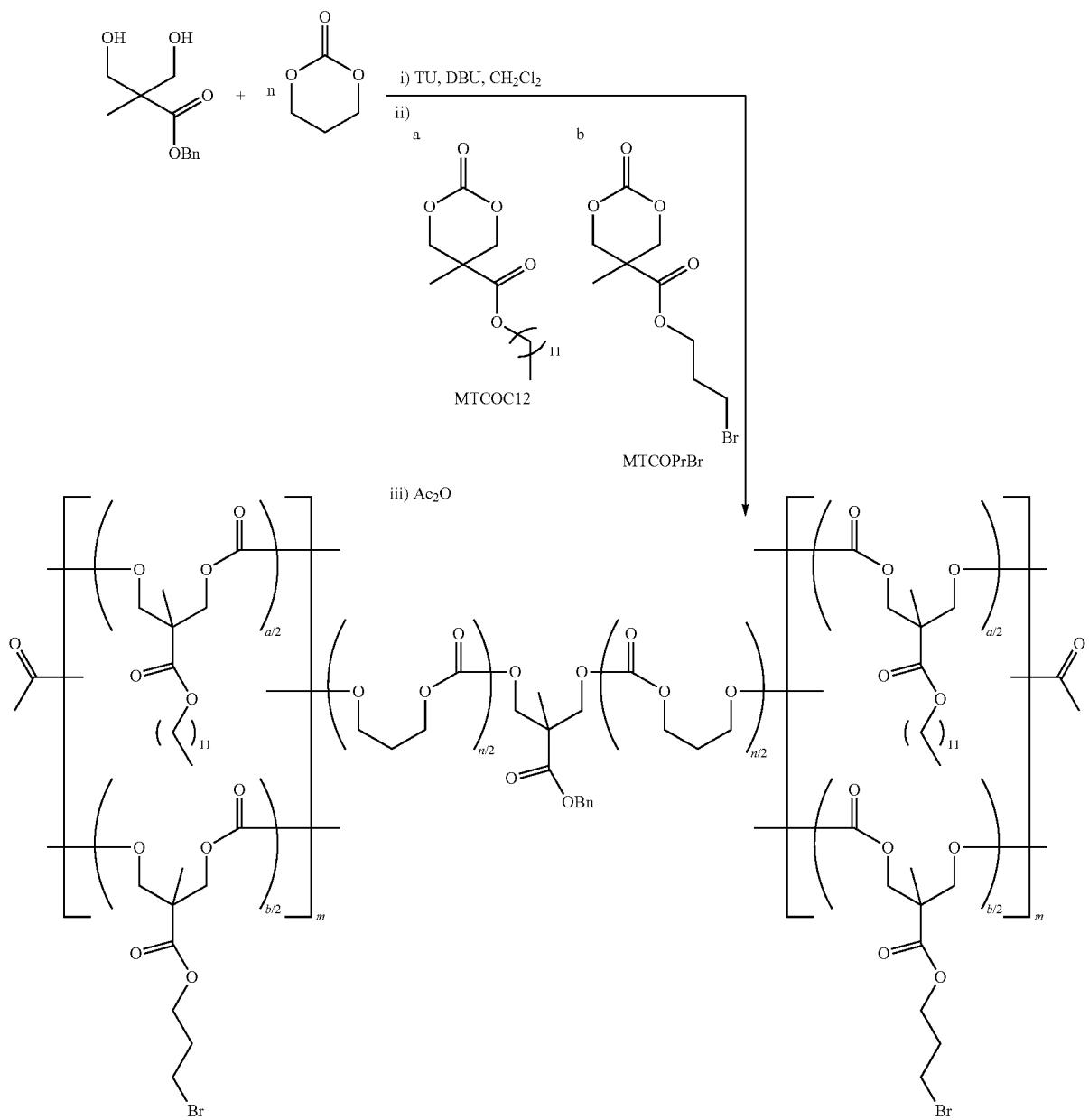

BnMPA-[P(TMC)$_{n/2}$-b-{P(MTCOPrBr$_{b/2}$-r-MTCOCl2$_{a/2}$}$_m$]$_2$

TMC (107 mg, 1.04 mmol), BnMPA (11.3 mg, 0.05 mmol), and TU (10.4 mg, 0.028 mmol) were dissolved in methylene chloride (1.0 mL), and this solution was transferred to a vial containing DBU (4.2 mg, 0.028 mmol) to start polymerization at room, temperature ([TMC]$_0$/[I]$_0$=21). After 3 hours (conversion of TMC ~97%), the solution was transferred to a vial containing MTCOCl2 (69 mmg, 0.21 mmol) and MTCOPrBr (291 mg, 1.03 mmol) to start the second polymerization and stirred for 1 hour at room temperature ([MTC]$_0$/[I]$_0$=25). Then, acetic anhydride (31 mg, 0.30 mmol) was added to the reaction mixture that was precipitated in cold methanol after additional 75 h stirring. The precipitate was centrifuged and dried in vacuum (conversion of MTCs ~97%). Yield: 446 mg (93%), GPC (THF): $M_n$ 10900 g/mol, PDI 1.09, $^1$H NMR (400 MHz, CDCl$_3$): δ 7.38-7.29 (m, 5H; Ph), 5.17 (s, 2H; PhCH$_2$), 4.36-4.17 (m, ~254H; CH$_2$OCOO$_{polymer}$, OCH$_2$ $_{PMTC(BP)}$), 4.14-4.08 (m, ~10H; OCH$_2$ $_{PMTC(Cl2)}$), 3.49-3.41 (m, ~46H; CH$_2$Br$_{PMTC(BP)}$), 2.24-2.14 (m, ~47H; CH$_2$ $_{PMTC(BP)}$), 2.09-2.00 (m, ~49H; CH$_2$ $_{PTMC}$ and OCH$_3$ $_{end\ group}$), 1.67-1.58 (m, ~9H; CH$_2$ $_{PMTC(Cl2)}$), 1.36-1.21 (m, ~172H; CH$_2$ $_{PMTC(Cl2)}$, CH$_3$ $_{PMTC}$), 0.91-0.84 (m, ~13H; CH$_2$CH$_3$ $_{PMTC(Cl2)}$).

Example 24

BnMPA-[P(TMC)$_{n/2}$-b-{P(MTCOPrBr$_{b/2}$*NMe$_3$-r-MTCOCl2$_{a/2}$}$_m$]$_2$

Trimethylamine gas (558 mg, 9.44 mmol) was charged to an acetonitrile solution (5 mL) of BnMPA-[P(TMC)$_{n/2}$-b-{P(MTCOPrBr$_{b/2}$-r-MTCOCl2$_{a/2}$}$_m$]$_2$ from Example 23 (407 mg, [Br]=0.88 mmol) immersed in a dry-ice/acetone bath. The solution was then allowed to warm to room temperature and kept stirring for 20 h before acetonitrile and excess gasses were removed under vacuum. The concentrated residue was dried in vacuum. Yield: 393 mg (82%), $^1$H NMR (400 MHz, MeOH-d$_4$): δ 7.41-7.31 (m, 5H; Ph), 5.19 (s, 2H; PhCH$_2$), 4.44-4.17 (m, ~236H; CH$_2$OCOO$_{polymer}$ and CH$_2$O$_{PCPAB}$), 4.18-4.09 (m, ~10H; CH$_2$O$_{PCCl2}$), 3.64-3.46 (b, ~44H; N$^+$CH$_2$ $_{PCPAB}$), 3.30-3.16 (m, ~189H; N$^+$CH$_3$ $_{PCPAB}$), 2.32-2.16 (b, ~42H; CH$_2$ $_{PCPAB}$), 2.11-1.97 (m, ~46H; CH$_2$ $_{PTMC}$ and OCH$_3$ $_{end\ group}$), 1.72-1.58 (m, ~9H; OCH$_2$CH$_2$ $_{PCCl2}$), 1.45-1.23 (m, ~152H; CH$_2$ $_{PCCl2}$, CH$_3$ $_{polymer}$), 0.95-0.86 (m, ~12H; CH$_2$CH$_3$ $_{PCCl2}$). ~98% quaternized; $M_n$=11000 g/mol (NMR).

Table 10 lists the properties of Examples 20, 22, and 24.

TABLE 10

| Polymer | Mn (from NMR) | PDI (from GPC) | Particle size | Zeta Potential (mV) | CMC (mg/L) | MIC (mg/L) against Bacillus subtilis |
|---|---|---|---|---|---|---|
| Example 20 | 14800 | 1.11 | 262 ± 9 | 33.4 ± 1.8 | 447 | 62.5 |
| Example 22 | 14800 | 1.21 | 142 ± 2 | 66 ± 5.2 | 282 | 31.3 |
| Example 24 | 11000 | 1.09 | 158 ± 3 | 48 ± 3.8 | 12.6 | 62.5 |

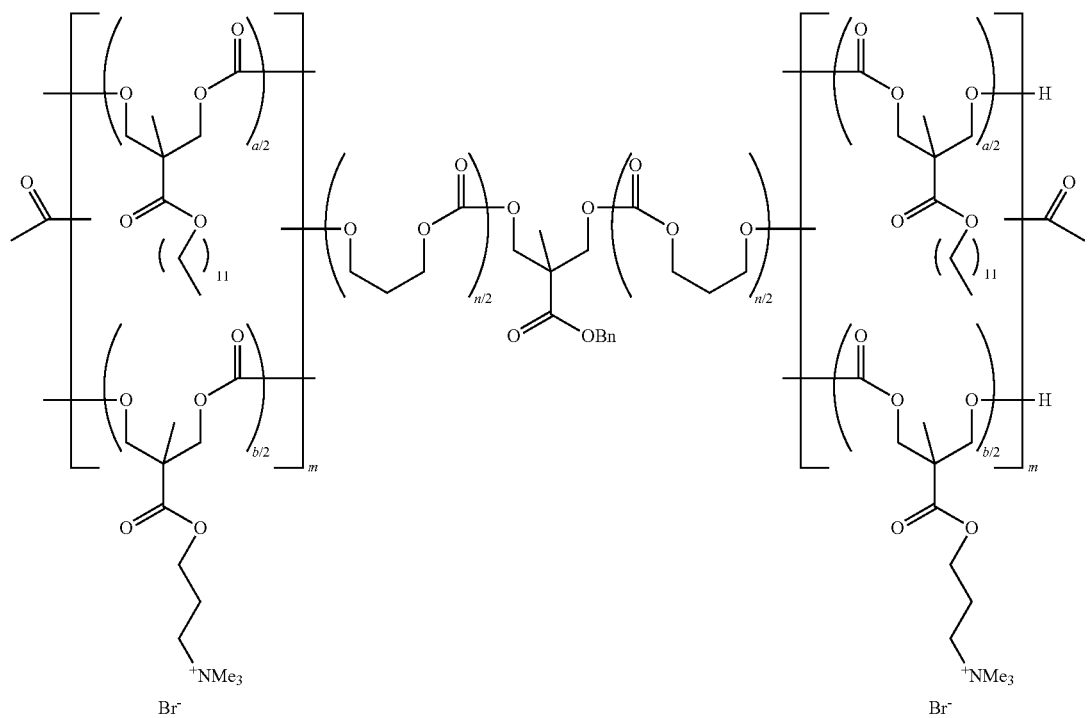

BnMPA-[P(TMC)$_{n/2}$-b-{P(MTCOPrBr$_{b/2}$*NME$_3$-r-MTCOC12$_{a/2}$}$_m$]$_2$

Charge Shifting Polymers.

Example 25

Random copolymer BnMPA-[P(MTCOEE$_{a/2}$-r-MT-COPrBr$_{b/2}$)Ac]$_2$

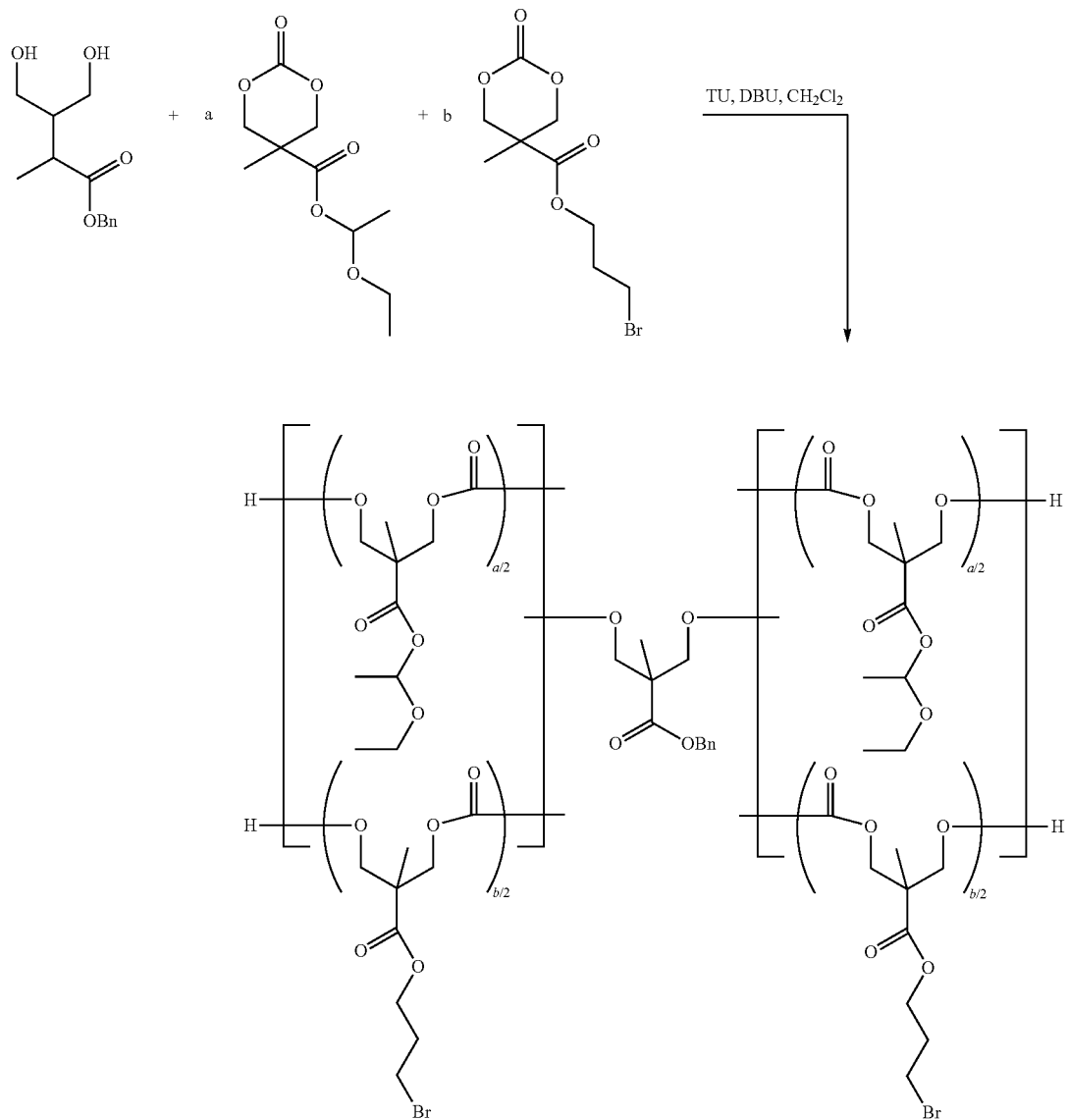

BnMPA-[P(MTCOEE$_{a/2}$-r-MTCOPrBr$_{b/2}$)Ac]$_2$ 5-methyl-5-(1-ethoxyethyl)oxycarboxyl-1,3-dioxan-2-one (MTCOEE; 62 mg, 0.27 mmol), MTCOPrBr (212 mg, 0.75 mmol), BnMPA (4.6 mg, 0.02 mmol), and TU (19.4 mg, 0.05 mmol) were dissolved in methylene chloride (1 mL), and this solution was transferred to a vial containing DBU (7.4 mg, 0.05 mmol) to start polymerization at room temperature ([M]$_0$/[I]$_0$=50). After 2.5 h, the solution was precipitated into cold methanol and the precipitate was centrifuged and dried in vacuum. Yield: 241 mg (87%), GPC (THF): M$_n$ 11800 g/mol, PDI 1.19, $^1$H NMR (400 MHz, acetone-d$_6$): delta 7.45-7.32 (m, 5H; Ph), 5.96 (q, ~12H; CH$_{(OEE)}$), 5.20 (s, 2H; PhCH$_2$), 4.42-4.22 (m, ~333H; CH$_2$OCOO, OCH$_{2\ polymer}$), 3.75-3.48 (m, ~128H; OCH$_{2\ (OEE)}$, CH$_2$Br), 2.27-2.16 (m, ~87H; CH$_{2\ (OPrBr)}$), 1.35 (d, ~44H; CHCH$_{3\ (OEE)}$), 1.33-1.23 (m, ~182H; CH$_{3\ polymer}$), 1.22-1.08 (m, ~69H; CH$_{3\ (OEE)}$). a:b=1.0:3.1.

Example 26
Quaternization of Example 25. BnMPA-[P(MT-COEE$_{a/2}$-r-MTCOPrBr$_{b/2}$*NMe$_3$)Ac]$_2$
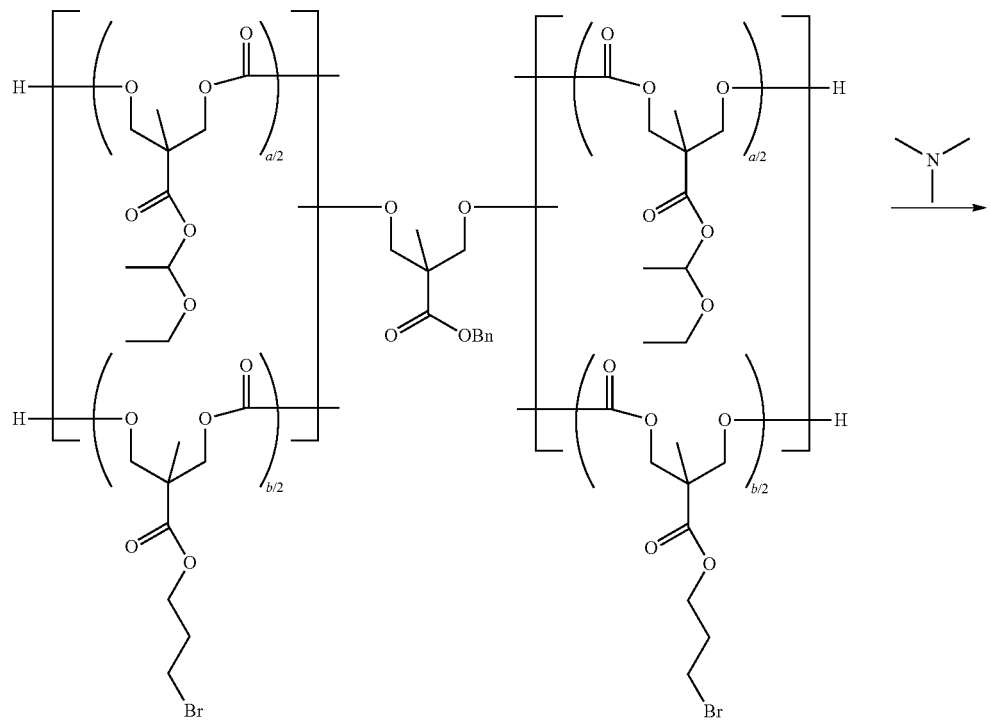
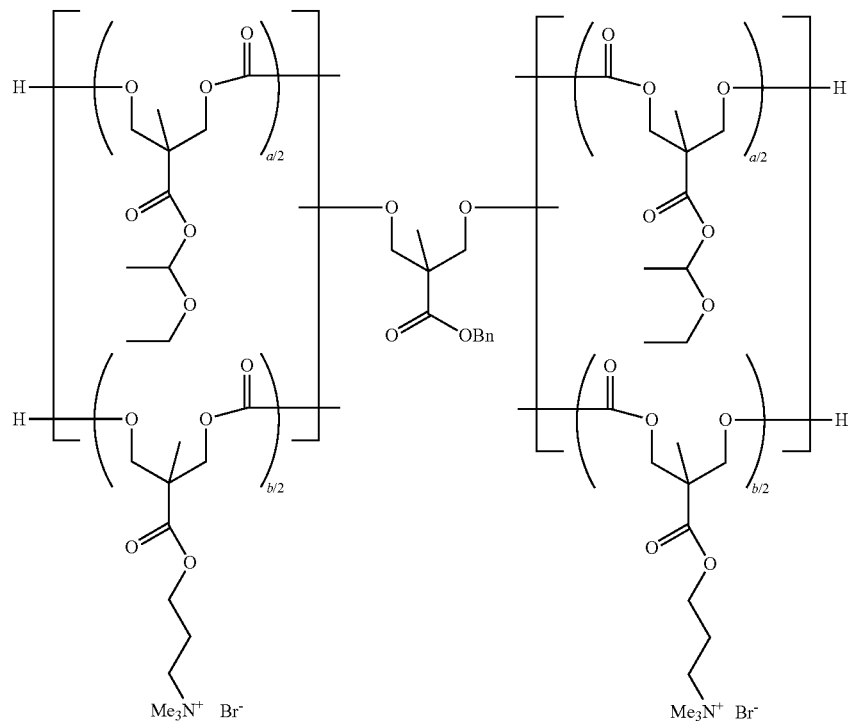
BnMPA-[P(MTCOEE$_{a/2}$-r-MTCOPrBr$_{b/2}$*NMe$_3$)Ac]$_2$ Trimethylamine gas (394 mg, 6.7 mmol) was charged to an acetonitrile solution (4 mL) of the polymer of Example 25 (202 mg, [Br]=0.56 mmol) immersed in a dry-ice/acetone bath. The solution was then allowed to warm to room temperature and kept stirring for 18 h before acetonitrile and excess gasses were removed under vacuum. The concentrated residue was dried in vacuum. Yield: 200 mg (85%), $^1$H NMR (400 MHz, MeOH-d$_4$): delta 7.43-7.32 (m, 5H; Ph), 6.02-5.93 (m, ~6H; CH$_{(OEE)}$), 5.21 (s, 2H; PhCH$_2$), 4.48-4.11 (m, ~267H; CH$_2$OCOO and CH$_2$O$_{polymer}$), 3.75-3.64 (m, ~15H; OCH$_2$CH$_3$ $_{(OEE)}$), 3.63-3.45 (m, ~78H; N$^+$CH$_2$ $_{(PAB)}$), 2.29-2.15 (b, ~298H; N$^+$CH$_3$ $_{(PAB)}$), 2.32-2.15 (b, ~68H; CH$_2$ $_{(PAB)}$), 1.41-1.35 (d, ~19H; CHCH$_3$ $_{(OEE)}$), 1.35-1.23 (m, ~122H; CH$_3$ $_{polymer}$), 1.24-1.10 (m, ~46H; CH$_2$CH$_3$ $_{(OEE)}$), ~90% quaternized; M$_n$ (NMR)=14700 g/mol.

The polymer preparations are summarized in Table 11 for precursor polymers (Examples 6 to 12, and 25) and their corresponding cationic polymers (Examples 13 to 19, and 26)

TABLE 11

Precursor Polymer$^{a,b}$

| Example | Random/Block | M$^1$ | M$^2$ | Cationic Polymer$^c$ Example |
|---|---|---|---|---|
| 6 | | MTCOPrCl | | 13 |
| 7 | | MTCOPrBr | | 14 |
| 8 | | MTCOEtI | | 15 |
| 9 | Block | TMC | MTCOPrCl | 16 |
| 10 | Block | LLA | MTCOPrBr | 17 |
| 11 | Block | DLA | MTCOPrBr | 18 |
| 12 | Random | MTCOEt | MTCOPrBr | 19 |
| 25 | Random | MTCOEE | MTCOPrBr | 26 |

$^a$Each polymerization was initiated with BnMPA.
$^b$M$^1$ was added first for block copolymerizations.
$^c$Quaternizations were performed with TMEDA.

Table 12 summarizes the analytical data (number average molecular weight M$_n$, polydispersity index (PDI), % yield, % conversion of the halide X to quaternary amine) obtained on the precursor polymers (Examples 6 to 12, and 25) and their corresponding cationic polymers (Examples 13 to 19, and 26).

TABLE 12

| Initial ROP Polymer | | | Cationic Polymer | | | | |
|---|---|---|---|---|---|---|---|
| Example | M$_n$$^a$ | PDI$^a$ | Yield (%) | Example | M$_n$$^b$ | Yield (%) | N$^{+ b,c}$ (%) | X |
| 6 | 12200 | 1.17 | 93 | 13 | 13900 | 86 | 85 | Cl |
| 7 | 11700 | 1.11 | 92 | 14 | 17500 | 88 | 93 | Br |
| 8 | 10500 | 1.22 | 86 | 15 | 17400 | 77 | 90 | I |
| 9 | 12000 | 1.19 | 90 | 16 | 18100 | 92 | 91 | Cl |
| 10 | 12200 | 1.14 | 90 | 17 | 16500 | 97 | 90 | Br |
| 11 | 12400 | 1.13 | 87 | 18 | 16100 | 96 | 85 | Br |
| 12 | 11400 | 1.20 | 77 | 19 | 15300 | 90 | ~100 | Br |
| 25 | 11800 | 1.19 | 87 | 26 | 14700 | 85 | 90 | Br |

$^a$ Determined by GPC (THF) using polystyrene standards.
$^b$ Calculated from integral ratios on NMR spectra.
$^c$ Conversion of halogenated residues into quaternary amines.

The utility of the organocatalytic system (TU/DBU) was demonstrated through the synthesis of narrowly dispersed homopolymers, random polymers, and block copolymers having predictable molecular weights. The polydispersity ranged from 1.11 to 1.22. The precursor polymers had a number average molecular weight M$_n$ of 10500 to 12400. The cationic polymers had a number average molecular weight M$_n$ of 13100 to 19433. The conversion of halide to quaternary amine was about 84% to 100%.

The reactivity of the precursor polymer with an amine depends on the halide on the side chain. Although the polymer of Example 6 (X=Cl) can form quaternary amine easily with trimethylamine in acetonitrile at room temperature, it needed more polar solvent such as DMSO and heating (90° C.) to produce the cationic polymer of Example 13 with TMEDA (4 equivalents TMEDA per equivalent of [Cl]). In comparison, the precursor polymers of Example 7 (X=Br) and Example 8 (X=I) were converted at room temperature to the corresponding cationic polymers of Example 14 and 15 respectively, using TMEDA in DMSO or acetonitrile. Little difference was found between the reactivity of bromide and iodide in the reaction rate with TMEDA.

The difference in the reactivity between chlorine, bromine and iodine can be helpful in the design of block copolymers, especially amphiphilic block copolymers to form micelles containing the cationic polycarbonate segments. As shown above, a cationic block copolymer can be formed comprising a cationic hydrophilic segment at both ends (Examples 16 to 18) and a hydrophobic core. The hydrophobic core comprises repeat units derived from trimethylene carbonate (TMC) or a lactide (LLA or DLA). However, the hydrophobic core derived from LLA and DLA was found to be thermally labile during TMEDA quaternization reactions that required heat, in particular with polycarbonate subunits bearing a chloride leaving group. Consequently, these monomers were employed to form precursor polymers having bromide or iodide leaving groups, which could react with TMEDA at room temperature. For precursor polymers comprising chloride leaving groups, a hydrophobic block comprising poly(trimethylene carbonate) derived from TMC was relatively stable at the elevated temperature used in the TMEDA quaternization reaction.

The reactivity of halogens may also affect the stability of the charged polymers. Although around 90% of halogen residues are converted, it is difficult to convert all side chain halide groups to quaternary amine, owing to the reaction equilibrium, steric hindrance, and charge repulsion, even when excess TMEDA is used. The unreacted alkyl halide groups are potential crosslinking sites for reaction with the tertiary amine at the very end of the side chain. The cationic polymers derived from chloride-containing precursor polymers are quite stable because of their low reactivity, whereas the cationic polymers derived from bromide or iodide containing precursor polymers included a small amount of insoluble material. However, no crosslinking was observed in the reaction to produce the cationic polymer of Example 19 derived from the random precursor polymer of Example 12. The cationic polymer of Example 19 showed good solubility in water when the comonomer molar ratio MTCOEt:MTCOPrBr was 1:1.

The above prepared amphiphilic polymers (Examples 13 to 19) can form micellar nanoparticles in aqueous solutions. As a typical example, cationic polymer of Example 16 formed nanoparticles with size of 370 nm and zeta potential of 34 mV by direct dissolution of the polymer in 20 mM sodium acetate buffer (pH 6.0).

Preparation of Homopolymer PBOH-[P(MTCOPr-Cl)$_n$] Using a Mono-Nucleophilic Initiator, 1-pyrenebutanol (PBOH)

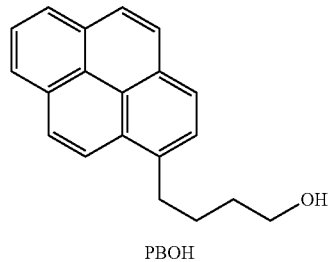

PBOH

+

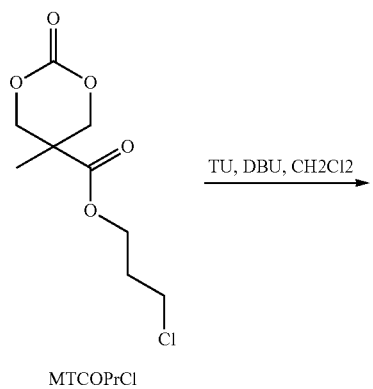

MTCOPrCl

TU, DBU, CH2Cl2 →

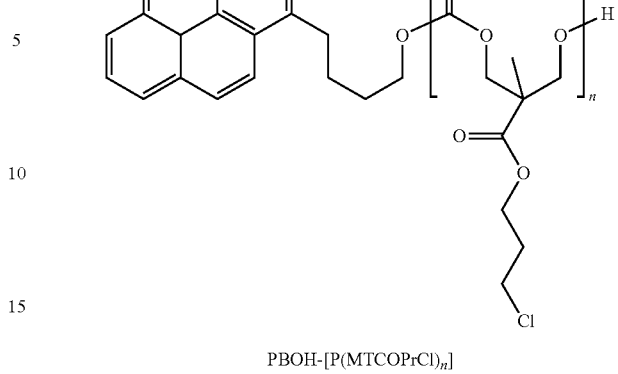

PBOH-[P(MTCOPrCl)$_n$]

MTCOPrCl (233 mg, 0.99 mmol), 1-pyrenebutanol (PBOH) (6.5 mg, 0.024 mmol), and TU (8.2 mg, 0.022 mmol) were dissolved in methylene chloride (1 mL), and this solution was transferred to a vial containing DBU (2.8 mg, 0.018 mmol) to start polymerization at room, temperature ($M_0/[I]_0$=42). After 2 hours, benzoic acid (11.6 mg, 0.10 mmol) was added into the mixture and stirred for 30 min (conversion ~94%). The solution was then precipitated into cold methanol twice and the precipitate was centrifuged and dried in vacuum. Yield: 203 mg (87%), GPC (THF): $M_n$ 5800 g/mol, PDI 1.31, $^1$H NMR (400 MHz, CDCl$_3$): δ 8.29-7.84 (m, 9H; pyrene), 4.49-4.08 (m, ~281H; CH$_2$OCOO, OCH$_{2\,polymer}$ and CH$_2$O), 3.71 (s, 2H; CH$_2$OH$_{end\,group}$), 3.67-3.51 (m, ~96H; CH$_2$Cl$_{polymer}$), 3.43-3.36 (m, 2H; CH$_2$CH$_2$O), 2.17-2.03 (m, ~95H; CH$_{2\,polymer}$), 1.32-1.17 (m, ~144H; CH$_3$ polymer).

Example 27

PBOH-[P(MTCOPrCl)$_n$*TMEDA]

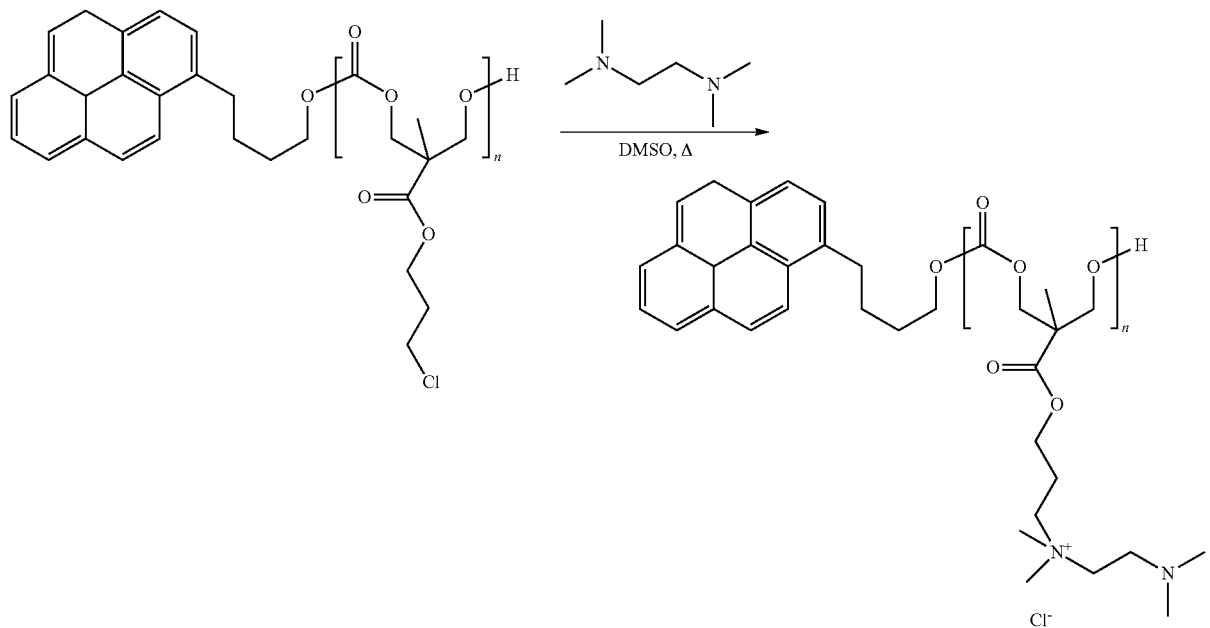

PBOH-[P(MTCOPrCl)$_n$*TMEDA]

PBOH-[P(MTCOPrCl)$_n$] (170 mg, [Cl]=0.69 mmol) was dissolved in DMSO (3.5 mL) and mixed with TMEDA (0.43 mL, 2.87 mmol), and stirred for 16 hours at 80° C. The mixture was then precipitated into THF twice and the precipitate was collected by centrifugation and dried in vacuum (84% quaternized). Yield: 202 mg (81%), GPC (DMF): M$_n$ 7800 g/mol, PDI 1.11, $^1$H NMR (400 MHz, MeOH-d$_4$): delta 8.44-7.92 (m, 9H; pyrene), 4.51-4.12 (m, ~135H; CH$_2$OCOO, OCH$_2$ $_{polymer}$ and CH$_2$O), 3.69 (s, 2H; CH$_2$OH$_{end\ group}$), 3.64-3.42 (m, ~89H; CH$_2$N$^+$$_{polymer}$ and CH$_2$CH$_2$O), 3.29-3.14 (br, ~103H; N$^+$CH$_3$ $_{polymer}$), 2.86-2.74 (br, ~42H; CH$_2$N polymer), 2.30-2.30 (br, ~124H; NCH$_3$ polymer), 2.28-2.14 (br, ~49H; CH$_2$ $_{polymer}$), 1.38-1.24 (br, ~70H; CH$_3$ $_{polymer}$).

Preparation of PBOH-[P(TMC)$_n$-b-P(MTCOPrCl)$_m$] Block Copolymer

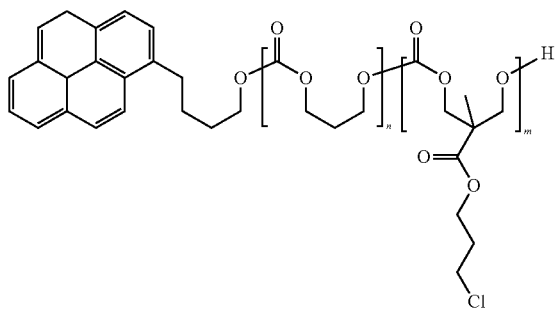

PBOH-[P(TMC)$_n$-b-P(MTCOPrCl)$_m$]

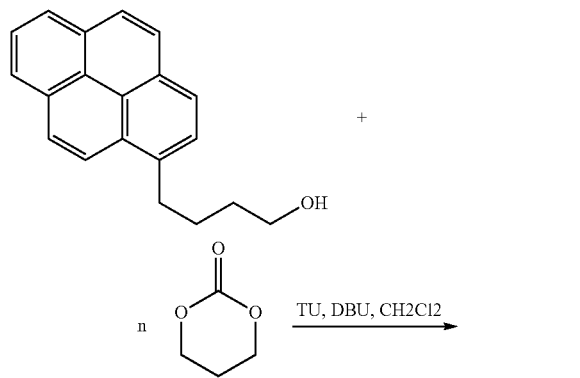

PBOH-[P(TMC)$_n$]

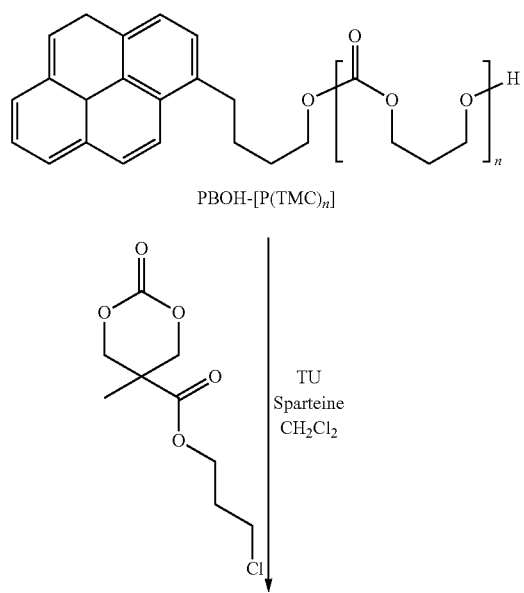

TMC (206 mg, 2.02 mmol), 1-pyrenebutanol (22 mg, 0.08 mmol), and TU (18.0 mg, 0.05 mmol) were dissolved in methylene chloride (1.0 mL), and this solution was transferred to a vial containing DBU (7.5 mg, 0.05 mmol) to start polymerization at room, temperature ([TMC]$_0$/[I]$_0$=26). After 2.5 hours, benzoic acid (10.5 mg, 0.09 mmol) was added into the mixture and stirred for 30 min (conversion ~97%). The solution was then isolated by the precipitation in cold methanol and dried in vacuum to give PBOH-[P(TMC)$_n$]. Yield: 220 mg (97%), GPC (THF): M$_n$ 4000 g/mol, PDI 1.06, M$_n$ (NMR) 2800 g/mol. Then, the polymer PBOH-[P(TMC)$_n$]. (182 mg, [OH]=0.065 mmol), MTCOPrCl (504 mg, 2.13 mmol) and TU (31 mg, 0.08 mmol) were dissolved in methylene chloride (2.1 mL), and this solution was transferred to a vial containing (−)-sparteine (9.5 mg, 0.04 mmol) to start polymerization at room temperature ([M]$_0$/[I]$_0$=33). After 24 hours stirring, benzoic acid (14.5 mg, 0.12 mmol) was added to the solution that was then precipitated into cold methanol twice to be isolated and dried in vacuum to give PBOH-[P(TMC)$_n$-b-P(MTCOPrCl)$_m$]. Yield: 659 mg (96%), GPC (THF): M$_n$ 10700 g/mol, PDI 1.19, $^1$H NMR (400 MHz, CDCl$_3$): δ 8.29-7.83 (m, 9H; pyrene), 4.35-4.17 (m, ~307H; CH$_2$OCOO$_{polymers}$, OCH$_2$ $_{P(MTC-CP)}$ and CH$_2$O), 3.71 (s, 2H; CH$_2$OH$_{end\ group}$), 3.64-3.56 (m, ~71H; CH$_2$Cl$_{P(MTC-CP)}$), 3.39 (t, 2H; CH$_2$CH$_2$O), 2.17-1.98 (m, ~136H; CH$_2$ $_{P(MTC-CP)}$, CH$_2$ $_{PTMC}$), 1.98-1.82 (m, 4H; CH$_2$), 1.32-1.19 (m, ~102H, CH$_3$ $_{P(MTC-CP)}$).

Example 28

PBOH-[(PTMC)$_n$-b-P(MTCOPrCl)$_m$*TMEDA]

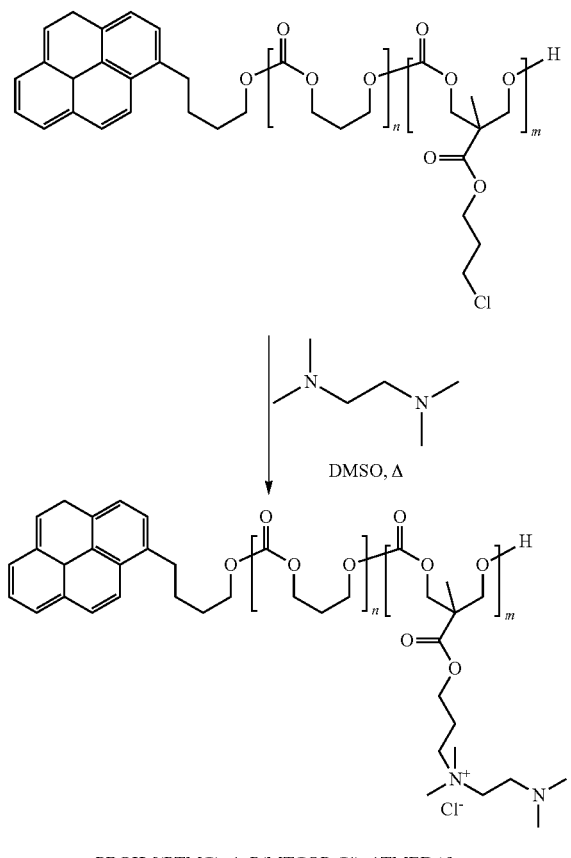

PBOH-[(PTMC)$_n$-b-P(MTCOPrCl)$_m$*TMEDA]

To a DMSO solution (5 mL) of PBOH-[P(TMC)$_n$-b-P(MT-COPrCl)$_m$] (627 mg, [Cl]=1.96 mmol), TMEDA (1.12 mL, 7.5 mmol) was added. The reaction mixture was stirred for 15 hours at 80° C. and precipitated into THF twice. The precipitate was centrifuged and dried in vacuum (82% quarternized). Yield: 772 mg (83%), GPC (DMF): M$_n$ 11500 g/mol, PDI 1.15, $^1$H NMR (400 MHz, MeOH-d$_4$): δ 8.42-7.89 (m, 9H; pyrene), 4.50-4.11 (m, ~210H; CH$_2$OCOO$_{polymers}$, OCH$_{2\ PCPAC}$ and CH$_2$O), 3.69 (s, 2H; CH$_2$OH$_{end\ group}$), 3.65-3.46 (br, ~85H; CH$_2$N$^+_{PCPAC}$), 3.29-3.15 (br, ~125H; N$^+$CH$_{3\ PCPAC}$), 2.98-2.80 (br, ~44H; NCH$_{2\ PCPAC}$), 2.49-2.29 (br, ~124H; NCH$_{3\ PCPAC}$), 2.30-2.14 (br, ~46H; CH$_{2\ PCPAC}$), 2.09-1.92 (m, ~38H; CH$_{2\ PTMC}$), 1.92-1.81 (m, 4H; CH$_2$), 1.39-1.16 (m, ~76H, CH$_3$ polymer).

Table 13 summarizes the CMC, micelle particle size, and MICs of several of the disclosed cationic ROP polymers.

TABLE 13

| Cationic ROP Polymer | CMC (Micrograms/mL) in DI | Micelle Particle Size (nm) | MIC (Micromoles/L) Bacillus subtilis |
|---|---|---|---|
| Example 1 | 35.5 | 43 ± 7 | 12.9 |
| Example 2 | 15.8 | 402 ± 21 | >66.4 |
| Example 3 | 70.8 | 198 ± 9 | 4.5 |
| Example 4 |  | 97 (1 g/L) | 62.5 (mg/L) |
| Example 5 |  | 20 (1 g/L) | 62.5 (mg/L) |
| Example 13 |  |  |  |
| Example 14 |  |  | 125 (mg/L) |
| Example 15 |  |  |  |
| Example 16 |  |  |  |
| Example 17 |  |  |  |
| Example 18 |  |  |  |
| Example 19 |  |  |  |
| Example 20 | 447 | 262 ± 9 | 62.5 (mg/L) |
| Example 22 | 282 | 142 ± 2 | 31.3 (mg/L) |
| Example 24 | 12.6 | 158 ± 3 | 62.5 (mg/L) |
| Example 26 |  |  |  |
| Example 27 |  |  |  |
| Example 28 |  |  |  |

The preferred CMC is under 100 micrograms/mL in deionized water. The preferred micelle particle size is less than 250 nm, and the MIC is preferably under 100 micromoles/L based on M$_n$ of the cationic ROP polymer. As shown in Table 13, the polycarbonates can easily form cationic micelles by direct dissolution in water. The formation of cationic micelles increases the local concentration of cationic charge and polymer mass, enhancing the inhibition effect towards bacterial/fungal growth. The antimicrobial activity of the polymers depends on polymer composition and cell type. Example 2 with a long length of hydrophobic block forms aggregates when in contact with the growth medium. Example 3 with a relatively longer length of cationic block forms micelles whose surfaces have higher zeta potential when compared to Example 1, leading to greater antimicrobial activity. Importantly, Examples 1 and 3 do not possess significant hemolytic activity over a wide range of concentrations. These antimicrobial polycarbonate micelles can be applied to treat various infectious diseases.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. An aqueous micelle mixture, comprising:
about 5 to 500 micrograms/mL of a biodegradable cationic block copolymer, wherein the cationic block copolymer comprises i) a hydrophilic block comprising first repeat units derived from a first cyclic carbonyl monomer by organocatalyzed ring-opening polymerization, wherein the first cyclic carbonyl monomer is a cyclic carbonate and more than 0% of the first repeat units comprise a side chain moiety comprising a positively charged quaternary amine group, ii) a hydrophobic block comprising second repeat units derived from a second cyclic carbonyl monomer by organocatalyzed ring-opening polymerization, the second cyclic carbonyl monomer selected from the group consisting of cyclic carbonate monomers, cyclic ester monomers, and combinations thereof, iii) a chain fragment derived from an initiator for the ring opening polymerization, and iv) an optional endcap group;
wherein the aqueous micelle mixture induces lysis of a microbial cell membrane, and the cationic block copolymer biodegrades 60% within 180 days in accordance with ASTM D6400.

2. The aqueous micelle mixture of claim 1, wherein the chain fragment is derived from a mononucleophilic initiator.

3. The aqueous micelle mixture of claim 1, wherein the initiator is a monomeric alkylene diol initiator selected from the group consisting of ethylene glycols, propylene glycols, butylene glycols, pentylene glycols, hexylene glycols, and mixtures thereof.

4. The aqueous micelle mixture of claim 3, wherein the monomeric alkylene diol initiator is BnMPA.

5. The aqueous micelle mixture of claim 1, wherein the chain fragment is derived from a dinucleophilic initiator having the formula (10):

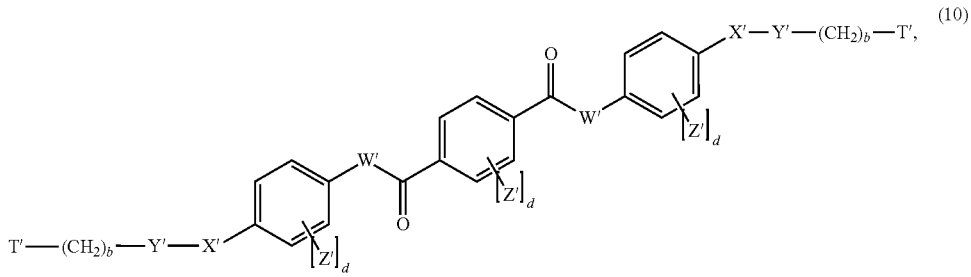

wherein
each X' and each W' is independently a single bond or a divalent radical selected from the group consisting of $-(CR'_2)_c-$, $-O-$, $-S-$, $-NR'-$, and $-NR'(CR'_2)_c-$, wherein each c is an independent integer having a value of 1 to 5, and R' is a monovalent radical selected from the group consisting of hydrogen, alkyl groups comprising 1 to 30 carbons, and aryl groups comprising 6 to 30 carbons, each Y' is independently a single bond or a divalent radical selected from the group consisting of $-CO-$ (carbonyl), $-NR'CO-$ (aminocarbonyl), $-OCO-$ (oxycarbonyl), $-SCO-$ (thiocarbonyl), each T' is an independent monovalent nucleophile selected from the group consisting of $-OH$, $-SH$, $-NH_2$, and $-NR^dH$, wherein $R^d$ is a monovalent radical selected from the group consisting of hydrogen, alkyl groups comprising 1 to 30 carbons, and aryl groups comprising 6 to 30 carbons, each Z' is an independent monovalent radical selected from the group consisting of halides, alkyl groups comprising 1 to 20 carbons, alkoxy groups comprising 1 to 20 carbons, and aryl groups comprising 6 to 20 carbons, each b is an independent integer having a value of 1 to 20; and each d is an independent integer having a value of 0 to 4.

6. The aqueous micelle mixture of claim 5, wherein each d is 0 and each T' is $-OH$ in formula (10).

7. The aqueous micelle mixture of claim 6, wherein each W' is $-NH-$ and each X' is $-NH-$ in formula (10).

8. The aqueous micelle mixture of claim 6, wherein each W' is $-NH-$ and each X' is $-NH(CH_2)-$ in formula (10).

9. The aqueous micelle mixture of claim 6, wherein each Y' is $-NHCO-$ in formula (10).

10. The aqueous micelle mixture of claim 1, wherein the chain fragment is derived from a dinucleophilic initiator having the structure:

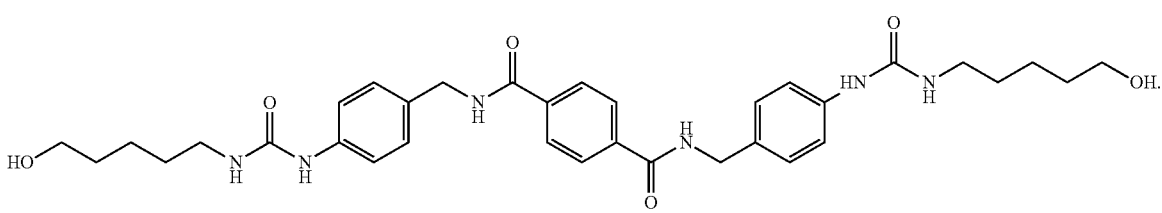 [SMILES: O=C(NCCCCCO)Nc1ccc(CNC(=O)c2ccc(C(=O)NCc3ccc(NC(=O)NCCCCCO)cc3)cc2)cc1]

11. The aqueous micelle mixture of claim 1, wherein the chain fragment is derived from a dinucleophilic initiator having the structure:

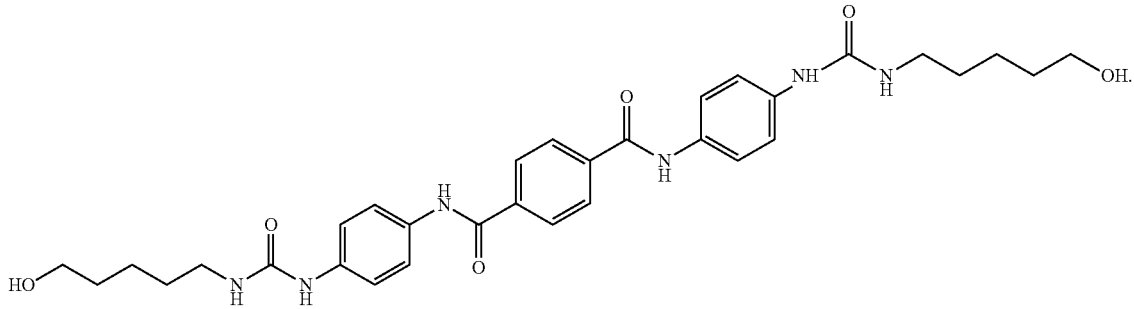 [SMILES: O=C(NCCCCCO)Nc1ccc(NC(=O)c2ccc(C(=O)Nc3ccc(NC(=O)NCCCCCO)cc3)cc2)cc1]

12. The aqueous micelle mixture of claim 1, wherein the quaternary amine is derived from trimethylamine.

13. The aqueous micelle mixture of claim 1, wherein the aqueous micelle has an average particle size of from 10 nm to 500 nm at a pH of from 5.0 to 8.0.

14. The aqueous micelle mixture of claim 1, wherein the aqueous micelle has a spherical structure.

15. The aqueous micelle mixture of claim 1, wherein the aqueous micelle has a rod-like structure.

16. The aqueous micelle mixture of claim 1, wherein the aqueous micelle mixture induces 0% to 15% hemolysis.

17. The aqueous micelle mixture of claim 1, wherein the second cyclic carbonyl monomer is a cyclic carbonate.

18. The aqueous micelle mixture of claim 1, wherein the aqueous micelle is a loaded micelle comprising a biologically active material.

19. The aqueous micelle mixture of claim 18, wherein the biologically active material is not negatively charged.

20. The aqueous micelle mixture of claim 18, wherein the biologically active material is selected from the group consisting of peptides, drugs, and combinations thereof.

21. The aqueous micelle mixture of claim 18, wherein the biologically active material is a drug.

22. The aqueous micelle mixture of claim 1, wherein the first cyclic carbonyl monomer is a compound of formula (2):

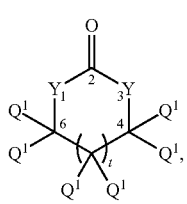

wherein:
t is an integer having a value of 0 to 6,
each Y is —O—, and
each $Q^1$ is an independent monovalent radical selected from the group consisting of hydrogen, halides, carboxy groups, alkyl groups comprising 1 to 30 carbons, aryl groups comprising 6 to 30 carbon atoms, and groups having the structure

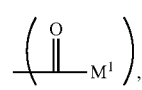

wherein i) $M^1$ is a monovalent radical selected from the group consisting of —$R^1$, —$OR^1$, —$NHR^1$, —$NR^1R^1$, and —$SR^1$ and ii) each $R^1$ is an independent monovalent radical selected from the group consisting of alkyl groups comprising 1 to 30 carbons, and aryl groups comprising 6 to 30 carbons, and
one or more of the $Q^1$ groups of the first cyclic carbonyl monomer comprises a monovalent leaving group capable of reacting with a tertiary amine to form a quaternary amine.

23. The aqueous micelle mixture of claim 22, wherein t is 1 in formula (2).

24. The aqueous micelle mixture of claim 1, wherein the second cyclic carbonyl monomer is a cyclic ester.

25. The aqueous micelle mixture of claim 1, wherein the first cyclic carbonyl monomer is a compound of formula (3):

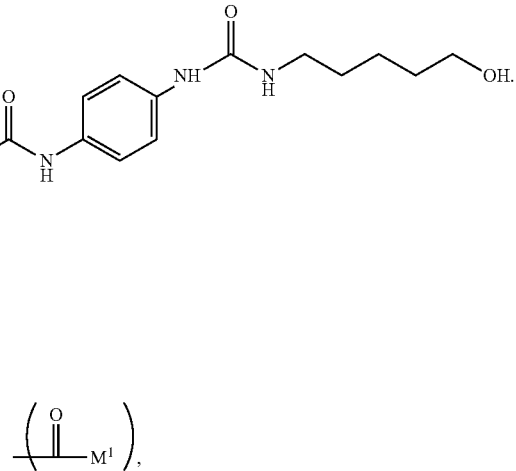

wherein:
each $Q^2$ is an independent monovalent radical selected from the group consisting of hydrogen, halides, carboxy groups, alkyl groups comprising 1 to 30 carbons, aryl groups comprising 6 to 30 carbon atoms, and groups having the structure

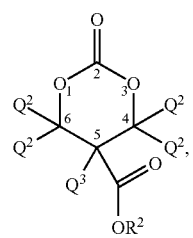

wherein i) $M^1$ is a monovalent radical selected from the group consisting of —$R^1$, —$OR^1$, —$NHR^1$, —$NR^1R^1$, and —$SR^1$ and ii) each $R^1$ is an independent monovalent radical selected from the group consisting of alkyl groups comprising 1 to 30 carbons, and aryl groups comprising 6 to 30 carbons, $R^2$ is an independent monovalent radical selected from the group consisting of alkyl groups comprising 1 to 30 carbons, and aryl groups comprising 6 to 30 carbons, $Q^3$ is a monovalent radical selected from the group consisting of hydrogen, alkyl groups having 1 to 30 carbons, and aryl groups having 6 to 30 carbons, and the $R^2$ group of the first cyclic carbonyl monomer comprises a monovalent leaving group capable of reacting with a tertiary amine to form a quaternary amine.

26. The aqueous micelle mixture of claim 25, wherein each $Q^2$ is hydrogen in formula (3).

27. The aqueous micelle mixture of claim 25, wherein $Q^3$ is hydrogen in formula (3).

28. The aqueous micelle mixture of claim 25, wherein $Q^3$ is methyl or ethyl in formula (3).

29. The aqueous micelle mixture of claim 1, wherein the second cyclic carbonyl monomer is a trimethylene carbonate.

30. The aqueous micelle mixture of claim 1, wherein the second cyclic carbonyl monomer is lactide.

31. A method of forming an aqueous micelle mixture, comprising:

mixing with agitation, at a pH of from 5.0 to 8.0 and at a concentration of 5 to 500 micrograms/mL or more, a biodegradable cationic block copolymer in an aqueous solution, thereby forming an aqueous micelle mixture;

wherein the aqueous micelles have an average particle size of 10 to 500 nm, the cationic block copolymer comprises i) a hydrophilic block comprising first repeat units derived from a first cyclic carbonyl monomer by organocatalyzed ring-opening polymerization, wherein the first cyclic carbonyl monomer is a cyclic carbonate and more than 0% of the first repeat units comprise a side chain moiety comprising a positive charged quaternary amine group, ii) a hydrophobic block comprising second repeat units derived from a second cyclic carbonyl monomer by organocatalyzed ring-opening polymerization, the second cyclic carbonyl monomer selected from the group consisting of cyclic carbonate monomers, cyclic ester monomers, and combinations thereof, iii) a chain fragment derived from an initiator for the ring opening polymerization, and iv) an optional endcap group, and the aqueous micelle mixture induces lysis of a microbial cell membrane, and the cationic block copolymer biodegrades 60% within 180 days in accordance with ASTM D6400.

32. The method of claim 31, wherein the chain fragment comprises two or more backbone aromatic rings derived from a dinucleophilic initiator.

33. The method of claim 31, wherein the initiator is a monomeric alkylene diol selected from the group consisting of ethylene glycols, propylene glycols, butylene glycols, pentylene glycols, hexylene glycols, and mixtures thereof.

34. The method of claim 31, further comprising contacting the first aqueous mixture with a second aqueous mixture comprising a biologically active material.

35. A method of treating a microbe, comprising:

contacting the microbe with an aqueous micelle mixture comprising a biodegradable cationic block copolymer at a pH of from 5.0 to 8.0 and at a concentration effective in the block copolymer inducing lysis of the microbial cell membrane;

wherein the block copolymer comprises i) a hydrophilic block comprising first repeat units derived from a first cyclic carbonyl monomer by organocatalyzed ring-opening polymerization, wherein the first cyclic carbonyl monomer is a cyclic carbonate and more than 0% of the first repeat units comprise a side chain moiety comprising a positive charged quaternary amine group, ii) a hydrophobic block comprising second repeat units derived from a second cyclic carbonyl monomer by organocatalyzed ring-opening polymerization, the second cyclic carbonyl monomer selected from the group consisting of cyclic carbonate monomers, cyclic ester monomers, and combinations thereof, iii) a chain fragment derived from an initiator for the ring opening polymerization, and iv) an optional endcap group, and the cationic block copolymer biodegrades 60% within 180 days in accordance with ASTM D6400.

36. The method of claim 35, wherein the chain fragment comprises two or more backbone aromatic rings derived from a dinucleophilic initiator.

37. The method of claim 35, wherein the initiator is a monomeric alkylene diol selected from the group consisting of ethylene glycols, propylene glycols, butylene glycols, pentylene glycols, hexylene glycols, and mixtures thereof.

* * * * *